(12) United States Patent
Brinker et al.

(10) Patent No.: US 12,208,164 B2
(45) Date of Patent: Jan. 28, 2025

(54) MODULAR METAL-ORGANIC POLYHEDRA SUPERASSEMBLY COMPOSITIONS

(71) Applicant: UNM Rainforest Innovations, Albuquerque, NM (US)

(72) Inventors: C. Jeffrey Brinker, Albuquerque, NM (US); Jimin Guo, Albuquerque, NM (US); Wei Zhu, Albuquerque, NM (US)

(73) Assignee: UNM Rainforest Innovations, Albuquerque, NM (US)

( * ) Notice: Subject to any disclaimer, the term of this patent is extended or adjusted under 35 U.S.C. 154(b) by 528 days.

(21) Appl. No.: 17/434,363

(22) PCT Filed: Feb. 27, 2020

(86) PCT No.: PCT/US2020/020066
§ 371 (c)(1),
(2) Date: Aug. 26, 2021

(87) PCT Pub. No.: WO2020/176716
PCT Pub. Date: Sep. 3, 2020

(65) Prior Publication Data
US 2022/0151924 A1    May 19, 2022

Related U.S. Application Data

(60) Provisional application No. 62/811,668, filed on Feb. 28, 2019.

(51) Int. Cl.
| | | |
|---|---|---|
| *A61K 9/107* | (2006.01) | |
| *A61K 31/704* | (2006.01) | |
| *A61K 33/242* | (2019.01) | |
| *A61K 47/10* | (2017.01) | |
| *A61K 47/24* | (2006.01) | |
| *A61K 47/68* | (2017.01) | |
| *A61K 47/69* | (2017.01) | |
| *A61P 35/00* | (2006.01) | |

(52) U.S. Cl.
CPC .......... *A61K 9/1075* (2013.01); *A61K 31/704* (2013.01); *A61K 33/242* (2019.01); *A61K 47/10* (2013.01); *A61K 47/24* (2013.01); *A61K 47/6849* (2017.08); *A61K 47/6907* (2017.08); *A61P 35/00* (2018.01)

(58) Field of Classification Search
CPC .. A61K 9/1075; A61K 31/704; A61K 33/242; A61K 47/10; A61K 47/24; A61K 47/6849; A61K 47/6907; A61P 35/00
See application file for complete search history.

(56) References Cited

U.S. PATENT DOCUMENTS

| | | | |
|---|---|---|---|
| 4,927,637 A | 5/1990 | Morano et al. | |
| 5,057,296 A | 10/1991 | Beck | |
| 5,098,684 A | 3/1992 | Kresge et al. | |
| 5,360,834 A | 11/1994 | Popall et al. | |
| 5,689,574 A | 11/1997 | Heirich et al. | |
| 5,789,230 A | 8/1998 | Cotten | |
| 6,194,388 B1 | 2/2001 | Krieg et al. | |
| 6,365,266 B1 | 4/2002 | MacDougall et al. | |
| 6,387,453 B1 | 5/2002 | Brinker et al. | |
| 6,808,867 B2 | 10/2004 | Doshi et al. | |
| 6,913,832 B2 | 7/2005 | Fan et al. | |
| 7,101,967 B2 | 9/2006 | Fischer et al. | |
| 7,332,264 B2 | 2/2008 | Doshi et al. | |
| 7,514,267 B1 | 4/2009 | Lopez et al. | |
| 7,563,451 B2 | 7/2009 | Lin et al. | |
| 8,268,962 B2 | 9/2012 | Heemskerk et al. | |
| 8,374,816 B2 | 2/2013 | Vu | |
| 8,734,816 B2 | 5/2014 | Liu et al. | |
| 8,926,994 B2 | 1/2015 | Serda et al. | |
| 8,992,984 B1 | 3/2015 | Brinker et al. | |
| 9,480,653 B2 | 11/2016 | Brinker et al. | |
| 9,579,283 B2 | 2/2017 | Brinker et al. | |
| 9,855,217 B2 | 1/2018 | Brinker et al. | |
| 9,989,447 B1 | 6/2018 | Kaehr et al. | |
| 10,022,327 B2 | 7/2018 | Brinker et al. | |
| 10,465,189 B2 | 11/2019 | Venkatraman et al. | |
| 11,344,629 B2 | 5/2022 | Brinker et al. | |
| 11,672,866 B2 | 6/2023 | Durfee et al. | |
| 2002/0147105 A1 | 10/2002 | Shamshoum et al. | |
| 2004/0005352 A1 | 1/2004 | Lopez et al. | |
| 2004/0258671 A1 | 12/2004 | Watkins | |
| 2005/0239687 A1 | 10/2005 | Divita et al. | |
| 2006/0154069 A1 | 7/2006 | Lin et al. | |
| 2007/0224257 A1 | 9/2007 | Commander et al. | |
| 2007/0287104 A1 | 12/2007 | Doshi et al. | |
| 2007/0298093 A1 | 12/2007 | Konur et al. | |

(Continued)

FOREIGN PATENT DOCUMENTS

| | | |
|---|---|---|
| EP | 1852393 A1 | 11/2007 |
| JP | 2009515520 A | 4/2009 |

(Continued)

OTHER PUBLICATIONS

Zhu et al., Adv. Mater. 2019,31,1806774, 1-10 (published online Jan. 31, 2019). (Year: 2019).*

"International Application Serial No. PCT/US2020/020066, International Search Report mailed Jun. 25, 2020", 2 pgs.

"International Application Serial No. PCT/US2020/020066, Written Opinion mailed Jun. 25, 2020", 4 pgs.

Mohamed, Salma, et al., "(Abstract) Polymeric nano-micelles: versatile platform for targeted delivery in cancer", Ther. Deliv., vol. 5, No. 10, pp. 1101-1121, (Oct. 2014), 1 pg.

(Continued)

*Primary Examiner* — Robert S Cabral
(74) *Attorney, Agent, or Firm* — Schwegman Lundberg & Woessner, P.A.

(57) ABSTRACT

A method to prepare a population of metal-organic polyhedra (MOP) supported micelle nanoparticles (NPs), and a composition comprising MOP supported micelle NPs, are provided.

20 Claims, 18 Drawing Sheets

(56) References Cited

U.S. PATENT DOCUMENTS

| | | |
|---|---|---|
| 2008/0095852 A1 | 4/2008 | Kong et al. |
| 2008/0160313 A1 | 7/2008 | Lopez et al. |
| 2008/0213377 A1 | 9/2008 | Bhatia et al. |
| 2008/0241262 A1 | 10/2008 | Lee et al. |
| 2008/0241917 A1 | 10/2008 | Akita et al. |
| 2008/0286371 A1 | 11/2008 | Pacheco et al. |
| 2009/0054246 A1 | 2/2009 | Peabody et al. |
| 2009/0170931 A1 | 7/2009 | Faulds et al. |
| 2009/0181090 A1 | 7/2009 | Dreis et al. |
| 2009/0208563 A1 | 8/2009 | Watkins et al. |
| 2009/0291131 A1 | 11/2009 | Maclachlan et al. |
| 2009/0305409 A1 | 12/2009 | Kogure et al. |
| 2010/0028341 A1 | 2/2010 | Hermans et al. |
| 2010/0055167 A1 | 3/2010 | Zhang et al. |
| 2010/0152699 A1 | 6/2010 | Ferrari et al. |
| 2010/0166665 A1 | 7/2010 | Butts et al. |
| 2010/0166808 A1 | 7/2010 | Pauletti et al. |
| 2010/0168120 A1 | 7/2010 | Watterson et al. |
| 2010/0255103 A1 | 10/2010 | Liong et al. |
| 2011/0059156 A9 | 3/2011 | Mirkin et al. |
| 2011/0097819 A1 | 4/2011 | Groves et al. |
| 2011/0135571 A1 | 6/2011 | Lin et al. |
| 2011/0230372 A1 | 9/2011 | Willman et al. |
| 2011/0268791 A1 | 11/2011 | Liu et al. |
| 2011/0300186 A1 | 12/2011 | Hellstrom et al. |
| 2012/0207795 A1 | 8/2012 | Zink et al. |
| 2013/0095039 A1 | 4/2013 | Lu et al. |
| 2013/0108661 A1 | 5/2013 | Blander et al. |
| 2013/0115169 A1 | 5/2013 | Lahann et al. |
| 2013/0122054 A1 | 5/2013 | Harashima et al. |
| 2013/0185823 A1 | 7/2013 | Kuang et al. |
| 2013/0195963 A1 | 8/2013 | Serda et al. |
| 2013/0197103 A1 | 8/2013 | Brown |
| 2014/0023700 A1 | 1/2014 | Knudsen et al. |
| 2014/0079774 A1 | 3/2014 | Brinker et al. |
| 2014/0141089 A1 | 5/2014 | Liang |
| 2014/0212479 A1 | 7/2014 | Zeinelden |
| 2014/0234210 A1 | 8/2014 | Lin et al. |
| 2014/0301951 A1 | 10/2014 | Liu et al. |
| 2015/0010475 A1 | 1/2015 | Brinker et al. |
| 2015/0118247 A1 | 4/2015 | Hotson et al. |
| 2015/0125384 A1 | 5/2015 | Mellman et al. |
| 2015/0125391 A1 | 5/2015 | Swami et al. |
| 2015/0164798 A1 | 6/2015 | Brinker et al. |
| 2015/0272885 A1 | 10/2015 | Ashley et al. |
| 2015/0320681 A1 | 11/2015 | Brinker et al. |
| 2016/0008283 A1 | 1/2016 | Nel et al. |
| 2016/0090603 A1 | 3/2016 | Carnes et al. |
| 2016/0106671 A1 | 4/2016 | Brinker et al. |
| 2016/0151482 A1 | 6/2016 | Carnes et al. |
| 2016/0193588 A1 | 7/2016 | Haynes et al. |
| 2016/0287717 A1 | 10/2016 | Brinker |
| 2016/0338954 A1 | 11/2016 | Brinker |
| 2016/0361411 A1 | 12/2016 | Gindy et al. |
| 2017/0042870 A1 | 2/2017 | Xue et al. |
| 2017/0165375 A1 | 6/2017 | Ashley et al. |
| 2017/0232115 A1 | 8/2017 | Ashley et al. |
| 2018/0028686 A1 | 2/2018 | Brinker et al. |
| 2018/0049984 A1 | 2/2018 | Brinker et al. |
| 2018/0105430 A1 | 4/2018 | Carnes et al. |
| 2018/0110831 A1 | 4/2018 | Brinker et al. |
| 2018/0344641 A1 | 12/2018 | Brinker et al. |
| 2019/0022235 A1 | 1/2019 | Durfee et al. |
| 2019/0091150 A1 | 3/2019 | Brinker et al. |
| 2019/0262469 A1 | 8/2019 | Brinker et al. |
| 2019/0330373 A1 | 10/2019 | Stephan |
| 2020/0009264 A1 | 1/2020 | Brinker et al. |
| 2020/0197536 A1 | 6/2020 | Brinker et al. |
| 2020/0375912 A1 | 12/2020 | Serda et al. |
| 2020/0405650 A1 | 12/2020 | Noureddine et al. |
| 2021/0030675 A1 | 2/2021 | Brinker et al. |
| 2021/0315822 A1 | 10/2021 | Guo et al. |
| 2022/0033767 A1 | 2/2022 | Guo et al. |
| 2022/0033768 A1 | 2/2022 | Guo et al. |

FOREIGN PATENT DOCUMENTS

| | | |
|---|---|---|
| WO | WO-9747296 A2 | 12/1997 |
| WO | WO-0076556 A2 | 12/2000 |
| WO | WO-02066506 A2 | 8/2002 |
| WO | WO-03055469 A1 | 7/2003 |
| WO | WO-2004096140 A2 | 11/2004 |
| WO | WO-2005009602 A2 | 3/2005 |
| WO | WO-2005084710 A2 | 9/2005 |
| WO | WO-2007140618 A1 | 12/2007 |
| WO | WO-2009051837 A2 | 4/2009 |
| WO | WO-2010035304 A2 | 4/2010 |
| WO | WO-2010048572 A1 | 4/2010 |
| WO | WO-2010078569 A2 | 7/2010 |
| WO | WO-2011116219 A1 | 9/2011 |
| WO | WO-2011116226 A2 | 9/2011 |
| WO | WO-2011150264 A1 | 12/2011 |
| WO | WO-2012149376 A2 | 11/2012 |
| WO | WO-2013012891 A1 | 1/2013 |
| WO | WO-2013056132 A2 | 4/2013 |
| WO | WO-2013082612 A1 | 6/2013 |
| WO | WO-2013103614 A1 | 7/2013 |
| WO | WO-2014093635 A1 | 6/2014 |
| WO | WO-2014165608 A1 | 10/2014 |
| WO | WO-2014165617 A1 | 10/2014 |
| WO | WO-2015042268 A1 | 3/2015 |
| WO | WO-2015042279 A1 | 3/2015 |
| WO | WO-2015095340 A1 | 6/2015 |
| WO | WO-2015130584 A2 | 9/2015 |
| WO | WO-2016145031 A1 | 9/2016 |
| WO | WO-2016145335 A1 | 9/2016 |
| WO | 2017013250 | 1/2017 |
| WO | WO-2017041032 A1 | 3/2017 |
| WO | WO-2017041033 A1 | 3/2017 |
| WO | WO-2017120504 A1 | 7/2017 |
| WO | WO-2018000043 A1 | 1/2018 |
| WO | WO-2018160865 | 9/2018 |
| WO | WO-2018187287 A1 | 10/2018 |
| WO | WO-2019028387 A1 | 2/2019 |
| WO | WO-2019169152 A1 | 9/2019 |
| WO | WO-2020028342 A1 | 2/2020 |
| WO | WO-2020068798 A1 | 4/2020 |
| WO | WO-2020068806 A1 | 4/2020 |
| WO | WO-2020176716 A1 | 9/2020 |
| WO | 2023147596 | 8/2023 |
| WO | 2024182425 | 9/2024 |

OTHER PUBLICATIONS

Mollick, Samraj, et al., "(Abstract) Outer Surface Hydrophobic Shielding Strategy to Enhance the Chemical Stability of Metal-Organic Polyhedra", Angew Chem Int Ed Engl, vol. 58, No. 4, pp. 1041-1045, (Jan. 21, 2019), 1 pg.

Zhu, Wei, et al., "Modular Metal-Organic Polyhedra Superassambly: From Molecular-Level Design to Targeted Drug Delivery", Adv. Mater., vol. 31, No. 12, 1806774, (Mar. 2019), 10 pgs.

"U.S. Appl. No. 16/068,235, Notice of Allowance mailed Feb. 13, 2023", 5 pgs.

"U.S. Appl. No. 16/068,235, Notice of Allowance mailed Oct. 12, 2022", 5 pgs.

"U.S. Appl. No. 16/068,235, Supplemental Notice of Allowability mailed Feb. 21, 2023", 2 pgs.

"U.S. Appl. No. 16/068,235, Supplemental Notice of Allowability mailed Oct. 17, 2022", 2 pgs.

"U.S. Appl. No. 16/500,349, Final Office Action mailed May 3, 2023", 17 pgs.

"U.S. Appl. No. 16/500,349, Non Final Office Action mailed Nov. 30, 2022", 13 pgs.

"U.S. Appl. No. 16/500,349, Response filed Feb. 28, 2023 to Non Final Office Action mailed Nov. 30, 2022", 8 pgs.

"U.S. Appl. No. 16/500,349, Response filed Aug. 22, 2022 to Restriction Requirement mailed Jun. 22, 2022", 8 pgs.

"U.S. Appl. No. 16/635,246, Advisory Action mailed Jan. 27, 2023", 5 pgs.

"U.S. Appl. No. 16/635,246, Final Office Action mailed Sep. 19, 2022", 19 pgs.

(56) References Cited

OTHER PUBLICATIONS

"U.S. Appl. No. 16/635,246, Non Final Office Action mailed Apr. 10, 2023", 21 pgs.
"U.S. Appl. No. 16/635,246, Response filed Jan. 19, 2023 to Final Office Action mailed Sep. 19, 2022", 7 pgs.
"U.S. Appl. No. 16/635,246, Response filed Mar. 17, 2023 to Advisory Action mailed Jan. 27, 2023", 8 pgs.
"U.S. Appl. No. 16/635,246, Response filed Aug. 31, 2022 to Non Final Office Action mailed May 31, 2022", 8 pgs.
"U.S. Appl. No. 16/976,651, Examiner Interview Summary mailed Jan. 27, 2023", 4 pgs.
"U.S. Appl. No. 16/976,651, Non Final Office Action mailed Feb. 28, 2023", 29 pgs.
"U.S. Appl. No. 16/976,651, Non Final Office Action mailed Nov. 2, 2022", 37 pgs.
"U.S. Appl. No. 16/976,651, Response filed Feb. 1, 2023 to Non Final Office Action mailed Nov. 2, 2022", 13 pgs.
"U.S. Appl. No. 16/976,651, Response filed Oct. 19, 2022 to Non Final Office Action mailed Jul. 19, 2022", 10 pgs.
Berge, Stephen M, et al., "Pharmaceutical Salts", Journal of Pharmaceutical Sciences, 66(1), (Jan. 1977), 1-19.
Doshi, Nishit, et al., "Red blood cell-mimicking synthetic biomaterial particles", PNAS, vol. 106, No. 51, (Dec. 22, 2009), 21495-21499.
Langley, P J, "Nanoporous and mesoporous organic structures: new openings for materials research", Chemical Society Reviews, vol. 28, (1999), 279-291.
Maeder, Morgan L, et al., "CRISPR RNA-guided activation of endogenous human genes", Nature Methods, vol. 10, No. 10, (2013), 977-979.
Merkel, Timothy J., et al., "Using mechanobiological mimicry of red blood cells to extend circulation times of hydrogel microparticles", PNAS, vol. 108, No. 2, (Jan. 11, 2011), 586-591.
Qi, Lei S., et al., "Repurposing CRISPR as RNA-Guided Platform for Sequence-Specific Control of Gene Expression", Cell, 152(5), (2013), 1-22.
Taylor, Erik N., et al., "Monitoring Therapeutic Responses to Silicified Cancer Cell Immunotherapy Using PET/MRI in a Mouse Model of Disseminated Ovarian Cancer", Int. J. Mol. Sci. 2022, 23(18), 10525, (Sep. 10, 2022), 1-14.
Wan, Chao, et al., "Activation of the hypoxia-inducible factor-1a pathway accelerates bone regeneration", PNAS, vol. 105, No. 2, (2008), 686-691.
Wang, Zhen, et al., "Targeting p53 for Novel Anticancer Therapy", Translational Oncology, vol. 3, No. 1, (2010), 1-12.
"U.S. Appl. No. 16/635,246, Advisory Action mailed Oct. 5, 2023", 3 pgs.
"U.S. Appl. No. 16/635,246, Non Final Office Action mailed Nov. 1, 2023", 25 pgs.
"U.S. Appl. No. 16/635,246, Response filed Sep. 25, 2023 to Final Office Action mailed Jul. 25, 2023", 8 pgs.
"U.S. Appl. No. 17/277,260, Restriction Requirement mailed Nov. 20, 2023", 9 pgs.
Lee, Juno, et al., "Chemical sporulation and germination: cytoprotective nanocoating of individual mammalian cells with a degradable tannic acid-Fell I complex", Nanoscale 7(45), (2015), 18918-18922.
Valentina, Colapicchioni, et al., "Killing cancer cells using nanotechnology: novel poly(I:C) loaded liposome-silica hybrid nanoparticles", Journal of Materials Chemistry B, vol. 3, (2015), 7408-7416.
"International Application Serial No. PCT US2023 061675, International Search Report mailed May 24, 2023", 6 pgs.
"International Application Serial No. PCT US2023 061675, Written Opinion mailed May 24, 2023", 6 pgs.
"U.S. Appl. No. 16/976,651, Response filed Jun. 28, 2023 to Non Final Office Action mailed Feb. 28, 2023", 11 pgs.
"U.S. Appl. No. 16/635,246, Response filed Jul. 10, 2023 to Non Final Office Action mailed Apr. 10, 2023", 9 pgs.
"U.S. Appl. No. 16/635,246, Final Office Action mailed Jul. 25, 2023", 23 pgs.
"U.S. Appl. No. 16/976,651, Final Office Action mailed Jul. 27, 2023", 25 pgs.
Brinker, C J, "2021-023—Triplex Nanoparticles for Targeted Gene Delivery", UNM Rainforest Innovations, [Online]. Retrieved from the Internet: https: unm.flintbox.com technologies c52813ba-2361-47e9-baca-e6f39303b3fd, (Apr. 28, 2021), 1-2.
Noureddine, A, "Engineering of monosized lipid-coated mesoporous silica nanoparticles for CRISPR delivery", Acta Biomaterialia, Epub. vol. 114, (Jul. 21, 2020), 358-368.
U.S. Appl. No. 09/838,153 U.S. Pat. No. 6,471,761, filed Apr. 20, 2001, Rapid Prototyping of Patterned Organic/Inorganic Functional Nanostructures.
U.S. Appl. No. 10/163,425 U.S. Pat. No. 6,913,832, filed Jun. 7, 2002, Prototyping of Patterned Functional Nanostructures.
U.S. Appl. No. 09/543,572, filed Apr. 5, 2000, Photo-Definable Self-Assembled Materials.
U.S. Appl. No. 10/100,108 U.S. Pat. No. 6,808,867, filed Mar. 19, 2002, Photo-Definable Self-Assembled Materials.
U.S. Appl. No. 10/373,565 U.S. Pat. No. 7,332,264, filed Feb. 26, 2003, Photo-Definable Self-Assembled Materials.
U.S. Appl. No. 09/389,085, filed Sep. 2, 1999, Low Frequency Feedback Speaker System.
U.S. Appl. No. 08/385,338, filed Feb. 8, 1995, Unidirectional Ring Laser Gyroscope.
U.S. Appl. No. 08/250,882 U.S. Pat. No. 5,438,585, filed May 31, 1994, Unstable Resonator Semiconductor Laser.
U.S. Appl. No. 16/500,349, filed Oct. 2, 2019, Porous Nanoparticle-Supported Lipid Bilayer Delivery of Transcriptional Gene Modulators.
U.S. Appl. No. 15/023,093, filed Mar. 18, 2016, Core and Surface Modification of Mesoporous Silica Nanoparticles to Achieve Cell Specific Targeting In Vivo.
U.S. Appl. No. 15/023,110 U.S. Pat. No. 9,855,217, filed Mar. 18, 2016, Toroidal Mesoporous Silica Nanoparticles (TMSNPS) and Related Protocells.
U.S. Appl. No. 15/858,923, filed Dec. 29, 2017, Toroidal Mesoporous Silica Nanoparticles (TMSNPS) and Related Protocells.
U.S. Appl. No. 14/350,674, filed May 20, 2014, Porous Nanoparticle-Supported Lipid Bilayers (Protocells) for Targeted Delivery Including Transdermal Delivery of Cargo and Methods Thereof.
U.S. Appl. No. 15/380,962, filed Dec. 15, 2016, Porous Nanoparticle-Supported Lipid Bilayers (Protocells) for Delivery Including Transdermal Delivery of Cargo and Methods Thereof.
U.S. Appl. No. 14/781,765, filed Nov. 23, 2015, Mesoporous Alum Nanoparticles as a Universal Platform for Antigen Adsorption, Presentation, and Delivery.
U.S. Appl. No. 12/909,572 U.S. Pat. No. 8,992,984, filed Oct. 21, 2010, Protocells and Their Use for Targeted Delivery of Multicomponent Cargos to Cancer Cells.
U.S. Appl. No. 14/627,739 U.S. Pat. No. 9,480,653, filed Feb. 20, 2015, Protocells and Their Use for Targeted Delivery of Multicomponent Cargos to Cancer Cells.
U.S. Appl. No. 14/797,487, filed Jul. 13, 2015, Protocells and Their Use for Targeted Delivery of Multicomponent Cargos to Cancer Cells.
U.S. Appl. No. 14/113,371 U.S. Pat. No. 9,579,283, filed Dec. 4, 2013, Porous Nanoparticle-Supported Lipid Bilayers (Protocells) for Targeted Delivery and Methods of Using Same.
U.S. Appl. No. 14/970,998 U.S. Pat. No. 10,022,327, filed Dec. 16, 2015, Porous Nanoparticle-Supported Lipid Bilayers (Protocells) for Targeted Delivery and Methods of Using Same.
U.S. Appl. No. 16/025,557, filed Jul. 2, 2018, Porous Nanoparticle-Supported Lipid Bilayers (Protocells) for Targeted Delivery and Methods of Using Same.
U.S. Appl. No. 14/781,817, filed Nov. 9, 2015, Antibiotic Protocells and Related Pharmaceutical Formulations and Methods of Treatment.
U.S. Appl. No. 15/474,800, filed Mar. 30, 2017, Protocells for Plasmid and RNP Delivery in the Treatment of Cancer and Other Disease States.
U.S. Appl. No. 15/474,810, filed Mar. 30, 2017, Carriers for Plasmid and RNP Delivery in the Treatment of Cancer and Other Disease States.

(56) References Cited

OTHER PUBLICATIONS

U.S. Appl. No. 14/369,741, filed Jun. 30, 2014, CRLF-2 Binding Peptides, Protocells and Viral-Like Particles Useful in the Treatment of Cancer, Including Acute Lymphoblastic Leukemia (ALL).
U.S. Appl. No. 15/788,634, filed Oct. 19, 2017, CRLF-2 Binding Peptides, Protocells And Viral-Like Particles Useful in the Treatment of Cancer, Including Acute Lymphoblastic Leukemia (ALL).
U.S. Appl. No. 13/143,164 U.S. Pat. No. 8,734,816, filed Jul. 1, 2011, Porous Nanoparticle Supported Lipid Bilayer Nanostructures.
U.S. Appl. No. 14/253,030, filed Apr. 15, 2014, Porous Nanoparticle Supported Lipid Nanostructures.
U.S. Appl. No. 15/557,368, filed Sep. 11, 2017, Generation of Mesoporous Materials Using Multiphase Surfactant Systems.
U.S. Appl. No. 12/903,577, filed Oct. 13, 2010, Protocells and Their Use for Pain Treatment.
U.S. Appl. No. 15/757,254, filed Mar. 2, 2018, Protocells to Treat Microbial Infection and for Synergistic Delivery.
U.S. Appl. No. 15/757,269, filed Mar. 2, 2018, Mesoporous Silica Nanoparticles and Supported Lipid Bi-Layer Nanoparticles for Biomedical Applications.
U.S. Appl. No. 16/828,137, filed Mar. 24, 2020, Mesoporous Silica Nanoparticles and Supported Lipid Bi-Layer Nanoparticles for Biomedical Applications.
U.S. Appl. No. 15/557,000, filed Sep. 8, 2017, CD 47 Containing Porous Nanoparticle Supported Lipid Bilayers (Protocells) Field of the Invention.
U.S. Appl. No. 16/068,235, filed Jul. 5, 2018, Osteotropic Nanoparticles for Prevention or Treatment of Bone Metastases.
U.S. Appl. No. 16/490,280 U.S. Pat. No. 11,344,629, filed Aug. 30, 2019, Active Targeting of Cells by Monosized Protocells.
U.S. Appl. No. 16/635,246, filed Jan. 30, 2020, Liposomal Coated Nanoparticles for Immunotherapy Applications.
U.S. Appl. No. 15/887,619, filed Feb. 2, 2018, Porous Nanoparticle-Supported Lipid Bilayers (Protocells) for Delivery Including Transdermal Delivery of Cargo and Methods Thereof.
U.S. Appl. No. 16/976,651, filed Aug. 28, 2020, Starry Mesoporous Silica Nanoparticles and Supported Lipid Bi-Layer Nanoparticles.
U.S. Appl. No. 17/264,452, filed Jan. 29, 2021, Biomimetic Rebuilding of Multifunctional Red Blood Cells.
U.S. Appl. No. 17/277,256, filed Mar. 17, 2021, Living Mammalian Cells Modified With Functional Modular Nanoparticles.
U.S. Appl. No. 17/277,260, filed Mar. 17, 2021, Armored Cells.
"U.S. Appl. No. 10/100,108, Non Final Office Action mailed Jan. 22, 2004", 8 pgs.
"U.S. Appl. No. 10/100,108, Notice of Allowance mailed Jul. 13, 2004", 10 pgs.
"U.S. Appl. No. 10/100,108, Response filed Apr. 21, 2004 to Non Final Office Action mailed Jan. 22, 2004", 9 pgs.
"U.S. Appl. No. 10/163,425, Advisory Action mailed Jul. 2, 2004".
"U.S. Appl. No. 10/163,425, Examiner Interview Summary filed Mar. 29, 2005", 9 pgs.
"U.S. Appl. No. 10/163,425, Final Office Action mailed Mar. 31, 2004", 8 pgs.
"U.S. Appl. No. 10/163,425, Non Final Office Action mailed Aug. 1, 2003", 10 pgs.
"U.S. Appl. No. 10/163,425, Non Final Office Action mailed Sep. 22, 2004", 6 pgs.
"U.S. Appl. No. 10/163,425, Notice of Allowance mailed Feb. 10, 2005", 8 pgs.
"U.S. Appl. No. 10/163,425, Response filed Jan. 2, 2004 to Non Final Office Action mailed Aug. 1, 2003", 13 pgs.
"U.S. Appl. No. 10/163,425, Response filed May 28, 2004 to Final Office Action mailed Mar. 31, 2004", 15 pgs.
"U.S. Appl. No. 10/163,425, Response filed Jul. 23, 2004 to Advisory Action mailed Jul. 2, 2004", 15 pgs.
"U.S. Appl. No. 10/163,425, Response filed Dec. 22, 2004 to Non Final Office Action mailed Sep. 22, 2004", 11 pgs.
"U.S. Appl. No. 10/373,565, Notice of Allowance mailed Sep. 11, 2007", 4 pgs.
"U.S. Appl. No. 12/903,577, Advisory Action mailed Mar. 20, 2012", 3 pgs.
"U.S. Appl. No. 12/903,577, Advisory Action mailed Jun. 7, 2017", 2 pgs.
"U.S. Appl. No. 12/903,577, Final Office Action mailed May 8, 2015", 19 pgs.
"U.S. Appl. No. 12/903,577, Final Office Action mailed Nov. 30, 2011", 19 pgs.
"U.S. Appl. No. 12/903,577, Non Final Office Action mailed Jun. 3, 2014", 16 pgs.
"U.S. Appl. No. 12/903,577, Non Final Office Action mailed Jun. 30, 2011", 13 pgs.
"U.S. Appl. No. 12/903,577, Non Final Office Action mailed Oct. 25, 2017", 16 pgs.
"U.S. Appl. No. 12/903,577, Notice of Non-Compliant Amendment mailed Feb. 4, 2015", 5 pgs.
"U.S. Appl. No. 12/903,577, Response filed Jan. 20, 2016 to Final Office Action mailed May 8, 2015", 7 pgs.
"U.S. Appl. No. 12/903,577, Response filed Feb. 26, 2015 to Notice of Non-Compliant Amendment mailed Feb. 4, 2015", 5 pgs.
"U.S. Appl. No. 12/903,577, Response filed Mar. 9, 2012 to Final Office Action mailed Nov. 30, 2011", 22 pgs.
"U.S. Appl. No. 12/903,577, Response filed Jun. 1, 2011 to Restriction Requirement mailed May 13, 2011", 2 pgs.
"U.S. Appl. No. 12/903,577, Response filed Jul. 12, 2017 to Advisory Action mailed Jul. 7, 2017", 7 pgs.
"U.S. Appl. No. 12/903,577, Response filed Sep. 30, 2011 to Non Final Office Action mailed Jun. 30, 2011", 9 pgs.
"U.S. Appl. No. 12/903,577, Response filed Dec. 3, 2014 to Non Final Office Action mailed Jun. 3, 2014", 15 pgs.
"U.S. Appl. No. 12/903,577, Restriction Requirement mailed May 13, 2011", 10 pgs.
"U.S. Appl. No. 13/143,164, 312 Amendment filed Mar. 27, 2014", 5 pgs.
"U.S. Appl. No. 13/143,164, Final Office Action mailed Jun. 26, 2013", 14 pgs.
"U.S. Appl. No. 13/143,164, Non Final Office Action mailed Jan. 11, 2013", 12 pgs.
"U.S. Appl. No. 13/143,164, Notice of Allowance mailed Jan. 13, 2014", 7 pgs.
"U.S. Appl. No. 13/143,164, Response filed Apr. 10, 2013 to Non Final Office Action mailed Jan. 11, 2013", 13 pgs.
"U.S. Appl. No. 13/143,164, Response filed Nov. 7, 2012 to Restriction Requirement mailed Oct. 10, 2012", 4 pgs.
"U.S. Appl. No. 13/143,164, Response filed Nov. 26, 2013 to Final Office Action mailed Jun. 26, 2013", 18 pgs.
"U.S. Appl. No. 13/143,164, Restriction Requirement mailed Oct. 10, 2012", 11 pgs.
"U.S. Appl. No. 14/113,371, 312 Amendment filed Dec. 21, 2016", 4 pgs.
"U.S. Appl. No. 14/113,371, Amendment filed Sep. 23, 2016", 16 pgs.
"U.S. Appl. No. 14/113,371, Examiner Interview Summary mailed Mar. 25, 2016", 1 pg.
"U.S. Appl. No. 14/113,371, Final Office Action mailed Feb. 1, 2016", 15 pgs.
"U.S. Appl. No. 14/113,371, Final Office Action mailed Mar. 25, 2016", 13 pgs.
"U.S. Appl. No. 14/113,371, Non Final Office Action mailed Jul. 13, 2015", 14 pgs.
"U.S. Appl. No. 14/113,371, Non Final Office Action mailed Dec. 17, 2014", 15 pgs.
"U.S. Appl. No. 14/113,371, Notice of Allowability mailed Jan. 31, 2017", 4 pgs.
"U.S. Appl. No. 14/113,371, Notice of Allowance mailed Oct. 11, 2016", 9 pgs.
"U.S. Appl. No. 14/113,371, Preliminary Amendment filed Oct. 22, 2013", 14 pgs.
"U.S. Appl. No. 14/113,371, Response filed Apr. 16, 2015 to Non Final Office Action mailed 12-17-1", 23 pgs.
"U.S. Appl. No. 14/113,371, Response filed Aug. 25, 2016 to Final Office Action mailed Mar. 25, 2016", 17 pgs.

(56) References Cited

OTHER PUBLICATIONS

"U.S. Appl. No. 14/113,371, Response filed Oct. 17, 2014 to Restriction Requirement mailed Aug. 18, 2014", 19 pgs.
"U.S. Appl. No. 14/113,371, Response filed Nov. 4, 2015 to Non Final Office Action mailed Jul. 13, 2015", 25 pgs.
"U.S. Appl. No. 14/113,371, Response filed Sep. 26, 2016 to Final Office Action mailed Mar. 25, 2016", 16 pgs.
"U.S. Appl. No. 14/113,371, Restriction Requirement mailed Aug. 18, 2014", 12 pgs.
"U.S. Appl. No. 14/253,030, Advisory Action mailed Apr. 11, 2018", 25 pgs.
"U.S. Appl. No. 14/253,030, Advisory Action mailed Sep. 5, 2017", 22 pgs.
"U.S. Appl. No. 14/253,030, Advisory Action mailed Sep. 9, 2016", 16 pgs.
"U.S. Appl. No. 14/253,030, Declaration under 37 C.F.R 1.132 filed Mar. 27, 2018", 4 pgs.
"U.S. Appl. No. 14/253,030, Final Office Action mailed May 11, 2016", 15 pgs.
"U.S. Appl. No. 14/253,030, Final Office Action mailed Jun. 9, 2017", 19 pgs.
"U.S. Appl. No. 14/253,030, Final Office Action mailed Dec. 1, 2017", 21 pgs.
"U.S. Appl. No. 14/253,030, Non Final Office Action mailed Dec. 9, 2016", 19 pgs.
"U.S. Appl. No. 14/253,030, Non Final Office Action mailed Dec. 10, 2015", 14 pgs.
"U.S. Appl. No. 14/253,030, Preliminary Amendment filed Jul. 1, 2015", 8 pgs.
"U.S. Appl. No. 14/253,030, Preliminary Amendment filed Dec. 9, 2014", 3 pgs.
"U.S. Appl. No. 14/253,030, Response filed Mar. 10, 2016 to Non Final Office Action mailed Dec. 10, 2015", 11 pgs.
"U.S. Appl. No. 14/253,030, Response filed Aug. 11, 2016 to Final Office Action mailed May 11, 2016", 9 pgs.
"U.S. Appl. No. 14/253,030, Response filed Oct. 10, 2017 to Advisory Action mailed Sep. 5, 2017", 12 pgs.
"U.S. Appl. No. 14/253,030, Response filed Oct. 11, 2016 to Advisory Action mailed Sep. 9, 2016", 9 pgs.
"U.S. Appl. No. 14/253,030, Response filed Nov. 2, 2015 to Restriction Requirement mailed Oct. 6, 2015", 4 pgs.
"U.S. Appl. No. 14/253,030, Response filed Apr. 2, 2018 to Final Office Action mailed Dec. 1, 2017", 10 pgs.
"U.S. Appl. No. 14/253,030, Response filed May 9, 2017 to Non-Final Office ACtion mailed Dec. 9, 2016", 8 pgs.
"U.S. Appl. No. 14/253,030, Response filed Aug. 10, 2017 to Final Office Action mailed Jun. 9, 2017", 12 pgs.
"U.S. Appl. No. 14/253,030, Restriction Requirement mailed Sep. 17, 2015", 7 pgs.
"U.S. Appl. No. 14/253,030, Restriction Requirement mailed Oct. 6, 2015", 7 pgs.
"U.S. Appl. No. 14/253,030, Supplemental Declaration under 37 C.F.R. 1.132 filed Aug. 7, 2017", 2 pgs.
"U.S. Appl. No. 14/350,674, Non Final Office Action mailed Jun. 17, 2016", 19 pgs.
"U.S. Appl. No. 14/350,674, Preliminary Amendment filed Jun. 4, 2015", 12 pgs.
"U.S. Appl. No. 14/350,674, Response filed May 16, 2016 to Restriction Requirement mailed Mar. 14, 2016", 10 pgs.
"U.S. Appl. No. 14/350,674, Restriction Requirement mailed Mar. 14, 2016", 12 pgs.
"U.S. Appl. No. 14/369,741, Final Office Action mailed Apr. 19, 2017", 10 pgs.
"U.S. Appl. No. 14/369,741, Non Final Office Action mailed Aug. 22, 2016", 17 pgs.
"U.S. Appl. No. 14/369,741, Non Final Office Action mailed Nov. 23, 2015", 11 pgs.
"U.S. Appl. No. 14/369,741, Preliminary Amendment filed Jun. 26, 2014", 16 pgs.
"U.S. Appl. No. 14/369,741, Response filed Mar. 23, 2016 to Non Final Office Action mailed Nov. 23, 2015", 12 pgs.
"U.S. Appl. No. 14/369,741, Response filed Sep. 14, 2015 to Restriction Requirement mailed May 14, 2015", 13 pgs.
"U.S. Appl. No. 14/369,741, Response filed Dec. 22, 2016 to Non-Final Office Action mailed Aug. 22, 2016", 12 pgs.
"U.S. Appl. No. 14/369,741, Restriction Requirement mailed May 14, 2015", 12 pgs.
"U.S. Appl. No. 14/627,739, Non Final Office Action mailed Jan. 29, 2016", 4 pgs.
"U.S. Appl. No. 14/627,739, Notice of Allowance mailed Jul. 6, 2016", 6 pgs.
"U.S. Appl. No. 14/627,739, Preliminary Amendment filed Feb. 20, 2015", 5 pgs.
"U.S. Appl. No. 14/627,739, Response filed Apr. 15, 2016 to Non Final Office Action mailed Jan. 29, 2016", 6 pgs.
"U.S. Appl. No. 14/627,739, Response filed Nov. 5, 2015 to Restriction Requirement mailed Aug. 6, 2015", 7 pgs.
"U.S. Appl. No. 14/627,739, Restriction Requirement mailed Aug. 6, 2015", 5 pgs.
"U.S. Appl. No. 14/781,765, Advisory Action mailed Jan. 29, 2019", 4 pgs.
"U.S. Appl. No. 14/781,765, Final Office Action mailed Aug. 28, 2018", 9 pgs.
"U.S. Appl. No. 14/781,765, Non Final Office Action mailed Feb. 15, 2018", 9 pgs.
"U.S. Appl. No. 14/781,765, Non Final Office Action mailed Jul. 15, 2019", 7 pgs.
"U.S. Appl. No. 14/781,765, Response filed Jan. 21, 2019 to Final Office Action mailed Aug. 28, 2018", 7 pgs.
"U.S. Appl. No. 14/781,765, Response filed Jun. 15, 2018 to Non Final Office Action mailed Feb. 15, 2018", 6 pgs.
"U.S. Appl. No. 14/781,765, Response filed Jan. 24, 2018 to Restriction Requirement mailed Aug. 24, 2017", 4 pgs.
"U.S. Appl. No. 14/781,765, Response filed Jan. 28, 2019 to Non-Final Office Action mailed Aug. 28, 2018", 7 pgs.
"U.S. Appl. No. 14/781,765, Restriction Requirement mailed Aug. 24, 2017", 6 pgs.
"U.S. Appl. No. 14/781,817, Preliminary Amendment filed Jan. 17, 2017", 5 pgs.
"U.S. Appl. No. 14/781,817, Restriction Requirement mailed Oct. 31, 2018", 9 pgs.
"U.S. Appl. No. 14/781,817, Supplemental Preliminary Amendment field Aug. 8, 2017", 9 pgs.
"U.S. Appl. No. 14/781,817, Supplemental Preliminary Amendment filed Jun. 27, 2017", 9 pgs.
"U.S. Appl. No. 14/797,487, Non Final Office Action mailed Jun. 14, 2017", 7 pgs.
"U.S. Appl. No. 14/797,487, Preliminary Amendment filed Jul. 24, 2015", 10 pgs.
"U.S. Appl. No. 14/797,487, Response filed Mar. 3, 2017 to Restriction Requirement mailed Jan. 3, 2017", 10 pgs.
"U.S. Appl. No. 14/797,487, Restriction Requirement mailed Jan. 3, 2017", 12 pgs.
"U.S. Appl. No. 14/970,998, Final Office Action mailed Sep. 27, 2017", 13 pgs.
"U.S. Appl. No. 14/970,998, Non Final Office Action mailed Apr. 6, 2017", 17 pgs.
"U.S. Appl. No. 14/970,998, Notice of Allowance mailed Mar. 16, 2018", 9 pgs.
"U.S. Appl. No. 14/970,998, Preliminary Amendment filed Dec. 16, 2015", 3 pgs.
"U.S. Appl. No. 14/970,998, Preliminary Amendment filed Dec. 28, 2015", 13 pgs.
"U.S. Appl. No. 14/970,998, Response filed Feb. 27, 2018 to Final Office Action mailed Sep. 27, 2017", 8 pgs.
"U.S. Appl. No. 14/970,998, Response filed Mar. 17, 2017 to Restriction Requirement mailed Jan. 19, 2017", 8 pgs.
"U.S. Appl. No. 14/970,998, Response filed Aug. 7, 2017 to Non-Final Office Action mailed Apr. 6, 2017", 13 pgs.
"U.S. Appl. No. 14/970,998, Restriction Requirement mailed Jan. 19, 2017", 8 pgs.

(56) References Cited

OTHER PUBLICATIONS

"U.S. Appl. No. 15/023,093 Response filed Feb. 3, 2017 to Restriction Requirement mailed Nov. 3, 2016", 12 pgs.
"U.S. Appl. No. 15/023,093, Non Final Office Action mailed Apr. 11, 2017", 12 pgs.
"U.S. Appl. No. 15/023,093, Preliminary Amendment filed Mar. 18, 2016", 3 pgs.
"U.S. Appl. No. 15/023,093, Restriction Requirement mailed Nov. 3, 2016", 10 pgs.
"U.S. Appl. No. 15/023,110, Corrected Notice of Allowance mailed Sep. 5, 2017", 8 pgs.
"U.S. Appl. No. 15/023,110, Non Final Office Action mailed Feb. 24, 2017", 10 pgs.
"U.S. Appl. No. 15/023,110, Notice of Allowance mailed Aug. 21, 2017", 11 pgs.
"U.S. Appl. No. 15/023,110, Preliminary Amendment filed Mar. 18, 2016", 3 pgs.
"U.S. Appl. No. 15/023,110, Preliminary Amendment filed Jul. 5, 2016", 7 pgs.
"U.S. Appl. No. 15/023,110, Response filed Jul. 24, 2017 to Non-Final Office Action mailed Feb. 24, 2017", 10 pgs.
"U.S. Appl. No. 15/380,962, Non Final Office Action mailed Aug. 2, 2017", 20 pgs.
"U.S. Appl. No. 15/380,962, Preliminary Amendment filed Dec. 15, 2016", 3 pgs.
"U.S. Appl. No. 15/380,962, Response filed Jul. 19, 2017 to Restriction Requirement mailed May 18, 2017", 9 pgs.
"U.S. Appl. No. 15/380,962, Restriction Requirement mailed May 18, 2017", 9 pgs.
"U.S. Appl. No. 15/474,800, Final Office Action mailed Mar. 8, 2019", 9 pgs.
"U.S. Appl. No. 15/474,800, Non Final Office Action mailed Oct. 18, 2018", 8 pgs.
"U.S. Appl. No. 15/474,800, Preliminary Amendment filed Jul. 19, 2017", 12 pgs.
"U.S. Appl. No. 15/474,800, Preliminary Amendment filed Oct. 10, 2017", 4 pgs.
"U.S. Appl. No. 15/474,800, Response filed Jan. 18, 2019 t Non-Final Office Action mailed Oct. 18, 2019", 11 pg.
"U.S. Appl. No. 15/474,800, Response filed Aug. 13, 2018 to Restriction Requirement mailed Mar. 12, 2018", 11 pgs.
"U.S. Appl. No. 15/474,800, Restriction Requirement mailed Mar. 12, 2018", 8 pgs.
"U.S. Appl. No. 15/474,810, Final Office Action mailed Mar. 8, 2019", 10 pgs.
"U.S. Appl. No. 15/474,810, Non Final Office Action mailed Sep. 20, 2018", 12 pgs.
"U.S. Appl. No. 15/474,810, Preliminary Amendment filed Jul. 18, 2017", 8 pgs.
"U.S. Appl. No. 15/474,810, Response filed Jan. 18, 2019 to Non-Final Office Action mailed Sep. 20, 2018", 8 pgs.
"U.S. Appl. No. 15/474,810, Response filed Aug. 7, 2018 to Restriction Requirement mailed Mar. 7, 2018", 8 pgs.
"U.S. Appl. No. 15/474,810, Restriction Requirement mailed Mar. 7, 2018", 8 pgs.
"U.S. Appl. No. 15/474,810. Supplemental Preliminary Amendment filed Oct. 30, 2017", 4 pgs.
"U.S. Appl. No. 15/557,000, Preliminary Amendment filed Sep. 8, 2017", 7 pgs.
"U.S. Appl. No. 15/557,000, Restriction Requirement mailed Mar. 11, 2019", 9 pgs.
"U.S. Appl. No. 15/557,368, Preliminary Amendment filed Sep. 11, 2017", 8 pgs.
"U.S. Appl. No. 15/557,368, Restriction Requirement mailed Feb. 15, 2019", 8 pgs.
"U.S. Appl. No. 15/757,254, Preliminary Amendment filed Mar. 2, 2018", 11 pgs.
"U.S. Appl. No. 15/757,254, Restriction Requirement mailed Sep. 16, 2019", 11 pgs.
"U.S. Appl. No. 15/757,269, Examiner Interview Summary mailed Jun. 25, 2019", 5 pgs.
"U.S. Appl. No. 15/757,269, Final Office Action mailed Oct. 25, 2019", 20 pgs.
"U.S. Appl. No. 15/757,269, Non Final Office Action mailed Apr. 12, 2019", 30 pgs.
"U.S. Appl. No. 15/757,269, Non Final Office Action mailed Dec. 4, 2018", 19 pgs.
"U.S. Appl. No. 15/757,269, Response filed Oct. 14, 2019 to Non-Final Office Action mailed Apr. 12, 2019", 10 pgs.
"U.S. Appl. No. 15/757,269, Response filed Mar. 28, 2019 to Non-Final Office Action mailed Dec. 4, 2018", 10 pgs.
"U.S. Appl. No. 16/025,557, Non Final Office Action mailed Feb. 6, 2020", 8 pgs.
"U.S. Appl. No. 16/025,557, Preliminary Amendment filed Jul. 2, 2018", 10 pgs.
"U.S. Appl. No. 16/068,235, Examiner Interview Summary mailed Apr. 5, 2021", 5 pgs.
"U.S. Appl. No. 16/068,235, Examiner's Amendment Communication mailed Mar. 16, 2022", U.S. Appl. No. 16/068,235, Examiner's, 20 pgs.
"U.S. Appl. No. 16/068,235, Non Final Office Action mailed May 13, 2020", 19 pgs.
"U.S. Appl. No. 16/068,235, Non Final Office Action mailed Jun. 15, 2021", 27 pgs.
"U.S. Appl. No. 16/068,235, Non Final Office Action mailed Aug. 25, 2020", 28 pgs.
"U.S. Appl. No. 16/068,235, Notice of Allowance mailed May 11, 2022", 27 pgs.
"U.S. Appl. No. 16/068,235, Notice of Non-Compliant Amendment mailed Apr. 6, 2021", 2 pgs.
"U.S. Appl. No. 16/068,235, Preliminary Amendment filed Jul. 5, 2018", 10 pgs.
"U.S. Appl. No. 16/068,235, Response filed Feb. 25, 2021 to Non Final Office Action mailed Aug. 25, 2020", 13 pgs.
"U.S. Appl. No. 16/068,235, Response filed May 1, 2020 to Restriction Requirement mailed Feb. 28, 2020", 9 pgs.
"U.S. Appl. No. 16/068,235, Response filed Jun. 7, 2021 to Notice of Non-Compliant Amendment mailed Apr. 6, 2021", 1 pg.
"U.S. Appl. No. 16/068,235, Response filed Aug. 13, 2020 to Non Final Office Action mailed May 13, 2020", 11 pgs.
"U.S. Appl. No. 16/068,235, Response filed Nov. 9, 2021 to Non Final Office Action mailed Jun. 15, 2021", 12 pgs.
"U.S. Appl. No. 16/068,235, Restriction Requirement mailed Feb. 28, 2020", 10 pgs.
"U.S. Appl. No. 16/068,235, Supplemental Preliminary Amendment filed Feb. 17, 2022", 11 pgs.
"U.S. Appl. No. 16/490,280, Advisory Action mailed Sep. 21, 2021", 3 pgs.
"U.S. Appl. No. 16/490,280, Final Office Action mailed May 13, 2021", 9 pgs.
"U.S. Appl. No. 16/490,280, Non Final Office Action mailed Nov. 13, 2020", 8 pgs.
"U.S. Appl. No. 16/490,280, Notice of Allowability mailed Feb. 9, 2022", 3 pgs.
"U.S. Appl. No. 16/490,280, Notice of Allowance mailed Jan. 28, 2022", 9 pgs.
"U.S. Appl. No. 16/490,280, Preliminary Amendment filed Aug. 30, 2019", 7 pgs.
"U.S. Appl. No. 16/490,280, Response filed Apr. 13, 2021 to Non Final Office Action mailed Nov. 13, 2020", 7 pgs.
"U.S. Appl. No. 16/490,280, Response filed Sep. 13, 2021 to Final Office Action mailed May 13, 2021", 9 pgs.
"U.S. Appl. No. 16/490,280, Response filed Sep. 28, 2020 to Restriction Requirement mailed Jul. 27, 2020", 7 pgs.
"U.S. Appl. No. 16/490,280, Restriction Requirement mailed Jul. 27, 2020", 8 pgs.
"U.S. Appl. No. 16/500,349, Preliminary Amendment filed Oct. 2, 2019", 7 pgs.
"U.S. Appl. No. 16/500,349, Restriction Requirement mailed Jun. 22, 2022", 9 pgs.
"U.S. Appl. No. 16/635,246, Non Final Office Action mailed May 31, 2022", 19 pgs.

(56) References Cited

OTHER PUBLICATIONS

"U.S. Appl. No. 16/635,246, Response filed Mar. 9, 2022 to Restriction Requirement mailed Feb. 17, 2022", 7 pgs.
"U.S. Appl. No. 16/635,246, Restriction Requirement mailed Feb. 17, 2022", 11 pgs.
"U.S. Appl. No. 16/635,246. Preliminary Amendment filed Jan. 30, 2020", 7 pgs.
"U.S. Appl. No. 16/828,137, Non Final Office Action mailed Jun. 15, 2021", 29 pgs.
"U.S. Appl. No. 16/828,137, Preliminary Amendment filed Mar. 24, 2020", 6 pgs.
"U.S. Appl. No. 16/828,137, Response filed Jun. 2, 2021 to Restriction Requirement mailed Apr. 2, 2021", 6 pgs.
"U.S. Appl. No. 16/828,137, Restriction Requirement mailed Apr. 2, 2021", 13 pgs.
"U.S. Appl. No. 16/976,651, Non Final Office Action mailed Jul. 19, 2022", 34 pgs.
"U.S. Appl. No. 16/976,651, Preliminary Amendment filed Aug. 28, 2020", 7 pgs.
"U.S. Appl. No. 16/976,651, Response filed Apr. 11, 2022 to Restriction Requirement mailed Mar. 9, 2022", 6 pgs.
"U.S. Appl. No. 16/976,651, Restriction Requirement mailed Mar. 9, 2022", 8 pgs.
"U.S. Appl. No. 17/264,452, Preliminary Amendment Filed Jan. 29, 2021", 6 pgs.
"U.S. Appl. No. 17/277,256, Preliminary Amendment filed Mar. 17, 2021", 7 pgs.
"U.S. Appl. No. 17/277,260, Preliminary Amendment filed Mar. 17, 2021", 7 pgs.
"U.S. Appl. No. 14/781,765, Preliminary Amendment filed Jul. 20, 2016", 6 pgs.
"U.S. Appl. No. 15/023,093, Preliminary Amendment filed Jun. 23, 2016", 11 pgs.
"U.S. Appl. No. 15/858,923, Preliminary Amendment filed Dec. 29, 2017", 7 pgs.
"Australian Application Serial No. 2012249474, First Examiner Report mailed Jul. 20, 2016", 4 pgs.
"Australian Application Serial No. 2012323937, First Examiner Report mailed Oct. 7, 2016", 5 pgs.
"Chinese Application Serial No. 201280031496.8, Decision on Rejection mailed Jun. 7, 2016", (English Translation), 9 pgs.
"Chinese Application Serial No. 201280061866.2, Office Action mailed Mar. 17, 2016", with English translation of claims, 23 pgs.
"European Application Serial No. 12776480.1, Extended European Search Report mailed Oct. 9, 2014", 8 pgs.
"European Application Serial No. 12776480.1, Response filed May 5, 2015 to Office Action mailed Oct. 28, 2014", 10 pgs.
"European Application Serial No. 12840155.1, Communication Pursuant to Article 94(3) EPC mailed Nov. 24, 2016", 5 pgs.
"European Application Serial No. 12840155.1, Extended European Search Report mailed May 28, 2015", 6 pgs.
"European Application Serial No. 14778464.9, Amendment filed Oct. 28, 2015", 18 pgs.
"European Application Serial No. 14778464.9, Extended European Search Report mailed Oct. 21, 2016", 8 pgs.
"European Application Serial No. 14778464.9, Response filed May 13, 2016 to Communication pursuant to Rules 161(2) and 162 EPC mailed Nov. 20, 2015", 17 pgs.
"European Application Serial No. 14779421.8, Extended European Search Report mailed Oct. 13, 2016", 11 pgs.
"European Application Serial No. 14779421.8, Response filed May 12, 2016 to Communication pursuant to Rules 161(2) and 162 EPC mailed Nov. 13, 2015", 21 pgs.
"European Application Serial No. 14845415.0, Response filed Nov. 2, 2016 to Communication pursuant to Rules 161(1) and 162 EPC mailed May 2, 2016", 9 pgs.
"European Application Serial No. 14846653.5, Extended European Search Report mailed Apr. 26, 2017", 9 pgs.
"European Application Serial No. 14846653.5, Response filed Nov. 2, 2016 to Communication pursuant to Rules 161(1) and 162 EPC mailed May 2, 2016", 37 pgs.
"International Application Serial No. PCT/US2014/056342, International Preliminary Report on Patentability mailed Mar. 22, 2016", 9 pgs.
"International Application Serial No. PCT/US2010/020096, International Preliminary Report on Patentability mailed Jul. 14, 2011", 5 pgs.
"International Application Serial No. PCT/US2010/020096, International Search Report mailed Sep. 17, 2010", 3 pgs.
"International Application Serial No. PCT/US2010/020096, Written Opinion mailed Sep. 17, 2010", 3 pgs.
"International Application Serial No. PCT/US2012/035529, International Preliminary Report on Patentability mailed Nov. 7, 2013", 8 pgs.
"International Application Serial No. PCT/US2012/035529, International Search Report mailed Oct. 23, 2012", 5 pgs.
"International Application Serial No. PCT/US2012/035529, Written Opinion mailed Oct. 23, 2012", 8 pgs.
"International Application Serial No. PCT/US2012/060072, International Preliminary Report on Patentability mailed Apr. 15, 2014", 10 pgs.
"International Application Serial No. PCT/US2012/060072, International Search Report mailed Mar. 28, 2013", 6 pgs.
"International Application Serial No. PCT/US2012/060072, Written Opinion mailed Mar. 28, 2013", 9 pgs.
"International Application Serial No. PCT/US2012/072297, International Preliminary Report on Patentability mailed Jul. 10, 2014", 13 pgs.
"International Application Serial No. PCT/US2012/072297, International Search Report mailed Jun. 2, 2013", 6 pgs.
"International Application Serial No. PCT/US2012/072297, Written Opinion mailed Jun. 2, 2013", 11 pgs.
"International Application Serial No. PCT/US2014/032702, International Preliminary Report on Patentability mailed Oct. 6, 2015", 10 pgs.
"International Application Serial No. PCT/US2014/032702, International Search Report mailed Aug. 26, 2014", 5 pgs.
"International Application Serial No. PCT/US2014/032702, Written Opinion mailed Aug. 26, 2014", 9 pgs.
"International Application Serial No. PCT/US2014/032711, International Preliminary Report on Patentability Oct. 6, 2015", 10 pgs.
"International Application Serial No. PCT/US2014/032711, International Search Report mailed Aug. 5, 2014", 5 pgs.
"International Application Serial No. PCT/US2014/032711, Written Opinion mailed Aug. 5, 2014", 9 pgs.
"International Application Serial No. PCT/US2014/056312, International Preliminary Report on Patentability mailed Mar. 31, 2016", 10 pgs.
"International Application Serial No. PCT/US2014/056312, International Search Report mailed Dec. 24, 2014", 5 pgs.
"International Application Serial No. PCT/US2014/056312, Written Opinion mailed Dec. 24, 2014", 8 pgs.
"International Application Serial No. PCT/US2014/056342, International Search Report mailed Dec. 23, 2014", 4 pgs.
"International Application Serial No. PCT/US2014/056342, Written Opinion mailed Dec. 23, 2014", 8 pgs.
"International Application Serial No. PCT/US2015/053244, International Preliminary Report on Patentability mailed Apr. 13, 2017", 10 pgs.
"International Application Serial No. PCT/US2015/053244, International Search Report mailed Feb. 4, 2016", 5 pgs.
"International Application Serial No. PCT/US2015/053244, Written Opinion mailed Feb. 4, 2016", 8 pgs.
"International Application Serial No. PCT/US2016/021490, International Preliminary Report on Patentability mailed Sep. 21, 2017", 7 pgs.
"International Application Serial No. PCT/US2016/021490, International Search Report mailed Jun. 30, 2016", 4 pgs.
"International Application Serial No. PCT/US2016/021490, Written Opinion mailed Jun. 30, 2016", 5 pgs.

(56) References Cited

OTHER PUBLICATIONS

"International Application Serial No. PCT/US2016/022056, International Preliminary Report on Patentability mailed Sep. 21, 2017", 7 pgs.
"International Application Serial No. PCT/US2016/022056, International Search Report mailed Jul. 7, 2016", 4 pgs.
"International Application Serial No. PCT/US2016/022056, Written Opinion mailed Jul. 7, 2016", 5 pgs.
"International Application Serial No. PCT/US2016/050259, International Preliminary Report on Patentability mailed Mar. 15, 2018", 10 pgs.
"International Application Serial No. PCT/US2016/050259, International Search Report mailed Dec. 15, 2016", 4 pgs.
"International Application Serial No. PCT/US2016/050259, Written Opinion mailed Dec. 15, 2016", 8 pgs.
"International Application Serial No. PCT/US2016/050260, International Preliminary Report on Patentability mailed Mar. 15, 2018", 8 pgs.
"International Application Serial No. PCT/US2016/050260, International Search Report mailed Dec. 22, 2016", 3 pgs.
"International Application Serial No. PCT/US2016/050260, Written Opinion mailed Dec. 22, 2016", 6 pgs.
"International Application Serial No. PCT/US2017/012583, International Preliminary Report on Patentability mailed Jul. 19, 2018", 7 pgs.
"International Application Serial No. PCT/US2017/012583, International Search Report mailed Apr. 20, 2017", 3 pgs.
"International Application Serial No. PCT/US2017/012583, Written Opinion mailed Apr. 20, 2017", 5 pgs.
"International Application Serial No. PCT/US2018/020496, International Preliminary Report on Patentability mailed Sep. 12, 2019", 6 pgs.
"International Application Serial No. PCT/US2018/020496, International Search Report mailed Jun. 14, 2018", 4 pgs.
"International Application Serial No. PCT/US2018/020496, Written Opinion mailed Jun. 14, 2018", 4 pgs.
"International Application Serial No. PCT/US2018/025830, International Preliminary Report on Patentability mailed Oct. 17, 2019", 9 pgs.
"International Application Serial No. PCT/US2018/025830, International Search Report mailed Aug. 2, 2018", 4 pgs.
"International Application Serial No. PCT/US2018/025830, Written Opinion mailed Aug. 2, 2018", 7 pgs.
"International Application Serial No. PCT/US2018/045218, International Preliminary Report on Patentability mailed Feb. 13, 2020", 7 pgs.
"International Application Serial No. PCT/US2018/045218, International Search Report mailed Nov. 29, 2018", 3 pgs.
"International Application Serial No. PCT/US2018/045218, Written Opinion mailed Nov. 29, 2018", 5 pgs.
"International Application Serial No. PCT/US2019/020084, International Preliminary Report on Patentability mailed Sep. 10, 2020", 7 pgs.
"International Application Serial No. PCT/US2019/020084, International Search Report mailed Jun. 6, 2019", 3 pgs.
"International Application Serial No. PCT/US2019/020084, Written Opinion mailed Jun. 6, 2019", 5 pgs.
"International Application Serial No. PCT/US2019/044107, International Preliminary Report on Patentability mailed Feb. 11, 2021", 6 pgs.
"International Application Serial No. PCT/US2019/044107, International Search Report mailed Nov. 14, 2019", 2 pgs.
"International Application Serial No. PCT/US2019/044107, Written Opinion mailed Nov. 14, 2019", 4 pgs.
"International Application Serial No. PCT/US2019/052658, International Preliminary Report on Patentability mailed Apr. 1, 2021", 6 pgs.
"International Application Serial No. PCT/US2019/052658, International Search Report mailed Mar. 12, 2020", 3 pgs.
"International Application Serial No. PCT/US2019/052658, Written Opinion mailed Mar. 12, 2020", 4 pgs.
"International Application Serial No. PCT/US2019/052669, International Preliminary Report on Patentability mailed Apr. 1, 2021", 7 pgs.
"International Application Serial No. PCT/US2019/052669, International Search Report mailed Jan. 9, 2020", 3 pgs.
"International Application Serial No. PCT/US2019/052669, Written Opinion mailed Jan. 9, 2020", 5 pgs.
"International Application Serial No. PCT/US2020/020066, International Preliminary Report on Patentability mailed Sep. 10, 2021", 6 pgs.
"Israel Application Serial No. 232025, Office Action mailed May 1, 2016", 2 pgs.
"Japanese Application Serial No. 2014-508125, Office Action mailed Feb. 15, 2016", with English translation of claims, 9 pgs.
"Japanese Application Serial No. 2014-508125, Written Amendment filed Apr. 27, 2015", with English translation, 29 pgs.
"Japanese Application Serial No. 2014-508125,, Decision on Refusal mailed Dec. 26, 2016", with English translation, 2 pgs.
"Japanese Application Serial No. 2014-535948, Office Action mailed Jun. 27, 2016", with machine translation, 16 pgs.
"Mexican Application Serial No. MX/a/2014/004415, Office Action mailed Apr. 19, 2018", with machine translation, 6 pgs.
"New Zealand Application Serial No. 624962, First Examiner Report mailed Feb. 9, 2016", 3 pgs.
"Russian Application Serial No. 2014119428, Office Action mailed Apr. 15, 2016", 2 pgs.
"Russian Application Serial No. 2014119428, Office Action mailed Apr. 21, 2017", with English Translation, 7 pgs.
"Singapore Application Serial No. 11201401499X, Office Action mailed Apr. 19, 2016", 11 pgs.
"Singapore Application Serial No. 11201401499X, Written Opinion mailed Oct. 5, 2015", 11 pgs.
Akazawa, Takashi, et al., "Development of a dendritic cell-targeting lipopeptide as an immunoadjuvant that inhibits tumor growth without inducing local inflammation", International Journal of Cancer, vol. 135, (2014), 2847-2856.
Ashley, et al., "(abstract) Development of a Virus-Like Particle that integrates Phage Display and Targeted delivery capabilities", MRS meeting, (2010), 1 pg.
Ashley, C E, et al., "Cell-Specific Delivery of Diverse Cargos by Bacteriophage MS2 Virus-like Particles", ACSNANO, 5(7), (2011), 1-26.
Ashley, C E, et al., "The targeted delivery of multicomponent cargos to cancer cells by nanoporous particle-supported lipid bilayers", Nature Materials, No. 5, vol. 10, (Apr. 17, 2011), 389-397.
Ashley, CE, et al., "Delivery of Small Interfering RNA by Peptide-Targeted Mesoporous Silica Nanoparticle-Supported Lipid Bilayers", ACS NANO, vol. 6, No. 3, (2012), 2174-2188.
Attard, George S, et al., "Liquid-crystalline phases as templates for the synthesis of mesoporous silica", Nature Publishing Group vol. 378, (Nov. 23, 1995), 3 pgs.
Aubin, R. A., et al., "Highly effective delivery of foreign DNA to adherent cells via polybrene/DMSO-assisted gene transfer", Methods Mol Biol., 62, (1997), 319-42.
Balas, Francisco, et al., "Confinement and Controlled Release of Bisphosphonates on Ordered Mesoporous Silica-Based Materials", Journal of the American Chemical Society, vol. 128, 2006, (2006), 8116-8117.
Bao, et al., "Targeted Gene Therapy of Ovarian Cancer using an Ovarian-Specific Promoter", Gynecologic Oncology, 84, (2002), 228-34.
Beckett, D, et al., "Roles of Operator and Non-operator RNA Sequences in Bacteriophage R17 Capsid Assembly", J Mol Biol, 204, (1988), 939-947.
Benneti, GJ, et al., "A peripheral mononeuropathy in rat that produces disorders of pain sensation like those seen in man", Pain, (1988), 87-107.
Bennett, Gary, et al., "A peripheral mononeuropathy in rat that produces disorders of pain sensation like those seen in man.", Pain, 33, (1988), 87-107.

(56) References Cited

OTHER PUBLICATIONS

Beteck, Richard, "Chemical and biochemical modification of mesoporous silicon for in vivo analysis.", Master's thesis, University of Eastern Finland, (2013), 8-9.
Brinker, C Jeffrey, et al., "Evaporation-Induced Self-Assembly: Nanostructures Made Easy", Advanced Materials, 11(7), (May 1999), 579-585.
Buranda, T, et al., "Biomimetic Molecular Assemblies on Glass and Mesoporous Silica Microbeads for Biotechnology", Langmuir, 19, (2003), 1654-1663.
Butler, Kimberly, et al., "Protocells: Modular Mesoporous Silica Nanoparticle-Supported Lipid Bilayers for Drug Delivery", Small 12, No. 16, (2016), 2173-2185.
Caldeira, J C, et al., "Stability and assembly in vitro of bacteriophage PP7 virus-like particles", Journal of Nanobiotechnology, 5, (2007), 1-13.
Carnes, E C, et al., "Confinement-induced quorum sensing of individual *Staphylococcus aureus* bacteria", Nature Chemical Biology, 6, (2010), 1-12.
Carnes, Eric C., et al., "Targeted Nanoporous Particle-Supported Lipid Bilayers for Treatment of Childhood Leukemia", (Jun. 2011), 1 pg.
Carroll, N J, et al., "Microparticles with Bimodal Nanoporosity Derived by Microemulsion Templating", Langmuir 25(23), (2009), 13540-13544.
Cartier, et al., "Utilization of synthetic peptides containing nuclear localization signals for nonviral gene transfer systems", Gene Therapy, 9, (2002), 157-67.
Chackerian, B, et al., "Peptide Epitope Identification by Affinity Selection on Bacteriophage MS2 Virus-Like Particles", J Mol Biol; 409, (2011), 1-18.
Chacur, M, et al., "A new model of sciatic inflammatory neuritis (SIN): induction of unilateral and bilateral mechanical allodynia following acute unilateral peri-sciatic immune activation in rats", Pain, 94, (2001), 231-244.
Chantal, Pichon, et al., "Mannosylated and Histidylated LPR Technology for Vaccination with Tumor Antigen mRNA", <https://link.springer.com/content/pdf/10.1007%2F978-1-62703-260-5_16.pdf>, (2013), 247-274.
Chedid, Georgeset, et al., "Recent Trends in Covalent and Metal Organic Frameworks for Biomedical Applications", Nanomaterials (Basel), 8(11)., (Nov. 7, 2018), 27 pgs.
Cheng, WWK, et al., "Expression and purification of two anti-CD19 single chain Fv fragments for targeting of liposomes to CD19-expressing cells", Biochimica et Biophysica Acta, 1768, (2007), 21-29.
Citorik, R J, et al., "Sequence-specific antimicrobials using efficiently delivered RNA-guided nucleases", Nature biotechnology, (Sep. 21, 2014), 13 pgs.
Clemens, Daniel L., et al., "Targeted Intracellular Delivery of Antituberculosis Drugs to Mycobacterium tuberculosis-Infected Macrophages via Functionalized Mesoporous Silica Nanoparticles", Antimicrobial Agents and Chemotherapy, (Feb. 2012), 2535-2545.
Cokol, M, et al., "Finding nuclear localization signals", EMBO Reports, 1(5), (2000), 1-17.
Crombez, Laurence, et al., "Targeting cyclin B1 through peptide-based delivery of siRNA prevents tumour growth", Nucleic Acids Res., vol. 37, No. 14, (2009), 4559-4569.
Dengler, Ellen C, et al., "Improvement of spinal non-viral IL-10 gene delivery by D-mannose as a transgene adjuvant to control chronic neuropathic pain", Journal of Neuroinflammation, (2014), 1-21.
Dengler, Ellen C., et al., "Mesoporous silica-supported lipid bilayers (protocells) for DAN cargo delivery to the spinal cord", Journal of Controlled Release 168, (2013), 209-224.
Dubertret, B, et al., "In Vivo Imaging of Quantum Dots Encapsulated in Phospholipid Micelles", Science, vol. 298, (Nov. 29, 2002), 1759-1762.
Einkolopiyan, N. S., "New Aspects of the Nucleophilic Opening of Epoxide Rings", Pure & Applied Chemistry, vol. 48, Perpmon Pross, 1976, (1976), 317-328.
Epler, et al., "Nanopourous-Supported Lipid Bilayer Nanocarriers For Treatment Of Childhood Leukemia", Materials Research Society, Symposium LL: Biometic Engineering of Micro-and Nanoparticles; LL6.11, (2011), 32 pgs.
Epler, K, et al., "Delivery of Ricin Toxin A-Chain by Peptide-Targeted mesoporous Silica Nanoparticle Supported Lipid Bilayers.", Advanced Healthcare Materials, (2012), 348-353.
Fan, H, et al., "Rapid prototyping of patterned functional nanostructures", Nature, 405(6782), (May 4, 2000), 56-60.
Fang, Aiping, et al., "Template-Free Formation of Monodisperse Doughnut-Shaped Silica Microparitcles by Droplet-Based Microfluidics", Chem. Mater, (2011), 4660-4662 pgs.
Feng, Pingyun, et al., "Control of Pore Sizes in Mesoporous Silica Templated by Liquid Crystals in Block Copolymer-Cosurfactant-Water Systems", Langmuir, vol. 16, No. 12,, (Mar. 24, 2000), 7 pgs.
Fishkis, M, et al., "Abstracts: 'Self organization of short peptides and simple amphiphiles into membranes' and 'Encapsulation of polynucleotide/polypeptide systems by membranes', from Steps Towards the Formation of a Protocell: The Possible Role of Short Peptides", Orig Life Evol Biosph, vol. 37, (2007), 543-545.
Fishkis, Maya, "Steps Towards the Formation of a Protocell: The Possible Role of Short Peptides", Orig Live Evol Biosph 37, (2007), 537-553.
Gamal, M M, et al., "Skin delivery of oestradiol from lipid vesicles: importance of liposome structure", Int. J. Pharm., vol. 204, No. 1-2, (2000), 159-169.
Gariepy, et al., "Vectorial Delivery of Macromolecules Into Cells Using Peptide-Based Vehicles", Trends in Biotechnology vol. 19, (2001), 21-28.
Giacomo, Dacarro, et al., "Monolayers of Polyethilenimine on Flat Glass: A Versatile Platform for Cations Coordination and Nanoparticle Grafting in the Preparation of Antibacterial Surfaces", Dalton Trans. 41, 2456, (Jan. 5, 2012), 8 pgs.
Gordon, Alan N., et al., "Recurrent Epithelial Ovarian Carcinoma: A Randomized Phase III Study of Pegylated Liposomal Doxorubicin Versus Topotecan", Journal of Clinical Oncology, 19(14), (2001), 3312-3322.
Guo, Jimin, et al., "Cancer vaccines from cryogenically silicified tumour cells functionalized with pathogen-associated molecular patterns", Nature Biomedical Engineering vol. 6, (Jan. 2022), 19-31.
Harvey, R C, et al., "Rearrangement of CRLF2 is associated with mutation of JAK kinases, alteration of IKZF1, Hispanic/Latino ethnicity, and a poor outcome in pediatric, B-progenitor acute lymphoblastic leukemia", Blood, 115(26), (2010), 5312-5321.
Hatakeyama, "A pH-sensitive fusogenic peptide facilitates endosomal escape and greatly enhances the gene silencing of siRNA-containing nanoparticles in vitro and in vivo", Journal of Controlled Release, 139(2), (Oct. 15, 2009), 127-132.
Hicks, Randall W, et al., "Nanoparticle Assembly of Mesoporous A100H (Boehmite)", Chemistry of Materials, vol. 15, No. 1, (Jan. 1, 2003), 78-82.
Hildebrand, et al., "Nanoscale control of silica morphology and three-dimensional structure during diatom cell wall formation", Mater. Res. vol. 21, No. 10, (2006), 2689-2698.
Hooker, J M, et al., "Interior Surface Modification of Bacteriophage MS2", J Am Chem Soc, 126, (2004), 3718-3719.
Huo, Qisheng, et al., "Surfactant Control of Phases in the Synthesis of Mesoporous Silica-Based Materials", Chem. Mater. 1996, 8, (Feb. 15, 1996), 14 pgs.
Ikari, Kenichi, et al., "Structural Control of Mesoporous Silica Nanoparticles in a Binary Surfactant System", Langmuir 22(2), (2006), 5 pgs.
Iskandar, Ferry, et al., "Control of the morphology of nanostructured particles prepared by the spray drying of nanopartilce sol", Journal of Colloid and Interface Science 265, (2003), 296-303.
Israelachvili, J N, et al., "Physical principles of membrane organization", Quarterly Reviews of Biophysics, vol. 13(2),, (1980), 121-200.

(56) References Cited

OTHER PUBLICATIONS

Jain, P T, et al., "Enhancement of liposomal gene delivery in human breast cancer cells by dimethyl sulfoxide", (Mar. 1998), 609-611.

Jain, R. K, "Barriers to drug delivery in Solid Tumors", Scientific American,.271 (1), (Jul. 1994), 58-65.

James, J Kobie, et al., "Transforming Growth Factor B Inhibits the Antigen-Presenting Functions and Antitumor Activity of Dendritic Cell Vaccines", Cancer Research, vol. 63, (Apr. 15, 2003), 1860-1864.

Jewett, M C, et al., "Mimicking the *Escherichia coli* Cytoplasmic Environment Activates Long-Lived and Efficient Cell-Free Protein Synthesis", Wiley InterScience, [Online] Retrieved from the internet: <www.interscience.wiley.com DOI: 10.1002/bit.20026>, (2004), 19-26.

Jillavenkatesa, A, "Particle Size Characterization", National Institute of Standards and Technology, Special Publication 960-1, (2001), 1-167.

Jinping, Lai, et al., "Versatile Fluorescence Resonance Energy Transfer-Based Mesoporous Silica Nanoparticles for Real-Time Monitoring of Drug Release", ACS Nano, vol. 7, No. 3, (2013), 2741-2750.

Kaczanowska, Sabina, et al., "TLR agonists: our best frenemy in cancer immunotherapy", Journal of leukocyte Biology, 93(6), (2013), 847-863.

Kennedy, E M, et al., "Inactivation of the Human Papilloma virus E6 or E7 Gene in Cervical Carcinoma Cells by Using a Bacterial CRISPR/Cas RNA-Guided Endonuclease", Journal of Virology, (Aug. 6, 2014), 12 pgs.

Kim, D M, "A highly efficient cell-free protein synthesis system from *Excherichia coli*", Eur J Biochem, 239, (1996), 881-886.

Kim, E, et al., "Iodine 125-labeled mesenchymal-epithelial transition factor binding peptide-click-cRGDyk heterodimer for glioma imaging", Cancer Science, vol. 102, No. 8, (2011), 1516-1521.

Konermann, S, et al., "Genome-scale transcriptional activation by an engineered CRISPR-Cas9 complex", Nature, 2015, vol. 517, 583-588.

Kun, Zhang, et al., "Facile Large-Scale Synthesis of Monodisperse Mesoporous Silica Nanospheres with Tunable Pore Structure (Supporting Information)", Journal of the American Chemical Society, vol. 135,, (2013), 16 pgs.

Kunkel, T. A., "Rapid and Efficient Site-Specific Mutagenesis Without Phenotypic Selection", Proc. Natl. Acad. Sci. USA, 82, (1985), 488-492.

Lacasse, E C, et al., "Nuclear localization signals overlap DNA- or RNA-binding domains in nucleic acid-binding proteins", Nucleic Acids Research, 23(10), (1995), 1647-1656.

Li, Z, et al., "Mesoporous Silica Nanoparticles in Biomedical Applications", Chemical Society Reviews 41, (2012), 2590-2605.

Lim, F, et al., "RNA recognition site of PP7 coat protein", Nucleic Acids Research, 30(19), (2002), 4138-4144.

Lin, Xiong, et al., "Tunable stellate mesoporous silica nanoparticles for intracellular drug delivery", Journal of Materials Chemistry B, vol. 3, (2015), 1712-1721.

Lingxiang, Wu, et al., "Synthesis of a Zwitterionic Silane and Its Application in the Surface Modification of Silicon-Based Material Surfaces for Improved Hemocompatibility", ACS Applied Materials & Interfaces, vol. 2 No. 10, (2010), 2781-2788.

Liu, J, et al., "Electrostatically Mediated Liposome Fusion and Lipid Exchange with a Nanoparticle-Supported Bilayer for Control of Surface Charge, Drug Containment, and Delivery.", J Am Chem Soc, 131, (2009), 7567-7569.

Liu, Juewen, et al., "Porous Nanoparticle Supported Lipid Bilayers (Protocells) as Delivery Vehicles", J. Am. Chem. Soc., vol. 131, No. 4, (2009), 7 pgs.

Liu, Juewen, et al., "Silica nanoparticle supported lipid bilayers for gene delivery.", Chem Commun, (2009), 5100-5102.

Liu, Xiangsheng, et al., "Irinotecan Delivery by Lipid-Coated Mesoporous Silica Nanoparticles Shows Improved Efficacy and Safety over Liposomes for Pancreatic Cancer", ACS Nano 10, (2016), 2702-2715.

Lo, et al., "Hepatocellular Carcinoma Cell-Specific Peptide Ligand For Targeted Drug Delivery", Molecular Cancer Therapeutics 7(3), (2008), 579-589.

Lu, Weigang, et al., "Tuning the structure and function of metal-organic frameworks via linker design", Chemical Society Reviews, 43, (2014), 5561-5593.

Lu, Y, et al., "Aerosol-assisted self-assembly of mesostructured spherical nanoparticles", Nature, 398, (1999), 223-226.

Lu, Yunfeng, et al., "Continuous formation of supported cubic and hexagonal mesoporous films by sol-gel-dip-coating", Nature, 389(6649), (Sep. 25, 1997), 364-368.

Lu, Yunfeng, et al., "Evaporation-Induced Self-Assembly of Hybrid Bridged Silsesquioxane Film and Particulat Mesophases With Integral Organic Functionalitiy", Journal of the American Chemical Society, 122(22), (Jun. 1, 2000), 5258-5261.

Maghraby, EL, et al., "Interactions of surfactants (edge activators) and skin penetration enhancers with liposomes", Int. J. Pharm., vol. 276, No. 1-2, (2004), 143-161.

Mamaeva, Veronika, et al., "Mesoporous silica nanoparticles in medicine-Recent adva", Advanced Drug Delivery Reviews, Elsevier, Amsterdam, NL, vol. 65, No. 5, (Aug. 18, 2012), 689-702.

Mao, A, et al., "Deterministic encapsulation of single cells in thin tunable microgels for niche modeling and therapeutic delivery", Nat Mater 16, pp. 236-243, (2017), 21 pgs.

Martin, Kreutz, et al., "Targeting dendritic cells—why bother?", Blood, vol. 121, No. 15, (Apr. 11, 2013), 2836-2844.

Matteo, Porotto, et al., "Synthetic protocells interact with viral nanomachinery and inactivate pathogenic human virus", Plos One, val. 6, No. 3, (Mar. 1, 2011), 16874 pgs.

McDonald, Michael, "Functioning Nanostructures Self-Assemble Out of Ink", Posted May 8, 2000, http://www.amtexpo.com/nano/messages/255.html, (May 8, 2000), 3 pgs.

Meng, Huan, et al., "Co-delivery of an Optimal Drug/siRNA Combination Using Mesoporous Silica Nanoparticle to Overcome Drug Resistance in Breast Cancer In Vitro and In Vivo", ACS Nano., (2013), 1-21.

Meng, Huan, et al., "Two-Wave Nanotherapy To Target the Stroma and Optimize Gemcitabine Delivery To a Human Pancreatic Cancer Model in Mice", ACS Nano vol. 7 ' No. 11, (2013), 10048-10065.

Meng, Huan, et al., "Use of a Lipid-Coated Mesoporous Silica Nanoparticle Platform for Synergistic Gemcitabine and Paclitaxel Delivery to Human Pancreatic Cancer in Mice", ACS Nano, vol. 9, No. 4, (2015), 3540-3557.

Meng, Huan, et al., "Use of Size and a Co-polymer Design Feature to Improve the Biodistribution and the Enhanced Permeability and Retention Effect of Doxorubicin-loaded Mesoporous Silica Nanoparticles in a Murine Xenograft Tumor Model", ACS Nano, (2011), 32 pgs.

Midoux, P, et al., "Membrane Permeabilization and Efficient Gene Transfer by a Peptide Containing Several Histidines", Bioconjugate Chem, 9, (1998), 260-267.

Milligan, Ed, et al., "Pathological and protective roles of glia in chronic pain.", Nature Reviews Neuroscience, 10, (2009), 23-36.

Milligan, Ed, et al., "Thermal hyperalgesia and mechanical allodynia produced by intrathecal administration of the human immunodeficiency virus-1 (HIV-1) envelope glycoprotein, gp 120.", Brain Research, 861, (2000), 105-116.

Milligan, Erin, et al., "Intrathecal polymer-based interleukin-10 gene delivery for neuropathic pain", Neuron Glia Biology 2, (2007), 1-16.

Moller, K, et al., "Highly efficient siRNA delivery from core-shell mesoporous silica nanoparticles with multifunctional polymer caps", Nanoscale, 8, (2016), 13 pgs.

Mornet, et al., "The Formation of Support Lipid Bilayers on Silica Nanoparticles Revealed by Cryoelectron Microscopy", NanoLetters 5(2), (2005), 281-285.

Mungall, Bruce, et al., "Inhibition of Henipavirus infection by RNA interference", Antiviral Res., vol. 80, No. 3, (2008), 324-331.

Nakamura, Takashi, et al., "Nanoparticulation of BCG-CWS for application to bladder cancer therapy", Journal of Controlled Release vol. 176, (2014), 44-53.

(56) References Cited

OTHER PUBLICATIONS

Nekhotiaeva, Natalia, et al., "Inhibition of *Staphylococcus aureus* gene expression and growth using antisense peptide nucleic acids", Molecular Therapy, vol. 10, No. 4, (2004), 652-659.
Nikolic, M, et al., "Synthesis and characterization of mesoporous silica core-shell particles", Processing and Application of Ceramics, 4(2), (2010), 81-85.
Park, J, et al., "Cell-in-Shell Hybrids: Chemical Nanoencapsulation of Individual Cells", Acc. Chem. Res., 49(5), (2016), 792-800.
Pastan, I, et al., "Immunotoxin therapy of cancer.", Nature Reviews 6, (2006), 559-565.
Peabody, D S, "A Viral Platform for Chemical Modification and Multivalent Display", Journal of Nanobiotechnology, 1, (2003), 1-8.
Peabody, D S, et al., "Immunogenic Display of Diverse Peptides on Virus-like Particles of RNA Phage MS2", J Mol Biol, 380, (2008), 1-18.
Peabody, D S, "Translational Repression by Bacteriophage MS2 Coat Protein Expressed from a Plasmid", The Journal of Biological Chemistry; 265(10), (1990), 5684-5689.
Pickett, G G, et al., "Encapsidation of heterologous RNAs by bacteriophage MS2 coat protein", Nucleic Acids Research, 21(19), (1993), 4621-4626.
Pignatello, Rosario, et al., "A novel biomaterial for osteotropic drug nanocarriers; synthesis and biocompatibility evaliation of a PLGA-ALE conjugate.", Nanomedicine, vol. 4(2), 2009, (2009), 161-175.
PN, Durfee, et al., "Mesoporous Silica Nanoparticle-Supported Lipid Bilayers (Protocells) for Active Targeting and Delivery to Individual Leukemia Cells", ACS Nano, vol. 10, (2016), 8325-8345.
Porotto, M, et al., "Synthetic Protocells Interact with Viral Nano machinery and Inactivate Pathogenic Human Virus", (2011), 1-9 pgs.
Prokop, Ales, "Intracellular Delivery Fundamentals and Applications", ISBN Springer, (2011), 1-867.
Rao, G.V. R, et al., "Monodisperse Mesoporous Silica Microspheres Formed by Evaporation-Induced Self Assembly of Surfactant Templates in Aerosols", Adv. Mater, 14, No. 18, (Sep. 16, 2002), 1301-1304.
Raskopf, et al., "siRNA Targeting Vegf Inhibits Hepatocellular Carcinoma Growth And Tumor Angiogenesis In Vivo", Journal of Heptaology 49, (2008), 977-984.
Ricco, R, et al., "Metal-Organic Frameworks for Cell and Virus Biology: A Perspective", ACS Nano, 12, (Jan. 8, 2018), 13-23.
Rocca, F D, et al., "Cell Composition of the Human Pulmonary Valve: A Comparative Study with the Aortic Valve—The VESALIO* Project", Ann Thorac Surg. 70, (2000), 1594-1600.
Rodriguez, et al., "Minimal Self' Peptides That Inhibit Phagocytic Clearance and Enhance Delivery of Nano particles", (2013), 971-975 pgs.
Rodriguez, F, et al., "DNA Immunization: Ubiquitination of a Viral Protein Enhances Cytotoxic T-Lymphocyte Induction and Antiviral Protection but Abrogates Antibody Induction", Journal of Virology, vol. 7 No. 11, (Nov. 1997), 8497-8503.
Rosenholm, Jessica M, et al., "Towards multifunctional, targeted drug delivery systems using mesoporous silica nanoparticles— opportunities", Nanoscale, vol. 2, No. 10, (Jan. 1, 2010), 1870-1883.
Russell, R G, et al., "Bisphosphonates: An Update on Mechanisms of Action and How These Relate to Clinical Efficacy", Ann NY Acad Sci 1117, (2007), 209-257.
Ryther, RCC, et al., "siRNA therapeutics: big potential from small RNAs", Gene Therapy, vol. 12, (2005), 5-11.
Sanjana, N E, et al., "Improved vectors and genome-wide libraries for CRISPR screening", Nat Methods, (2014), 783-784.
Sapra P, Allen TM, et al., "Internalizing Antibodies are Necessary for Improved Therapeutic Efficacy of Antibody-targeted Liposomal Drugs.", Cancer Res 62, (2002), 7190-7194.
Schiller, Renate, et al., "Synthesis of Mesoporous Silica Particles and Capsules by Miniemulsion Technique", Chem. Mater. 2009, 21, (Sep. 23, 2009), 11 pgs.

Seo, Seog-Jin, et al., "Gene delivery techniques for adult stem cell-based regenerative therapy", Nanomedicine, vol. 8, No. 11, (2013), 2 pgs.
Shiraishi, T., et al., "Photochemically enhanced cellular delivery of cell penetrating peptide-PNA conjugates.", FEBS Letters, 580(5), (2006), 1451-1456.
Shou-Cang, Shen, et al., "Mesoporous silica nanoparticle-functionalized poly(methylmethacrylate)-based bone cement for effective antibiotics delivery", Journal of Materials Science: Materials in Medicine, Kluwer Academic Publishers, BO, vol. 22, No. 10, (Jul. 24, 2011), 2283-2292.
Sloane, E, et al., "Chronic constriction injury induced pathological pain states are controlled long term via intrathecal administration of a non-viral vector (NW) encoding the anti-inflammatory cylokine interleukin-10 (IL-10).", Second Joint Scientific Meeting of the American Pain Society and the Canadian Pain Society. Churchill Livingstone., (2004), p. 15.
Sloane, E, et al., "Immunological priming potentiates non-viral anti-inflammatory gene therapy treatment of neuropathic pain.", Gene Therapy, 16, (2009), 1210-1222.
Slowing, I I, et al., "(Abstract) Mesoporous silica nanoparticles as Controlled release drug delivery and gene transfection carriers", Advanced Drug Delivery Reviews vol. 60, Issue 11, (2008), 1278-1288.
Smothers, J F, et al., "Affinity Selection from Biological Libraries", Science, 298, (2002), 621-622.
Socorro, Espuelas, et al., "Influence of Ligand Valency on the Targeting of Immature Human Dendritic Cells by Mannosylated Liposomes", Bioconjugate Chemistry, vol. 19, (2008), 2385-2393.
Soderquist, et al., "Microparticle-mediated delivery of interleukin-1 0 plasmid DNA for the treatment of neuropathic pain", Poster Abstract No. 206d, (May 2008), 2 pgs.
Soderquist, R., et al., "Release of Plasmid DNA-Encoding IL-10 from PLGA Microparticles Facilitates Long-Term Reversal of Neuropathic Pain Following a Single Intrathecal Administration.", Pharmaceutical Research, (2010), 841-854.
Sorensen, Malin, "Mesostructured particulate silica materials with tunable pore size", Doctoral Thesis at the Royal Institute of Technology. Stockholm, Sweden,, (2009), 19-21.
Stemmer, WPC, et al., "Single-step assembly of a gene and entire plasmid from large numbers of oligodeoxyribonucleotides", Gene, 164, (1995), 49-53.
Suteewong, T, et al., "(Abstract) Synthesis and formation mechanism of aminated mesoporous silica nanoparticles", Chemistry of Materials, 24, (2012), 1 pg.
Suteewong, T, et al., "Highly aminated mesoporous silica nanoparticles with cubic pore structure", Journal of the American Chemical Society, 133(2), (2011), 172-175.
Takeuchi, S, "An Axisymmetric Flow-Focusing Microfluidic Device", Adv Mater, 17:8, (2005), 1067-1072.
Tarn, D, et al., "Mesoporous Silica Nanoparticle Nanocarriers: Biofunctionality and Biocompatibility.", Accounts of Chemical Research, (2013), 792-801.
Tatusova, T A, et al., "BLAST 2 Sequences, a new tool for comparing protein and nucleotide sequences", FEMS Microbiology Letters, 174, (1999), 247-250.
Tawfik, D S, et al., "Man-made cell-like compartments for molecular evolution", Nature Biotechnology; 16, (1998), 652-656.
Tejinder, Singh, et al., "The critical role of bisphosphonates to target bone cancer metastasis: an overview", Journal of Drug Targeting, vol. 23, (Sep. 9, 2014), 1-15.
Tianyi, Wang, et al., "Enhanced mucosal and systemic immune responses obtained by porous silica nanoparticles used as an oral vaccine adjuvant: Effect of silica architecture on immunological properties", International Journal of Pharmaceutics, vol. 436, No. 1-2, (Oct. 1, 2012), 351-358.
Torchilin, VP, et al., "Recent Advances with Liposomes as Pharmaceutical Carriers.", Nature Reviews, vol. 4, (2005), 145-159.
Townson, Jason L, et al., "Re-examining the Size/Charge Paradigm: Differing in Vivo Characteristics of Size- and Charge-Matched Mesoporous Silica Nanoparticles", J Am Chem Soc 135(43), (Oct. 30, 2013), 4 pgs.

(56) References Cited

OTHER PUBLICATIONS

Tran, Chris, et al., "Development of a second-generation antiandrogen for treatment of advanced prostate cancer", Science 324(5928), (2009), 787-790.
Uhlenbeck, O C, "A coat for all sequences", Nature structural biology, 5(3), (1998), 174-176.
Videira, et al., "Lymphatic uptake of lipid nanoparticles following endotracheal administration", Journal of Microencapsulation: Micro and Nano Carriers, 23(8), (2006), 855-862.
Villegas, et al., "Hybrid Collagenase Nanocapsules for Enhanced Nanocarrier Penetration in Tumoral Tissues", ACS Appl. Mater. Interfaces vol. 7, (2015), 24075-24081.
Vingerhoeds, et al., "Immunoliposome-mediated targeting of doxorubicin to human ovarian carcinoma in vitro and in vivo", British Journal of Cancer, (1996), 1023-29.
Wang, G, "Bisphosphonate-decorated lipid nanoparticles designed as drug carriers for bone diseases", Journal of Biomedical Materials Research A, vol. 100A, (Dec. 30, 2011), 684-693.
Wang, L-S, et al., "Biofunctionalized Phospholipid-Capped Mesoporous Silica Nanoshuttles for Targeted Drug Delivery: Improved Water Suspensibility and Decreased", ACS Nano, vol. 4 No. 8, (2010), 4371-4379.
Wang, Qingmin, et al., "Improved Cellular Immune Response Elicited by a Ubiquitin-Fused DNA Vaccine Against Mycobacterium tuberculosis", DNA and Cell Biology, vol. 31, No. 4, (2012), 489-495.
Wani, Amit, et al., "Surface Functionalization of Mesoporous Silica Nanoparticles Controls Loading and Release Behavior of Mitoxantrone", Pharmaceutical Research, Kluwer Academic Publishers-Plenum Publishers, NL, vol. 29, No. 9, (May 4, 2012), 2407-2418.
Weis, K, "Importins and exportins: how to get in and out of the nucleus", TIBS, 23, (1998), 185-189.
Wenyi, Gu, et al., "Nanotechnology in the targeted drug delivery for bone diseases and bone regeneration", International Journal of Nanomedicine, vol. 8, (2013), 2305-2317.
Wu, M, et al., "Cell-specific Delivery of Bacteriophage-Encapsidated Ricin A Chain", Bioconjugate Chem, 6, (1992), 587-595.
Xia, Tian, et al., "Polyethyleneimine Coating Enhances the Cellular Uptake of Mesoporous Silica Nanoparticles and Allows Safe Delivery of siRNA and DNA Constructs", ACS Nano; 3(10), (Oct. 27, 2009), 25 pgs.
Yamamoto, Satoshi, et al., "Synthesis of Fe70Pd30 nanoparticles and their surface modification by zwitterionic linker", Materials Chemistry and Physics 234, (2019), 237-244.
Yao, Sun, et al., "Stimuli-Responsive Shapeshifting Mesoporous Silica Nanoparticles", Nano Letters, vol. 16, (2016), 651-655.
Yao, Sun, et al., "Stimuli-Responsive Shapeshifting Mesoporous Silica Nanoparticles (Supporting Information)", Nano Letters, vol. 1, of supporting information, (2016), 1-11.
Yazdi, I, et al., "Novel mesoporous silicon particles as an efficient sustained delivery system for antibiotics", NSTI-Nanotech 2010, [Online] Retrieved from the Internet: <https://www.researchgate.net/profile/Iman_Yazdi/publication/290613308_Novel_mesaporous_silicon_particles_as_an_efficient_sustained_delivery_system-for antibiotics/links>, (Jan. 1, 2010), 324-325.
Youn, W, et al., "(Abstract) Cytoprotective Encapsulation of Individual Jurkat T Cells within Durable TiO2 Shells for T-Cell Therapy", Angew. Chem. Int. Ed., 56(36), pp. 10702-10706, (2017), 1 pg.
Yu-Shen, Lin, et al., "Well-Ordered Mesoporous Silica Nanoparticles as Cell Markers", Chem. Mater, 17, (2005), 4570-4573.
Zapryanova, et al., "Toroidal Microporous Silica Gel", Journal of Materials Science 14, (1979), 1175-1178 pgs.
Zelphati, et al., "Mechanism of Oligonucleotide Release from Cationic Liposomes", Proceedings of the National Academy of Sciences USA 93, (1996), 11493-98.
Zhang, Haiyuan, et al., "Differential Expression of Syndecan-1 Mediates Cationic Nanoparticle Toxicity in Undifferentiated versus Differentiated Normal Human Bronchial Epithelial Cells", ACS Nano, (2011), 1-29.
Zhang, Jing, et al., "Multifunctional Envelope-Type Mesoporous Silica Nanoparticles for Tumor-Triggered Targeting Drug Delivery", J. Am. Chem. Soc, 135 (13), (2013), 5068-5073.
Zhang, K, et al., "Facile Large-Scale Synthesis of Monodisperse Mesoporous Silica Nanospheres with Tunable Pore Structure", Journal of the American Chemical Society, (2013), 2427-2430.
Zhu, Kelong, et al., "Metal-Organic Frameworks with Mechanically Interlocked Pillars: Controlling Ring Dynamics in the Solid-State via a Reversible Phase Change", J Am Chem Soc. 136(20), (May 21, 2014), 7403-7409.
"U.S. Appl. No. 16/635,246, Final Office Action mailed May 13, 2024", 28 pgs.
"U.S. Appl. No. 16/635,246, Response filed May 1, 2024 to Non Final Office Action mailed Nov. 1, 2023", 7 pgs.
"U.S. Appl. No. 16/976,651, Non Final Office Action mailed Feb. 7, 2024", 31 pgs.
"U.S. Appl. No. 16/976,651, Response filed Jan. 29, 2024 to Final Office Action mailed Jul. 27, 2023", 12 pgs.
"U.S. Appl. No. 17/264,452, Restriction Requirement mailed Mar. 22, 2024", 12 pgs.
"U.S. Appl. No. 17/277,256, Non Final Office Action mailed Apr. 11, 2024", 24 pgs.
"U.S. Appl. No. 17/277,256, Response filed Feb. 20, 2024 to Restriction Requirement mailed Dec. 27, 2023", 6 pgs.
"U.S. Appl. No. 17/277,256, Restriction Requirement mailed Dec. 27, 2023", 10 pgs.
"U.S. Appl. No. 17/277,260, Non Final Office Action mailed Mar. 14, 2024", 27 pgs.
"U.S. Appl. No. 17/277,260, Response filed Jan. 22, 2024 to Restriction Requirement mailed Nov. 20, 2023", 6 pgs.
"U.S. Appl. No. 17/277,260, Response filed Jun. 11, 2024 to Non Final Office Action mailed Mar. 14, 2024", 15 pgs.
Allen, Theresa M, et al., "Use of the Post-Insertion Method for the Formation of Ligand-Coupled Liposomes", Cell & Molecular Biology Letters, vol. 7, (2022), 889-894.
Clem, Paul, et al., "Biomolecular Materials Meeting", pp. 13-19, [Online] Retrieved from the internet: <//efaidnbmnnnibpcajpcglclefindmkaj/https://science.osti.gov/-/media/bes/mse/pdf/docs/Materials-Discovery-Design-and-Synthesis-Team/2015_Biomolecular_Materials_PI_Meeting_abstracts_book.pdf>, (2015), 272 pgs.
Lee, et al., "Cytoprotective silica coating of individual mammalian cells through bioinspired silicification", Angewandte Chemie International Edition 53.31, https://onlinelibrary.wiley.com/doi/10.1002/anie.201402280, (2014), 8056-8059.
Lu, et al., "Nanoscale metal-organic frameworks for therapeutic, imaging, and sensing applications", Advanced Materials, 30, (2018), 20 pgs.
Park, et al., "Artificial spores: immunoprotective nanocoating of red blood cells with supramolecular ferric ion-tannic acid comple", Polymers 9.4: 140, (2017), 10 pgs.
Rabinowitz, Harold, et al., "The Manual of Scientific Style: A Guide for Authors, Editors, and Researchers", 1st ed. San Diego, CA, USA: Elsevier Science, Chapter 3—Elements of Style and Usage, (2009), 131-260.
Yang, et al., "Coating process and stability of metal-polyphenol film", Colloids and Surfaces A: Physicochem. Eng. Aspects 484, (2015), 197-205.
"U.S. Appl. No. 17/264,452, Response filed Jun. 24, 2024 to Restriction Requirement mailed Mar. 22, 2024", 7 pgs.
"International Application Serial No. PCT US2024 017524, International Search Report mailed Jul. 3, 2024", 5 pgs.
"International Application Serial No. PCT US2024 017524, Written Opinion mailed Jul. 3, 2024", 5 pgs.
"U.S. Appl. No. 17/277,256, Response filed Jul. 10, 2024 to Non Final Office Action mailed Apr. 11, 2024", 14 pgs.
"U.S. Appl. No. 18/834,513, Preliminary Amendment filed Jul. 30, 2024", 9 pgs.
"International Application Serial No. PCT US2023 061675, International Preliminary Report on Patentability mailed Aug. 15, 2024", 8 pgs.

* cited by examiner

MODULAR METAL-ORGANIC POLYHEDRA SUPERASSEMBLY COMPOSITIONS

CROSS-REFERENCE TO RELATED APPLICATIONS

This application is a U.S. National Stage Filing under 35 U.S.C. 371 from International Application No. PCT/US2020/020066, filed on Feb. 27, 2020, and published as WO 2020/176716 on Sep. 3, 2020, which application claims the benefit of the filing date of U.S. application No. 62/811,668, filed on Feb. 28, 2019, the disclosures of which are incorporated by reference herein.

STATEMENT OF GOVERNMENT RIGHTS

This invention was made with government support under FP0003261 awarded by the National Institutes of Health and DE-NA0003525 awarded by the Department of Energy. The government has certain rights in the invention.

BACKGROUND

The desire to improve drug efficacy, enhance targeted delivery to specific sites, and reduce side effects by controlling drug pharmacokinetic and biodistribution profiles has remained the main driving force for the development of drug delivery systems over the past two decades (Mitragotri et al., 2014; Blanco et al., 2015). Among all of the developed nanocarriers (e.g., micelles, liposomes, and mesoporous silica nanoparticles (NPs)) (Elsabahy et al., 2015; Grim et al., 2016; Croissant et al., 2017; Zhu et al., 2018; Richardson et al., 2016), nanosized metal-organic polyhedra (MOP) obtained upon metal-ligand coordination have attracted increasing attention for drug delivery owing to the highly designable nanoarchitectures, well-defined pore cavities, as well as diverse chemical properties and functions (Cook et al., 2013; Ahmad et al., 2015; Harris et al., 2013; Grishagin et al., 2014; Yu et al., 2016; Varhan et al., 2016). In this field, Therrien et al. presented a series of organometallic cages as anticancer drug delivery vehicles for photodynamic therapy (Therrien et al., 2008; Schmitt et al., 2012). Lippard and co-workers reported a well-defined metal-organic octahedron that can enhance the delivery of cis-platin prodrugs to cancer cells (Zheng et al., 2015). In addition, Isaacs and co-workers highlighted the potential of host-guest interactions, by combining MOP with cucurbituril, for enhanced delivery of chemotherapeutic drugs (Samanta et al., 2015; Samanta et al., 2017). Although many MOP-based supramolecular systems have been developed for drug delivery applications (Zhao et al., 2011; Xu et al., 2017; Rodriguez et al., 2017; Croissant et al., 2018), compared to the well-developed NP-based systems such as mesoporous silica NPs (Croissant et al., 2018), the use of MOP for drug delivery is still in its infancy. This is especially the case IN research concerning targeted drug delivery for cancer therapy. A major limitation of MOP as nanocarriers is their rapid renal clearance and short circulation time owing to their small size, which is typically below the filtration barrier of the glomerulus (e.g., ≈5.5 nm) (Samanta et al., 2016; Samanta et al., 2017). Furthermore, using coordination complexes for targeted therapy requires their functionalization with various targeting ligands consisting of small molecular moieties or large antibodies.

SUMMARY

Targeted drug delivery remains at the forefront of biomedical research but remains a challenge to date. To overcome these limitations, the superassembly of nanosized metal-organic polyhedra (MOP) and their biomimetic coatings of lipid bilayers are described herein, which synergistically combines the advantages of micelles and supramolecular coordination cages for targeted drug delivery. The superassembly technique affords unique hydrophobic features that endow individual MOP to act as nanobuilding blocks and enable their superassembly into larger well-defined nanocarriers with homogeneous sizes over a broad range of diameters. Various cargos are controllably loaded into the MOP with high payloads, and the nanocages are then superassembled to form multidrug delivery systems. Additionally, functional nanoparticles are introduced into the superassemblies via a one-pot process for versatile bioapplications. The MOP superassemblies are surface-engineered with epidermal growth factor receptors and can be targeted to cancer cells. In vivo studies indicated the assemblies have a substantial circulation half-life of 5.6 h and undergo renal clearance, characteristics needed for nanomedicines.

In one embodiment, a method to prepare a population of metal-organic polyhedra (MOP) supported micelle nanoparticles (NPs) is provided. The method includes combining metal to form nodes and an organic ligand comprising one or more hydrophobic chains under conditions to form a population of metal-organic polyhedra units; and combining the population of metal-organic polyhedra units and a micellar solution under conditions to form single MOP-supported micelle nanoparticles (NPs). In one embodiment, the metal is palladium, copper, zinc, platinum, manganese, beryllium, iron, chromium, cobalt, aluminum, zirconium, indium, or europium. In one embodiment, the metal is monovalent, divalent, trivalent or tetravalent. In one embodiment, the hydrophobic chain is a C1-C20 alkyl chain. In one embodiment, the hydrophobic chain is a dodecyl chain. In one embodiment, the hydrophobic chain is a octyl chain. In one embodiment, the organic ligand comprises a carboxylate, such as 1,4-benzenedicarboxylic, heterocyclic azolate, pyridine, thiophene, furan, pyrrole, or cyanide.

In one embodiment, the conditions to form single MOP-supported micelle nanoparticles comprise sonication. In one embodiment, the conditions to form metal-organic polyhedra units comprise applying heat. In one embodiment, the conditions to form metal-organic polyhedral yield a precipitate. In one embodiment, the diameter of a metal-organic polyhedra unit is from about 1 nm to about 15 nm. In one embodiment, the diameter of the metal-organic polyhedra unit is from about 10 nm to about 25 nm. In one embodiment, the diameter of the metal-organic polyhedra unit is from about 3 nm to about 10 nm. In one embodiment, the diameter of the micelle is from about 5 nm to about 10 nm. In one embodiment, the diameter of the micelle is from about 10 nm to about 25 nm, 10 nm to about 20 nm or about 15 nm to about 25 nm. In one embodiment, the diameter of the micelle is about 100 nm to about 800 nm, about 200 nm to about 500 nm or about 500 nm to about 900 nm. In one embodiment, the diameter of the micelle is from about 1000 nm to about 3000 nm or about 1500 nm to about 2500 nm. In one embodiment, the micelle solution comprises PEG, DSPE, or combination thereof In one embodiment, the micelle solution comprises DSPC, DSPE, DSPE-PEG, DSPE-PEG-biotin, DSPE-PEG-carboxy NHS, DPPC, DPPE, DMPC, DOPC, DOPE, DOPG, DOPS, DOTAP, DOPE-PEG-amine, DOPE-PEG-azide, or a combination thereof. In one embodiment, the PEG has a chain length (number of PEO units) of 4, 5, 6, 7, 8, 9, 10, 11, 12, 13, 14, 15, 16, 17, 18, 19, 20, 21, 22, 23, 24, or 25. In one embodiment, the PEG has a chain length (number of PEO units) of 6, 9, 10, 23, 34, 45, 68, 90, 113, 136, 181, or 227. In one embodiment, the method further comprises forming superassemblies with the MOP containing micelle. In one embodiment, the diameter of the superassemblies is from about 100 nm to about 900 nm. In one embodiment, the diameter of the superassemblies is from about 100 nm to about 300 nm. In one embodiment, the diameter of the superassemblies is from about 300 nm to about 500 nm, 400 nm to about 600 nm or 600 nm to about 800 nm. In one embodiment, the diameter of the superassemblies is from about 1 µm to about 100 µm or 1 µm to about 10 µm. In one embodiment, the diameter of the superassemblies is from about 100 µm to about 300 µm. In one embodiment, the diameter of the superassemblies is from about 300 µm to about 500 µm, 400 µm to about 600 µm or 600 µm to about 800 µm. In one embodiment, the MOP containing micelles or superassemblies further comprise one or more cargo molecules. In one embodiment, the cargo comprises a drug, a dye or a contrast agent, or combinations thereof In one embodiment, the cargo comprises an antibody or a fragment thereof, a protein ligand, a quantum dot or a gold nanoparticle. In one embodiment, the MOPs in the superassemblies have more than one type of drug, cell, contrast or imaging agent, protein or nanoparticle. In one embodiment, the micelle or superassemblies comprise one or more targeting molecules. Populations of the single MOP-supported micelle nanoparticles and of the superassemblies, and uses thereof are, also provided. In one embodiment, one or more different cargo molecules are mixed with metal-organic polyhedra, then with micelles to form superassemblies. In one embodiment, different ratios of cargo loaded metal-organic polyhedral and micelles are mixed. In one embodiment, a protein or other ligand, e.g., antibody, is grafted onto the surface of the micelle. In one embodiment, a population of superassemblies is added to a membrane. In one embodiment, a drug, e.g., doxorubicin, cyclophosphamide, gemcitabine, cytarabine, paclitaxel, docetaxel, vincristine sulfate, afatinib, dexamethasone, or rapamycin, are loaded into the polyhedral.

DETAILED DESCRIPTION

The disclosed fabrication technique affords a synthesis process and the organization of individual MOP to form advanced hierarchical structures. Specifically, in one embodiment, the superassembly of MOP supported micelles (MOPsa@micelle) for targeted drug delivery is described (see Scheme 1a in FIG. 1A). The decoration of the outer surface of the MOP with hydrophobic chains transforms MOP units into nanobuilding blocks that can self-assemble into larger and well-defined superassemblies within micelles. This approach is different from the reported molecular building block (MBB) approach that is used to construct metal-organic framework (MOF)-based lipid bilayers, where the open metal sites of MOF units allow further coordination of additional organic ligands to form MOF NPs (Scheme 1b in FIG. 1A). Nonetheless, the MBB approach typically affords limited size control, whereas the superassembly approach described herein provides homogeneous size distributions in broad ranges of diameters through the simple control of the MOP concentration to obtain ultrasmall single MOP@micelle and MOPsa@micelle. In addition, owing to the highly porous nature of the MOP, various molecules including cancer drugs can be controllably loaded into individual MOP units with high payloads and subsequently integrated into MOP superassemblies to form multiple compound (cargo), such as multiple drug, delivery systems. Furthermore, the MOP superassembly approach enabled the modular assembly of MOPs with additional functional NPs such as fluorescent quantum dots (QDs) for multifluorescence imaging or gold NPs for enhanced bioimaging.

To demonstrate the potential of the MOP superassembly concept for drug delivery, a Fujita-type MOP composed of dozens of dodecyl chains was chosen as a prototype. As described herein below, a dose-dependent assay for MOPsa@ micelles of different sizes demonstrated negligible hemolytic activities and long-term colloidal stability in various media, thereby mitigating possible concerns of structure disassembly during circulation. Cell viability tests further demonstrated the good biocompatibility of the MOPsa@micelles that is related to the NP size and the molecular weight of the polyethylene glycol (PEG) that was used for surface modification. Importantly, designing MOPsa@micelle nanocarriers with targeting moieties enabled targeted cell, e.g., targeted cancer cell, delivery and in vivo experiments using a mouse model also confirmed the good circulation. Taken together, this modular superassembly approach combines the synergistic advantages of micelles (e.g., low inherent toxicity and long circulation time) and the MOP superassembly (e.g., highly controlled architecture, stability, and high payloads of multiple cargos), and promotes the design of MOP-inspired nanocarriers for targeted cancer therapies.

Figure 1A:
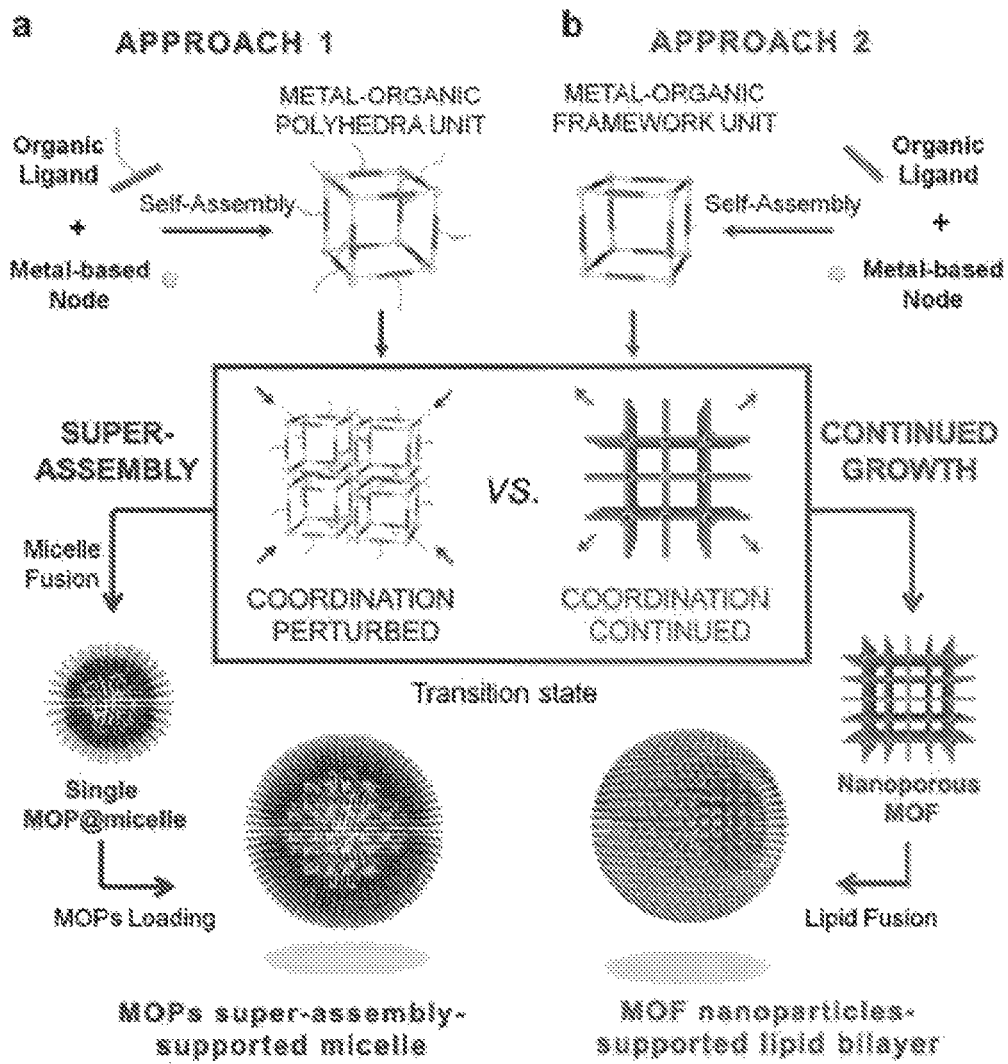
FIGS. 1Aa-1Ab. Schematic illustration of a) the design and construction of drug delivery nanocarriers (single MOP or MOP superassembly-supported micelle) based on a modular superassembly approach and b) the solution synthesis of MOF NP-supported lipid bilayers based on MBB approach.
Figure 1B:
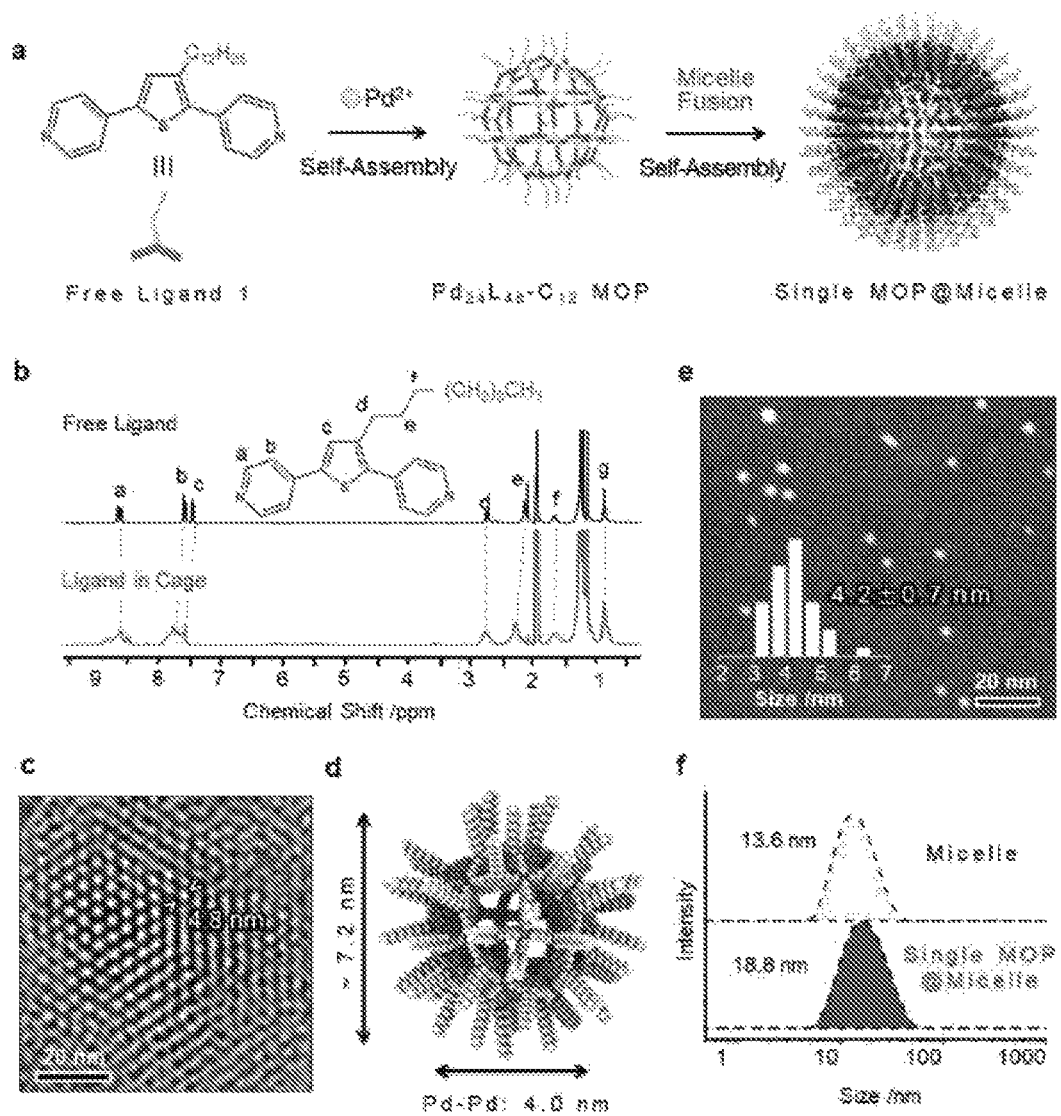
FIGS. 1Ba-1Bf. a) Self-assembly of $Pd_{24}L_{48}$-$C_{12}$ MOP with hydrophobic chain decoration and lateral fusion of micelles. b) $^1$H NMR spectra of free ligand and $Pd_{24}L_{48}$-$C_{12}$ MOP in DMSO-$d_6$ solvent. c) HR-TEM image of the $Pd_{24}L_{48}$-$C_{12}$ MOP assembly; the distance between two closed packed cages is also highlighted. d) Optimized structures of $Pd_{24}L_{48}$-$C_{12}$ MOP based on MM calculations. e) Dark-field STEM image of single $Pd_{24}L_{48}$-$C_{12}$ MOP-supported micelle and the related size distribution. f) DLS data of $P_6LEL$-based micelle before and after loading with single $Pd_{24}L_{48}$-$C_{12}$ MOP NPs.

The MOP unit may contain any metal including but not limited to Pd, Pt, Be, Cu, Zn, Ag, Mg, Mn, Fe, Co, Ni, Cd, Al, Sc V, Cr, Ga, In, lanthanide, Ti, Zr, Hf, Rh, or Ce, or any combination thereof, and the polyhedra may be of any shape, including but not limited to a tetrahedron, octahedron, cube, icosahedron, dodecahedron, tricontahedron, icosadodecahedron, rhomic dodecahedron or cub-octahedron Any ligand may be employed in the synthetic method, ligands including ligand 1 in FIG. 1B, the ligand in Samanta et al. (2016), the ligand in Samanata et al. (2018), and those in the Figures in Vardhan and Verpoort (*Aust. J. Chem.*, 68:707 (2015), the disclosures of which are incorporated by reference herein.

The hydrophobic chain that may be employed with the ligand includes but is not limited to a substituted or unsubstituted alkyl chain, e.g., a C3 to C10, C12 to C20 or C20 to C30 alkyl chain, a substituted or unsubstituted alkyene chain e.g., a C3 to C10, C12-C20, or C20 to C30 alkenyl chain, or a substituted or unsubstituted alkyne chain. When heteroatoms (N, O and S typically) are allowed to replace carbon atoms as in heteroalkyl groups, for example, the numbers describing the group, though still written as e.g. $C_1$-$C_6$, represent the sum of the number of carbon atoms in the group plus the number of such heteroatoms, that are included as replacements for carbon atoms in the backbone of the ring or chain being described. Alkyl, alkenyl and alkynyl groups are often optionally substituted to the extent that such substitution makes sense chemically. Typical substituents include, but are not limited to, halo, $=$O, $=$N—CN, $=$N—OR, $=$NR, OR, $NR_2$, SR, $SO_2R$, $SO_2NR_2$, $NRSO_2R$, $NRCONR_2$, NRCOOR, NRCOR, CN, COOR, $CONR_2$, OOCR, COR, and $NO_2$, wherein each R is independently H, $C_1$-$C_8$ alkyl, $C_2$-$C_8$ heteroalkyl, $C_1$-$C_8$ acyl, $C_2$-$C_8$ heteroacyl, $C_2$-$C_8$ alkenyl, $C_2$-$C_8$ heteroalkenyl, $C_2$-$C_8$ alkynyl, $C_2$-$C_8$ heteroalkynyl, $C_6$-$C_{10}$ aryl, or $C_5$-$C_{10}$ heteroaryl, and each R is optionally substituted with halo, $=$O, $=$N—CN, $=$N—OR', $=$NR', OR', NR'$_2$, SR', $SO_2R'$, $SO_2NR'_2$, NR'$SO_2R'$, NR'CONK'$_2$, NR'COOR', NR'COR', CN, COOR', CONR'$_2$, OOCR', COR', and $NO_2$, wherein each R' is independently H, $C_1$-$C_8$ alkyl, $C_2$-$C_8$ heteroalkyl, $C_1$-$C_8$ acyl, $C_2$-$C_8$ heteroacyl, $C_6$-$C_{10}$ aryl or $C_5$-$C_{10}$ heteroaryl. Alkyl, alkenyl and alkynyl groups can also be substituted by $C_1$-$C_8$ acyl, $C_2$-$C_8$ heteroacyl, $C_6$-$C_{10}$ aryl or $C_5$-$C_{10}$ heteroaryl, each of which can be substituted by the substituents that are appropriate for the particular group.

"Heteroalkyl", "heteroalkenyl", and "heteroalkynyl" and the like are defined similarly to the corresponding hydrocarbyl (alkyl, alkenyl and alkynyl) groups, but the 'hetero' terms refer to groups that contain one to three O, S or N heteroatoms or combinations thereof within the backbone residue; thus at least one carbon atom of a corresponding alkyl, alkenyl, or alkynyl group is replaced by one of the specified heteroatoms to form a heteroalkyl, heteroalkenyl, or heteroalkynyl group. The typical sizes for heteroforms of alkyl, alkenyl and alkynyl groups are generally the same as for the corresponding hydrocarbyl groups, and the substituents that may be present on the heteroforms are the same as those described above for the hydrocarbyl groups. For reasons of chemical stability, it is also understood that, unless otherwise specified, such groups do not include more than two contiguous heteroatoms except where an oxo group is present on N or S as in a nitro or sulfonyl group.

While "alkyl" as used herein includes cycloalkyl and cycloalkylalkyl groups, the term "cycloalkyl" may be used herein to describe a carbocyclic non-aromatic group that is connected via a ring carbon atom, and "cycloalkylalkyl" may be used to describe a carbocyclic non-aromatic group that is connected to the molecule through an alkyl linker. Similarly, "heterocyclyl" may be used to describe a non-aromatic cyclic group that contains at least one heteroatom as a ring member and that is connected to the molecule via a ring atom, which may be C or N; and "heterocyclylalkyl" may be used to describe such a group that is connected to another molecule through a linker. The sizes and substituents that are suitable for the cycloalkyl, cycloalkylalkyl, heterocyclyl, and heterocyclylalkyl groups are the same as those described above for alkyl groups. As used herein, these terms also include rings that contain a double bond or two, as long as the ring is not aromatic.

As used herein, "acyl" encompasses groups comprising an alkyl, alkenyl, alkynyl, aryl or arylalkyl radical attached at one of the two available valence positions of a carbonyl carbon atom, and heteroacyl refers to the corresponding groups wherein at least one carbon other than the carbonyl carbon has been replaced by a heteroatom chosen from N, O and S. Thus heteroacyl includes, for example, —C(=O)OR and —C(=O)NR$_2$ as well as —C(=O)-heteroaryl.

Acyl and heteroacyl groups are bonded to any group or molecule to which they are attached through the open valence of the carbonyl carbon atom. Typically, they are $C_1$-$C_8$ acyl groups, which include formyl, acetyl, pivaloyl, and benzoyl, and $C_2$-$C_8$ heteroacyl groups, which include methoxyacetyl, ethoxycarbonyl, and 4-pyridinoyl. The hydrocarbyl groups, aryl groups, and heteroforms of such groups that comprise an acyl or heteroacyl group can be substituted with the substituents described herein as generally suitable substituents for each of the corresponding component of the acyl or heteroacyl group.

"Aromatic" moiety or "aryl" moiety refers to a monocyclic or fused bicyclic moiety having the well-known characteristics of aromaticity; examples include phenyl and naphthyl. Similarly, "heteroaromatic" and "heteroaryl" refer to such monocyclic or fused bicyclic ring systems which contain as ring members one or more heteroatoms selected from O, S and N. The inclusion of a heteroatom permits aromaticity in 5 membered rings as well as 6 membered rings. Typical heteroaromatic systems include monocyclic $C_5$-$C_6$ aromatic groups such as pyridyl, pyrimidyl, pyrazinyl, thienyl, furanyl, pyrrolyl, pyrazolyl, thiazolyl, oxazolyl, and imidazolyl and the fused bicyclic moieties formed by fusing one of these monocyclic groups with a phenyl ring or with any of the heteroaromatic monocyclic groups to form a $C_8$-$C_{10}$ bicyclic group such as indolyl, benzimidazolyl, indazolyl, benzotriazolyl, isoquinolyl, quinolyl, benzothiazolyl, benzofuranyl, pyrazolopyridyl, quinazolinyl, quinoxalinyl, cinnolinyl, and the like. Any monocyclic or fused ring bicyclic system which has the characteristics of aromaticity in terms of electron distribution throughout the ring system is included in this definition. It also includes bicyclic groups where at least the ring which is directly attached to the remainder of the molecule has the characteristics of aromaticity. Typically, the ring systems contain 5-12 ring member atoms. For example, the monocyclic heteroaryls may contain 5-6 ring members, and the bicyclic heteroaryls contain 8-10 ring members.

Aryl and heteroaryl moieties may be substituted with a variety of substituents including $C_1$-$C_8$ alkyl, $C_2$-$C_8$ alkenyl, $C_2$-$C_8$ alkynyl, $C_5$-$C_{12}$ aryl, $C_1$-$C_8$ acyl, and heteroforms of these, each of which can itself be further substituted; other substituents for aryl and heteroaryl moieties include halo, OR, NR$_2$, SR, SO$_2$R, SO$_2$NR$_2$, NRSO$_2$R, NRCONR$_2$, NRCOOR, NRCOR, CN, COOR, CONR$_2$, OOCR, COR, and NO$_2$, wherein each R is independently H, $C_1$-$C_8$ alkyl, $C_2$-$C_8$ heteroalkyl, $C_2$-$C_8$ alkenyl, $C_2$-$C_8$ heteroalkenyl, $C_2$-$C_8$ alkynyl, $C_2$-$C_8$ heteroalkynyl, $C_6$-$C_{10}$ aryl, $C_5$-$C_{10}$ heteroaryl, $C_7$-$C_{12}$ arylalkyl, or $C_6$-$C_{12}$ heteroarylalkyl, and each R is optionally substituted as described above for alkyl groups. The substituent groups on an aryl or heteroaryl group may of course be further substituted with the groups described herein as suitable for each type of such substituents or for each component of the substituent. Thus, for example, an arylalkyl substituent may be substituted on the aryl portion with substituents described herein as typical for aryl groups, and it may be further substituted on the alkyl portion with substituents described herein as typical or suitable for alkyl groups.

Components of the micelle include but are not limited to any lipid or polymer including but not limited to 1,2-dioleoyl-sn-glycero-3-phosphocholine (DOPC), 1,2-dipalmitoyl-sn-glycero-3-phosphocholine (DPPC), 1,2-distearoyl-sn-glycero-3-phosphocholine (DSPC), 1,2-dioleoyl-sn-glycero-3-[phosphor-L-serine] (DOPS), 1,2-dioleoyl-3-trimethylammonium-propane (18:1 DOTAP), 1,2-dioleoyl-sn-glycero-3-phospho-(1'-rac-glycerol) (DOPG), 1,2-dioleoyl-sn-glycero-3-phosphoethanolamine (DOPE), 1,2-dipalmitoyl-sn-glycero-3-phosphoethanolamine (DPPE), 1,2-dioleoyl-sn-glycero-3-phosphoethanolamine-N-[methoxy(polyethylene glycol)-2000] (18:1 PEG-2000 PE), 1,2-dipalmitoyl-sn-glycero-3-phosphoethanolamine-N-[methoxy(polyethylene glycol)-2000] (16:0 PEG-2000 PE), 1-oleoyl-2-[12-[(7-nitro-2-1,3-benzoxadiazol-4-yl)amino]lauroyl]-sn-glycero-3-phosphocholine (18:1-12:0 NBD PC), 1-palmitoyl-2-{12-[(7-nitro-2-1,3-benzoxadiazol-4-yl)amino]lauroyl}-sn-glycero-3-phosphocholine (16:0-12:0 NBD PC), cholesterol and mixtures/combinations thereof. Cholesterol, not technically a lipid, but presented as a lipid for purposes of an embodiment of the given the fact that cholesterol may be an important component of the lipid bi-layer of protocells according to an embodiment. Often cholesterol is incorporated into lipid bi-layers of protocells in order to enhance structural integrity of the bi-layer. These lipids are all readily available commercially from Avanti Polar Lipids, Inc. (Alabaster, Alabama, USA). DOPE and DPPE are particularly useful for conjugating (through an appropriate crosslinker) peptides, polypeptides, including antibodies, RNA and DNA through the amine group on the lipid.

Ion one embodiment, components of the micelle include but are not limited to DSPC, DSPE, DSPE-PEG, DSPE-PEG-biotin, DSPE-PEG-carboxy NETS, DPPC, DPPE, DMPC, DOPC, DOPE, DOPG, DOPS, DOTAP, DOPE-PEG-amine, DOPE-PEG-azide, or a combination thereof.

In certain embodiments, the micelle is comprised of one or more phosphatidyl-cholines (PCs) selected from the group consisting of 1,2-distearoyl-sn-glycero-3-phosphocholine (DSPC) [18:0], 1,2-dioleoyl-sn-glycero-3-phosphocholine (DOPC) [18:1 (Δ9-Cis)], 1,2-dimyristoyl-sn-glycero-3-phosphocholine (DMPC), 1,2-dioleoyl-3-trimethylammonium-propane (DOTAP), 1-palmitoyl-2-oleoyl-sn-glycero-3-phosphocholine (POPC), egg PC, and a lipid mixture comprising of one or more unsaturated phosphatidyl-cholines, DMPC [14:0] having a carbon length of 14 and no unsaturated bonds, 1,2-dipalmitoyl-sn-glycero-3-phosphocholine (DPPC) [16:0], POPC [16:0-18:1], and DOTAP [18:1]. The use of DSPC and/or DOPC as well as other zwitterionic phospholipids as a principal component (often in combination with a minor amount of cholesterol) is employed in certain embodiments in order to provide a protocell with a surface zeta potential which is neutral or close to neutral in character.

In other embodiments, the micelle is comprised of a mixture of (1) DSPC, DOPC and optionally one or more phosphatidyl-cholines (PCs) selected from the group consisting of 1,2-dimyristoyl-sn-glycero-3-phosphocholine (DMPC), 1,2-dioleoyl-3-trimethylammonium-propane (DOTAP), 1-palmitoyl-2-oleoyl-sn-glycero-3-phosphocholine (POPC), a lipid mixture comprising (in molar percent) between about 50% to about 70% or about 51% to about 69%, or about 52% to about 68%, or about 53% to about 67%, or about 54% to about 66%, or about 55% to about 65%, or about 56% to about 64%, or about 57% to about 63%, or about 58% to about 62%, or about 59% to about 61%, or about 60%, of one or more unsaturated phosphatidyl-choline, DMPC [14:0] having a carbon length of 14 and no unsaturated bonds, 1,2-dipalmitoyl-sn-glycero-3-phosphocholine (DPPC) [16:0], POPC [16:0-18:1] and DOTAP [18:1]; and wherein (b) the molar concentration of DSPC and DOPC in the mixture is between about 10% to about 99% or about 50% to about 99%, or about 12% to about 98%, or about 13% to about 97%, or about 14% to about 96%, or about 55% to about 95%, or about 56% to about 94%, or about 57% to about 93%, or about 58% to about 42%, or about 59% to about 91%, or about 50% to about 90%, or about 51% to about 89%.

In certain embodiments, the micelle is comprised of one or more compositions selected from the group consisting of a phospholipid, a phosphatidyl-choline, a phosphatidyl-serine, a phosphatidyl-diethanolamine, a phosphatidylinosite, a sphingolipid, and an ethoxylated sterol, or mixtures thereof In illustrative examples of such embodiments, the phospholipid can be a lecithin; the phosphatidylinosite can be derived from soy, rape, cotton seed, egg and mixtures thereof; the sphingolipid can be ceramide, a cerebroside, a sphingosine, and a sphingomyelin, and a mixture thereof; the ethoxylated sterol can be phytosterol, PEG-(polyethyleneglycol)-5-soy bean sterol, and PEG-(polyethylenegylcol)-5 rapeseed sterol. In certain embodiments, the phytosterol comprises a mixture of at least two of the following compositions: sitosterol, campesterol and stigmasterol.

In still other illustrative embodiments, the micelle is comprised of one or more phosphatidyl groups selected from the group consisting of phosphatidyl choline, phosphatidyl-ethanolamine, phosphatidyl-serine, phosphatidyl-inositol, lyso-phosphatidyl-choline, lyso-phosphatidyl-ethanolamine, lyso-phosphatidyl-inositol and lyso-phosphatidyl-inositol.

In still other illustrative embodiments, the micelle is comprised of phospholipid selected from a monoacyl or diacylphosphoglyceride.

In still other illustrative embodiments, the micelle is comprised of one or more phosphoinositides selected from the group consisting of phosphatidyl-inositol-3-phosphate (PI-3-P), phosphatidyl-inositol-4-phosphate (PI-4-P), phosphatidyl-inositol-5-phosphate (PI-5-P), phosphatidyl-inositol-3,4-diphosphate (PI-3,4-P2), phosphatidyl-inositol-3,5-diphosphate (PI3,5-P2), phosphatidyl-inositol-4,5-diphosphate (PI-4,5-P2), phosphatidyl-inositol-3,4,5-triphosphate (PI-3,4,5-P3), lysophosphatidyl-inositol-3-phosphate (LPI-3-P), lysophosphatidyl-inositol-4-phosphate (LPI-4-P), lysophosphatidyl-inositol-5-phosphate (LPI-5-P), lysophosphatidyl-inositol-3,4-diphosphate (LPI-3,4-P2), lysophosphatidyl-inositol3,5-diphosphate (LPI3,5-P2), lysophosphatidyl-inositol-4,5-diphosphate (LPI-4,5-P2), and lysophosphatidyl-inositol-3,4,5-triphosphate (LPI-3,4,5-P3), and phosphatidyl-inositol (PI), and lysophosphatidyl-inositol (LPI).

In still other illustrative embodiments, the micelle is comprised of one or more phospholipids selected from the group consisting of PEG-poly(ethylene glycol)-derivatized distearoylphosphatidylethanolamine (PEG-DSPE), PEG-poly(ethylene glycol)-derivatized dioleoylphosphatidylethanolamine (PEG-DOPE), poly(ethylene glycol)-derivatized ceramides (PEG-CER), hydrogenated soy phosphatidylcholine (HSPC), egg phosphatidylcholine (EPC), phosphatidyl ethanolamine (PE), phosphatidyl glycerol (PG), phosphatidyl inositol (PI), monosialoganglioside, sphingomyelin (SPM), distearoylphosphatidylcholine (DSPC), dimyristoylphosphatidylcholine (DMPC), and dimyristoylphosphatidylglycerol (DMPG).

In still other illustrative embodiments, the micelle comprises one or more PEG-containing phospholipids, for example 1,2-dioleoyl-sn-glycero-3-phosphoethanolamine-N-[methoxy (polyethylene glycol)] (ammonium salt) (DOPE-PEG), 1,2-distearoyl-sn-glycero-3-phosphoethanolamine-N-[methoxy (polyethylene glycol)] (ammonium salt) (DSPE-PEG), 1,2-distearoyl-sn-glycero-3-phosphoethanolamine-N-[amino (polyethylene glycol)] (DSPE-PEG-$NH_2$) (DSPE-PEG). In the PEG-containing phospholipid, the PEG group ranges from about 2 to about 250 ethylene glycol units, about 5 to about 100, about 10 to 75, or about 40-50 ethylene glycol units. In certain exemplary embodiments, the PEG-phospholipid is 1,2-dioleoyl-sn-glycero-3-phosphoethanolamine-N-[methoxy(polyethylene glycol)-2000] (ammonium salt) (DOPE-$PEG_{2000}$), 1,2-distearoyl-sn-glycero-3-phosphoethanolamine-N-[methoxy(polyethylene glycol)-2000] (ammonium salt) (DSPE-$PEG_{2000}$), 1,2-distearoyl-sn-glycero-3-phosphoethanolamine-N-[amino(polyethylene glycol)-2000] (DSPE-$PEG_{2000}$-$NH_2$) which can be used to covalent bind a functional moiety to the lipid bi-layer.

Cargo or other functional molecules for inclusion in the single MOP@micelle or $MOP_{sa}$@micelle include but are not limited to "anti-cancer agents" including but not limited to everolimus, trabectedin, abraxane, TLK 286, AV-299, DN-101, pazopanib, GSK690693, RTA 744, ON 0910.Na, ALD 6244 (ARRY-142886), AMN-107, TKI-258, GSK461364, AZD 1152, enzastaurin, vandetanib, ARQ-197, MK-0457, MLN8054, PHA-739358, R-763, AT-9263, a FLT-3 inhibitor, a VEGFR inhibitor, an EGFR TK inhibitor, an aurora kinase inhibitor, a PIK-1 modulator, a Bcl-2 inhibitor, an HDAC inhibitor, a c-MET inhibitor, a PARP inhibitor, a Cdk inhibitor, an EGFR TK inhibitor, an IGFR-TK inhibitor, an anti-EGFR antibody, an anti-HGF antibody, a PI3 kinase inhibitors, an AKT inhibitor, a JAK/S TAT inhibitor, a checkpoint-1 or 2 inhibitor, a focal adhesion kinase inhibitor, a Map kinase kinase (mek) inhibitor, a VEGF trap antibody, pemetrexed, erlotinib, dasatanib, nilotinib, decatanib, panitumumab, amrubicin, oregovomab, Lep-etu, nolatrexed, azd2171, batabulin, ofatumumab, zanolimumab, edotecarin, tetrandrine, rubitecan, tesmilifene, oblimersen, ticilimumab, ipilimumab, gossypol, Bio 111, 131-I-TM-601, ALT-110, BIO 140, CC 8490, cilengitide, gimatecan, IL13-PE38QQR, INO 1001, $IPdR_1$ KRX-0402, lucanthone, LY 317615, neuradiab, vitespen, Rta 744, Sdx 102, talampanel, atrasentan, Xr 311, romidepsin, ADS-100380, sunitinib, 5-fluorouracil, vorinostat, etoposide, gemcitabine, doxorubicin, liposomal doxorubicin, 5'-deoxy-5-fluorouridine, vincristine, temozolomide, ZK-304709, seliciclib; PD0325901, ALD-6244, capecitabine, L-Glutamic acid, N-[4-[2-(2-amino-4,7-dihydro-4-oxo-1H-pyrrolo [2,3-d]pyrimidin-5-yl)ethyl]benzoyl]-, disodium salt, heptahydrate, camptothecin, PEG-labeled irinotecan, tamoxifen, toremifene citrate, anastrozole, exemestane, letrozole, DES (diethylstilbestrol), estradiol, estrogen, conjugated estrogen, bevacizumab, IMC-1C11, CHIR-258, 3-[5-(methylsulfonylpiperadinemethyl)-indolyl]-quinolone, vatalanib, AG-013736, AVE-0005, the acetate salt of [D-Ser(But)6, Azgly10] (pyro-Glu-His-Trp-Ser-Tyr-D-Ser(But)-Leu-Arg-Pro-Azgly-NH$_2$ acetate [$C_{59}H_{84}N_{18}O_{14}$—($C_2H_4O_2$)x where x=1 to 2.4], goserelin acetate, leuprolide acetate, triptorelin pamoate, medroxyprogesterone acetate, hydroxyprogesterone caproate, megestrol acetate, raloxifene, bicalutamide, flutamide, nilutamide, megestrol acetate, CP-724714, TAK-165, HKI-272, erlotinib, lapatinib, canertinib, ABX-EGF antibody, erbitux, EKB-569, PKI-166, GW-572016, Ionafarnib, BMS-214662, tipifarnib, amifostine, NVP-LAQ824, suberoyl anilide hydroxamic acid, valproic acid, trichostatin A, FK-228, SU11248, sorafenib, KRN951, aminoglutethimide, amsacrine, anagrelide, L-asparaginase, Bacillus Calmette-Guerin (BCG) vaccine, bleomycin, buserelin, busulfan, carboplatin, carmustine, chlorambucil, cisplatin, cladribine, clodronate, cyproterone, cytarabine, dacarbazine, dactinomycin, daunorubicin, diethylstilbestrol, epirubicin, fludarabine, fludrocortisone, fluoxymesterone, flutamide, gemcitabine, gleevac, hydroxyurea, idarubicin, ifosfamide, imatinib, leuprolide, levamisole, lomustine, mechlorethamine, melphalan, 6-mercaptopurine, mesna, methotrexate, mitomycin, mitotane, mitoxantrone, nilutamide, octreotide, oxaliplatin, pamidronate, pentostatin, plicamycin, porfimer, procarbazine, raltitrexed, rituximab, streptozocin, teniposide, testosterone, thalidomide, thioguanine, thiotepa, tretinoin, vindesine, 13-cis-retinoic acid, phenylalanine mustard, uracil mustard, estramustine, altretamine, floxuridine, 5-deoxyuridine, cytosine arabinoside, 6-mercaptopurine, deoxycoformycin, calcitriol, valrubicin, mithramycin, vinblastine, vinorelbine, topotecan, razoxin, marimastat, COL-3, neovastat, BMS-275291, squalamine, endostatin, SU5416, SU6668, EMD121974, interleukin-12, IM862, angiostatin, vitaxin, droloxifene, idoxifene, spironolactone, finasteride, cimetidine, trastuzumab, denileukin diftitox, gefitinib, bortezomib, paclitaxel, cremophor-free paclitaxel, docetaxel, epithilone B, BMS-247550, BMS-310705, droloxifene, 4-hydroxytamoxifen, pipendoxifene, ERA-923, arzoxifene, fulvestrant, acolbifene, lasofoxifene, idoxifene, TSE-424, HMR-3339, ZK186619, topotecan, PTK787/ZK 222584, VX-745, PD 184352, rapamycin, 40-O-(2-hydroxyethyl)-rapamycin, temsirolimus, AP-23573, RAD001, ABT-578, BC-210, LY294002, LY292223, LY292696, LY293684, LY293646, wortmannin, ZM336372, L-779, 450, PEG-filgrastim, darbepoetin, erythropoietin, granulocyte colony-stimulating factor, zolendronate, prednisone, cetuximab, granulocyte macrophage colony-stimulating factor, histrelin, pegylated interferon alfa-2a, interferon alfa-2a, pegylated interferon alfa-2b, interferon alfa-2b, azacitidine, PEG-L-asparaginase, lenalidomide, gemtuzumab, hydrocortisone, interleukin-11, dexrazoxane, alemtuzumab, all-transretinoic acid, ketoconazole, interleukin-2, megestrol, immune globulin, nitrogen mustard, methylprednisolone, ibritumomab tiuxetan, androgens, decitabine, hexamethylmelamine, bexarotene, tositumomab, arsenic trioxide, cortisone, etidronate, mitotane, cyclosporine, liposomal daunorubicin, Edwina-asparaginase, strontium 89, casopitant, netupitant, an NK-1 receptor antagonists, palonosetron, aprepitant, diphenhydramine, hydroxyzine, metoclopramide, lorazepam, alprazolam, haloperidol, droperidol, dronabinol, dexamethasone, methylprednisolone, prochlorperazine, granisetron, ondansetron, dolasetron, tropisetron, pegfilgrastim, erythropoietin, epoetin alfa, darbepoetin alfa and mixtures thereof; anti-HIV agents" including but not limited to nucleoside reverse transcriptase inhibitors (NRTI), other non-nucleoside reverse transcriptase inhibitors (i.e., those which are not representative), protease inhibitors, fusion inhibitors, among others, exemplary compounds of which may include, for example, 3TC (Lamivudine), AZT (Zidovudine), (−)-FTC, ddI (Didanosine), ddC (zalcitabine), abacavir (ABC), tenofovir (PMPA), D-D4FC (Reverset), D4T (Stavudine), Racivir, L-FddC, L-FD4C, NVP (Nevirapine), DLV (Delavirdine), EFV (Efavirenz), SQVM (Saquinavir mesylate), RTV (Ritonavir), IDV (Indinavir), SQV (Saquinavir), NFV (Nelfinavir), APV (Amprenavir), LPV (Lopinavir), fusion inhibitors such as T20, among others, fuseon and mixtures thereof.

Other cargos include but are not limited other nanoparticles, such as gold NP and quantum dots.

The micelles or superassemblies may comprise targeting molecules, e.g., a cell targeting species (e.g., a peptide, antibody, such as a monoclonal antibody, an affibody or a small molecule moiety which binds to a cell, among others); a fusogenic peptide that promotes endosomal escape of protocells; a cargo, including one or more drugs (e.g., an anti-cancer agent, anti-viral agent, antibiotic, antifungal agent, etc.); a polynucleotide, such as encapsulated DNA, double stranded linear DNA, a plasmid DNA, small interfering RNA, small hairpin RNA, microRNA, a peptide, polypeptide or protein, an imaging agent, or a mixture thereof, among others), wherein one of said cargo components is optionally conjugated further with a nuclear localization sequence. In certain embodiments, the micelle or lipid may comprise PEG groups and/or targeting peptides. A targeting species including, for example, targeting peptides including oligopeptides, antibodies, aptamers, and PEG (polyethylene glycol) (including PEG covalently linked to specific targeting species); a cell penetration peptide such as a fusogenic peptide or an endosomolytic peptide as otherwise described herein. Targeting peptides may be complexed or covalently linked to the lipid layer through use of a crosslinking agent.

The invention will be further described by the following non-limiting example.

EXAMPLE 1

Materials and Methods

Reagents. All chemicals and reagents were used as received. 4-Pyridylboronic acid pinacol ester, tetrakis(triphenylphosphine) palladium(0), potassium phosphate, 1,4-dioxane, 2,5-dibromo-3-dodecylthiophene, chloroform, Pd(BF$_4$)$_2$, ethyl acetate, diethyl ether, polyoxyethylene (6) lauryl ether, polyoxyethylene (10) lauryl ether, polyoxyethylene (23) lauryl ether, dimethyl sulfoxide (DMSO), doxorubicin (DOX), sulforhodamine B, Mn(III)tetra (4-sulfonatophenyl) porphyrin, 6-aminocoumarin, fluorescein isothiocyanate, CdSe/ZnS quantum dots (QDs), Ham's F-12K (Kaighn's) medium, Iscove's modified Dulbecco's media (IMDM), and formaldehyde solution (36.5-38% in H$_2$O) were purchased from Sigma-Aldrich. Au NPs were synthesized according to the reported literature. Epidermal growth factor (EGFR)-biotin and NeutrAvidin were purchased from Thermo Fisher Scientific. 1,2-distearoyl-sn-glycero-3-phosphoethanolamine-N-[biotinyl(polyethylene glycol)-2000] (ammonium salt)) (DSPEPEG-2000-biotin) and 1,2-distearoyl-sn-glycero-3-phosphoeth-anolamine-N-[methoxy (polyethyleneglycol)-2000] (ammonium salt) (DSPE-PEG-2000) were purchased from Avanti Polar Lipids. Heat-inactivated fetal bovine serum (FBS), 10× phosphate-buffered saline (PBS), 0.5% trypsin-ethylenediaminetetraacetic acid (EDTA) solution, and penicillin-streptomycin (PS) were purchased from Gibco (Logan, UT). Dulbecco's modification of Eagle's medium (DMEM) was obtained from Corning Cellgro (Manassas, VA), Absolute (200 proof) ethanol was obtained from Pharmco-Aaper (Brookfield, CT). CellTiter-Glo 2.0 assay kit was purchased from Promega (Madison, WI). Hoechst 33342 were obtained from Thermo Fisher Scientific (Rockford, IL.). 1×PBS, Alexa Fluor 488 phalloidin, and rhodamine phalloidin were purchased from Life Technologies (Eugene, Oreg.). Milli-Q water with a resistivity of 18.2 MΩ cm was obtained from an inline Millipore RiOs/Origin water purification system.

Characterization. The morphology of the samples was characterized by field-emission gun scanning transmission electron microscopy (STEM, JEOL 2010F) at 200 kV and transmission electron microscopy (TEM, Hitachi H-7650) at 200 kV. Argon adsorption-desorption isotherms were obtained using a Quantachrome ASiQ2 intrument at 87 K. $^1$H NMR spectra were obtained using a JEOLJNM-ECA300 at 300 MHz. Atomic force microscopy (AFM) images were acquired using an Asylum Research MFP-3D™ AFM. UV-Vis absorption spectra were recorded using a Perkin-Elmer UV/vis Lambda 35 spectrometer. The fluorescence emission measurements were carried out using a fluorescence spectrometer (Perkin-Elmer LS55). Fluorescence images were acquired using a Zeiss LSM510 META (Carl Zeiss Micro-Imaging, Inc.; Thornwood, NY, USA) operated in channel mode of the LSM510 software. The software used for the optimization of the structure of $Pd_{24}L_{48}$-$C_{12}$ MOP was Materials Studio 8.0. Due to the large coordination structure of $Pd_{24}L_{48}$-$C_{12}$ MOP (more 3,000 atoms), only molecular mechanics (MM) simulation was used.

Ligand 1 Synthesis

For the synthesis of ligand 1, 2.10 g 4-pyridylboronic acid pinacol ester (9.80 mmol), 0.407 g tetrakis(triphenyl-phosphine)palladium(0) (0.352 mmol), and 5.95 g potassium phosphate (28.0 mmol) were first added into a three-neck flask. Under the protection of argon atmosphere, 70 mL 1,4-dioxane and 1.121 mL 2,5-dibromo-3-dodecylthiophene (3.61 mmol) were then added, and the suspension was stirred at 90° C. for 3 days. After cooling down, the residue was filtered and washed with chloroform. The filtrate was further purified by silica gel column chromatography to give a yellow solid.

$Pd_{24}L_{48}$-$C_{12}$ MOP Synthesis

For the preparation of $Pd_{24}L_{48}$-$C_{12}$, 31.0 mg ligand 1 (76.4 μmol) was mixed with 8.80 mg $Pd(BF_4)_2$ (38.2 μmol) in a mixture of acetonitrile and chloroform (3:1 v/v) and reacted at 70° C. for 24 hours. After cooling down, an excess amount of a mixture of ethyl acetate and diethyl ether (1:1 v/v) was added to the solution to promote precipitation. The precipitate was centrifuged (10,000 rpm, 10 minutes) and dried in vacuum to give the desired cage as a light yellow solid.

MOP Super-Assembly

For the synthesis of single MOP@micelle, 10 mg mL-1 of polyoxyethylene (6) lauryl ether-based micelle was first prepared. Then, a small drop of MOP solution (0.038 mM in DMSO) was added into the micelle solution followed by sonication to promote encapsulation. For the synthesis of $MOP_{sa}$@micelle with different sizes, 1 mg mL$^{-1}$ of polyoxyethylene (6) lauryl ether-based micelle was prepared and then different amounts of $Pd_{24}L_{48}$-$C_{12}$ MOP (0.17 mM in DMSO) were added, followed by sonication to promote super-assembly. To vary the length of PEG outside the micelle, an alternative assembly unit, e.g., polyoxyethylene (10) lauryl ether or polyoxyethylene (23) lauryl ether, was used.

Guest Loading Number Calculation

Figure 3:
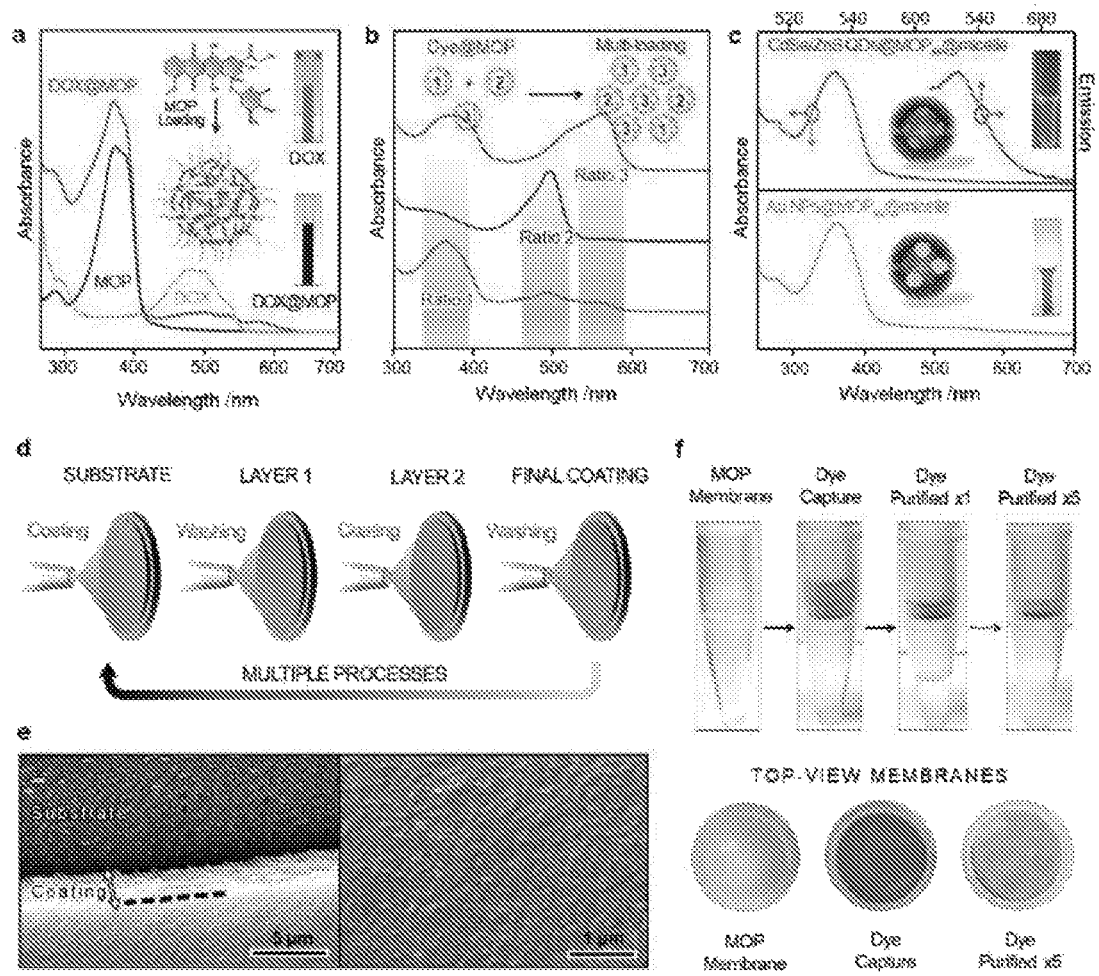
FIGS. 3A-3F. A) UV-vis spectra of free DOX, free $Pd_{24}L_{48}$-$C_{12}$ MOP, and DOX@$Pd_{24}L_{48}$-$C_{12}$ MOP in DMSO solution. B) UV-vis spectra of the multiple dye-loaded $MOP_{sa}$@micelles with different dye loading ratios. C) UV-vis and emission spectra of CdSe/ZnS QDs@$MOP_{sa}$@micelles and UV-vis spectrum of Au NPs@$MOP_{sa}$@micelles. The insets show the corresponding optical fluorescent and optical images. D) Schematic illustration of the fabrication of MOP superassembly-based separation membrane. E) SEM images of the MOP superassembly-based coating on a porous polypropylene-based substrate. F) The use of $Pd_{24}L_{48}$-$C_{12}$ MOP superassembly-based membrane for sulforhodamine B separation.
Figure 12:
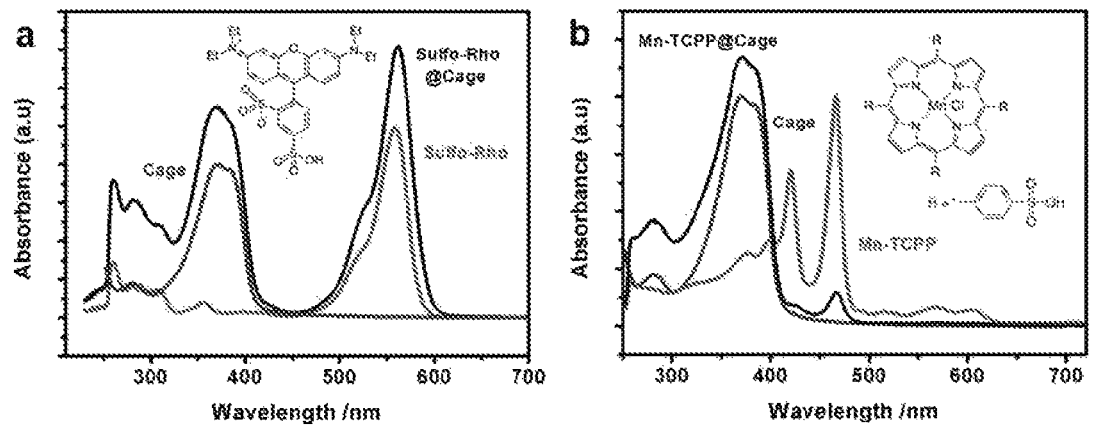
FIG. 12A-12B. UV-Vis spectra of the dye-loaded $Pd_{24}L_{48}$-$C_{12}$ MOP and free dyes: (a) sulforhodamine B and (b) Mn-TCPP.

The loading number of guest molecules inside $Pd_{24}L_{48}$-$C_{12}$ MOP was determined by UV-vis spectroscopy. The fitting of the absorbance versus the concentration of the guest molecules and $Pd_{24}L_{48}$-$C_{12}$ MOP was first carried out. The characteristic absorption wavelengths of $Pd_{24}L_{48}$-$C_{12}$ MOP and the guest molecules (DOX, sulforhodamine B, and Mn(III)tetra (4-sulfonatophenyl) porphyrin) were found to be 365, 503, 561, and 467 nm, respectively. As shown in FIG. 3a and FIG. 12, the MOP of $Pd_{24}L_{48}$-$C_{12}$ displayed no absorption at the characteristic absorption peak positions observed for the guest molecules. From the UV-vis spectra of the guest molecule-loaded $MOP_{sa}$@micelles, the concentration of various guest molecules can be determined. After subtraction of the absorption at 365 nm, originating from the guest molecules, the residual absorption at 365 nm that is attributed to the adsorption of $Pd_{24}L_{48}$-$C_{12}$ cage can be used further for cage concentration fitting. Based on the above couple of steps, the loading number of the guest molecules inside $Pd_{24}L_{48}$-$C_{12}$ MOP can be determined.

Separation Membrane Fabrication

A microtube that contains porous polypropylene membrane was used. 100 μL $Pd_{24}L_{48}$-$C_{12}$ MOP@micelle (1 mg mL$^{-1}$) solution was added into the microtube and then centrifuged at 10,000 rpm for 10 minutes. This coating process was repeated for a couple of times until the desired thickness was achieved. During each coating, the membrane was washed by water once.

Hemolysis Assay

The purified red blood cells (RBCs) were incubated with different concentrations of particles at room temperature for 3 h in continuous rotating state. Double distilled (DI) water and 1×PBS containing purified RBCs were used as the positive and negative controls, respectively. Finally, the mixtures were centrifuged at 300 g for 3 minutes, and 100 μL supernatant of all samples was transferred to a 96-well plate. The absorbance of hemoglobin in the supernatant was measured by a BioTek microplate reader (Winooski, VT) at 540 nm. The hemolysis percentage of each sample was determined using the reported equation.[2] Percent hemolysis (%)=100×(Sample $Abs_{540\ nm}$−Negative control $Abs_{540\ nm}$)/(Positive control $Abs_{540\ nm}$/Negative control $Abs_{540\ nm}$).

Drug Release

For the drug release studies, 2 mg of DOX-loaded $MOP_{sa}$@micelle in 1.2 mL PBS buffer solution (pH 7.4 or 5.5) was loaded into a small tube at room temperature. During each time interval, the nanoparticles were centrifuged (20,000 rpm, 10 minutes), and half of the supernatant solution was withdrawn, followed by the addition of 0.6 mL fresh PBS buffer. The content of DOX was determined by UV-vis titration.

Cell Culture

Cell culture was performed using standard procedures (atcc.org). For adherent cells, HeLa (CCL-2) and A549 (CCL-185) were obtained from American Type Culture Collection (ATCC) and respectively stored in DMEM and F-12K media containing 10% FBS at 37° C. and 5% $CO_2$. Cells were passaged at approximately 80% confluency. For coating purposes, living adherent cells (HeLa and A549) were removed from plate bottom using Trypsin-EDTA (0.25%) and then suspended in culture media.

Cell Viability Testing

Cell viability of the constructed nanocarriers was assessed by CellTiter-Glo 2.0 assay. Briefly, single-MOP@micelle or MOP$_{sa}$@micelle nanocarriers were first diluted to a concentration of 50000 cells mL$^{-1}$. Then, 100 μL of the samples was added into a white 96-well plate. Subsequently, 100 μL CellTiter-Glo 2.0 reagent was dispensed into each well. The luminescence was recorded 10 minutes after addition of CellTiter-Glo 2.0 reagent by a BioTek microplate reader. Cell viability was calculated as a percentage of mammalian cells in the absence of nanocarriers.

Anti-EGFR Modification

First, polyoxyethylene (23) lauryl ether, DSPE-PEG-biotin, and DSPE-PEG were mixed at mol % ratio of 92:4:4, and then dried under high vacuum to remove the organic solvent. Then, the dried film was hydrated in 1×PBS, and the bath was sonicated for 30 minutes to obtain a micelle solution at a concentration of 1 mg mL$^{-1}$. Then, 150 μL fluorescent dye labeled Pd$_{24}$L$_{48}$-C$_{12}$ MOP in DMSO was added to the micelle solution, followed by sonication to promote MOP super-assembly. The obtained MOP$_{sa}$@micelle-based nanocarriers were washed with 1×PBS twice. For anti-EGFR modification, 200 μL neutravidin protein (3 mg mL$^{-1}$) was added to the nanocarriers. After incubation for 30 minutes, the particles were centrifuged (20,000 rpm, 10 minutes), and the supernatant was removed. After redispersion in 1×PBS, 200 μL biotin-EGFR (0.2 mg mL$^{-1}$) was added and incubated at room temperature for 30 minutes. After washing with 1×PBS twice and redispersion in 100 μL PBS, the antibody-conjugated nanocarriers can be directly used for in vitro targeting experiments.

In Vitro Targeting

For the studies, 2×10$^5$ A549 (CCL-185, ATCC) cells in 6-well plates with 2 mL F-12K media containing 10% FBS and 1% PS were seeded and then incubated at 37° C. in 5% CO$^2$-humidified atmosphere. After 24 hours, the media was removed and replaced with 1 mL fresh complete cell culture media supplemented with 50 μg mL$^{-1}$ of EGFR-modified or unmodified MOP$_{sa}$@micelles for different times at 37° C. under 5% CO$_2$-humidified atmosphere. After incubation, the media was removed, and the cells were gently washed twice with 1×PBS. For imaging purposes, the treated cells were fixed in 4% paraformaldehyde (in 1×PBS) at room temperature for 15 minutes, washed with 1×PBS twice, and then stored in 1 mL 1×PBS. The cell nuclei and F-actin were stained with 1 mL Hoechst 33342 (3.2 μM 1×PBS) for 30 minutes and 200 μL Alexa Fluor488 phalloidin (20 nM in 1×PBS) for 45 minutes, respectively. After staining, the cells were washed with 1×PBS twice and stored in 1×PBS prior to fluorescence microscope imaging.

Pharmacokinetics and Biodistribution Studies

All the animal procedures complied with the guidelines of the University of New Mexico Institutional Animal Care and Use Committee and were conducted following institutional approval (Protocol 17-200658-HSC). The experiments were performed on female Albino C57BL/6 mice (6 weeks). To evaluate the circulation half-life, 150 μL of CdSe/ZnS QD (627 nm)-labeled MOP$_{sa}$@ micelles (1 mg/mL) were injected into the eye of the mice. The blood was collected at 0.5, 1, 2, 6, 12, 24, and 48 hours following the injection. Each time point group contained three mice. The collected blood samples were diluted with the same amount of 1×PBS before fluorescence measurement. Particle retention in circulation at these time points was determined by measuring the fluorescence on a BioTek microplate reader (Winooski, VT). Pharmacokinetics parameters were calculated to fit a non-compartment model.

To study the related biodistribution in various tissues, 150 μL of CdSe/ZnS QD (627 nm)-labeled MOP$_{sa}$@ micelles (1 mg/mL) were retro-orbital injected to mice. At each of the 6, 12, 24, and 48 hours time points following the NP injection, three mice were randomly selected and euthanized. Their spleen, liver, heart, lung, and kidneys were collected. The collected organs were examined with an IVIS fluorescence imaging system (Xenogen, Alameda, CA), and the fluorescence intensity of the MOP particles in different organs was further semi-quantified by the IVIS imaging software.

Results

The superassembly of MOP is described herein. The fabrication technique affords a simple synthesis process and the organization of individual MOP to form advanced hierarchical structures. Specifically, the superassembly of MOP supported micelles (MOP$_{sa}$@micelle) for targeted drug delivery is described (see Scheme 1a in FIG. 1). The key fabrication point is the decoration of the outer surface of the MOP with hydrophobic chains to transform MOP units into nanobuilding blocks that can self-assemble into larger and well-defined superassemblies within micelles. This approach is different from the reported molecular building block (MBB) approach that is used to construct metal-organic framework (MOF)-based lipid bilayers (Zhu et al., 2018), where the open metal sites of MOF units allow further coordination of additional organic ligands to form MOF NPs (Scheme 1b in FIG. 1). Nonetheless, the MBB approach typically affords limited size control, whereas the superassembly approach described herein provides homogeneous size distributions in broad ranges of diameters through the simple control of the MOP concentration to obtain ultrasmall single MOP@micelle and MOP$_{sa}$@micelle. In addition, owing to the highly porous nature of the MOP, various cancer drugs were controllably loaded into individual MOP units with high payloads and subsequently integrated into MOP superassemblies to form multiple drug delivery systems. Furthermore, the MOP superassembly approach enabled the modular assembly of MOPs with additional functional NPs such as fluorescent quantum dots (QDs) for multifluorescence imaging or gold NPs for enhanced bioimaging. To demonstrate the potential of the MOP superassembly concept for drug delivery, a Fujita-type MOP composed of dozens of dodecyl chains was chosen as a prototype. A dose-dependent assay for MOP$_{sa}$@micelles of different sizes demonstrated negligible hemolytic activities and long-term colloidal stability in various media, thereby mitigating possible concerns of structure disassembly during circulation. Cell viability tests further demonstrated the good biocompatibility of the MOP$_{sa}$@micelles that is related to the NP size and the molecular weight of the polyethylene glycol (PEG) that was used for surface modification. Importantly, designing MOP$_{sa}$@micelle nanocarriers with targeting moieties enabled targeted cancer cell delivery and in vivo experiments using a mouse model also confirmed the good circulation. Taken together, this novel and modular superassembly approach combines the synergistic advantages of micelles (e.g., low inherent toxicity and long circulation time) and the MOP superassembly (e.g., highly controlled architecture, stability, and high payloads of multiple cargos), and promotes the design of MOP-inspired nanocarriers for targeted cancer therapies.

Figure 6:
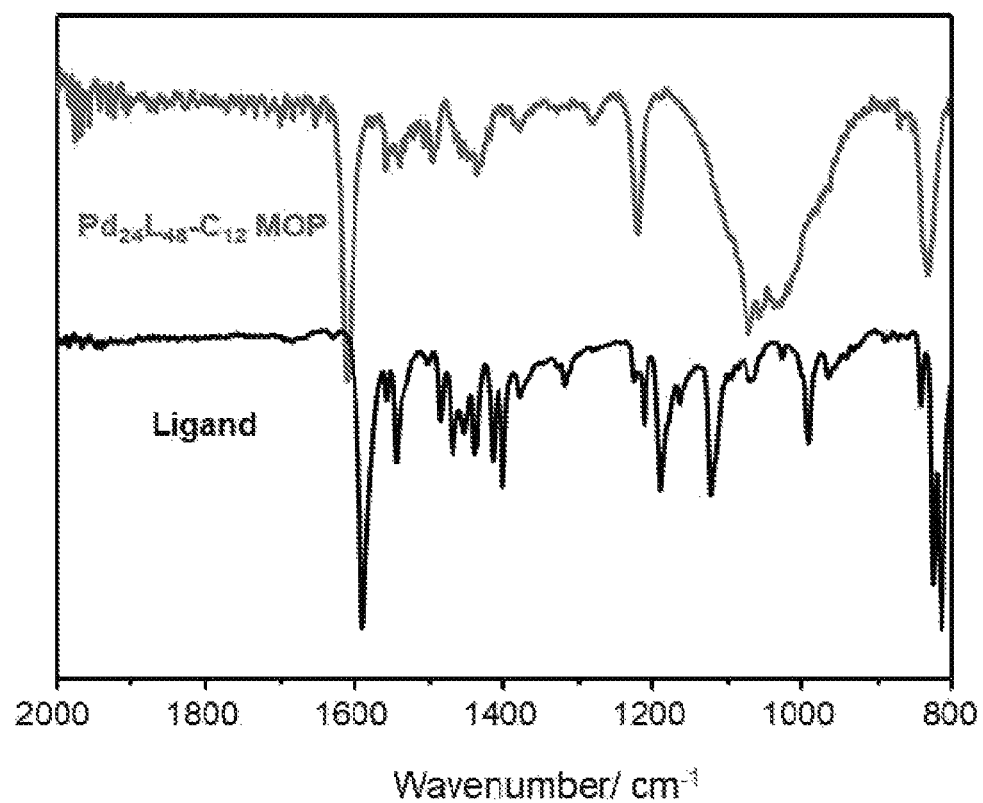
FIG. 6. Fourier transform infrared spectrophotometry (FT-IR) of organic ligand and the formed $Pd_{24}L_{48}$-$C_{12}$ MOP.
Figure 7:
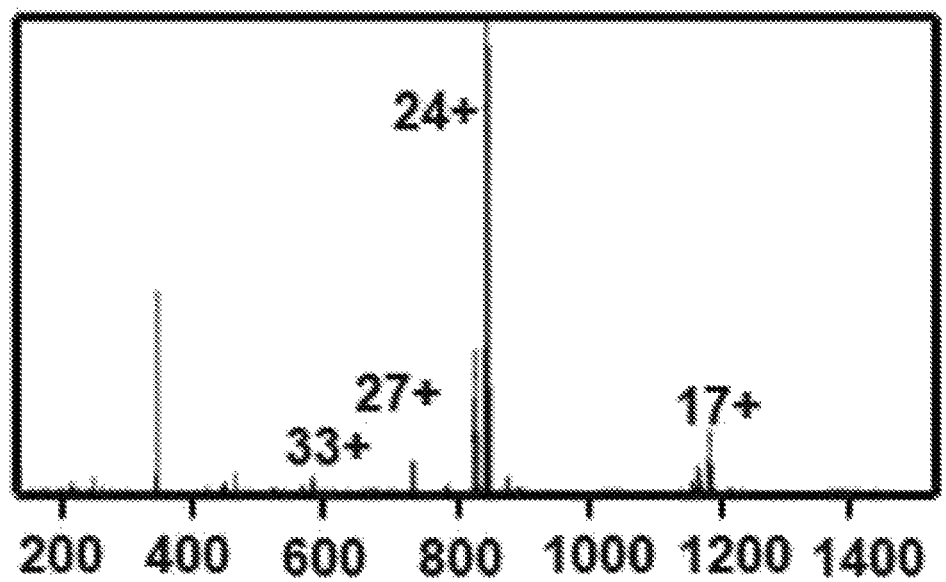
FIG. 7. Electrospray ionization mass spectrometry pattern of the molecular cage $Pd_{24}L_{48}$ with no hydrophobic alkane chains decoration.
Figure 8:
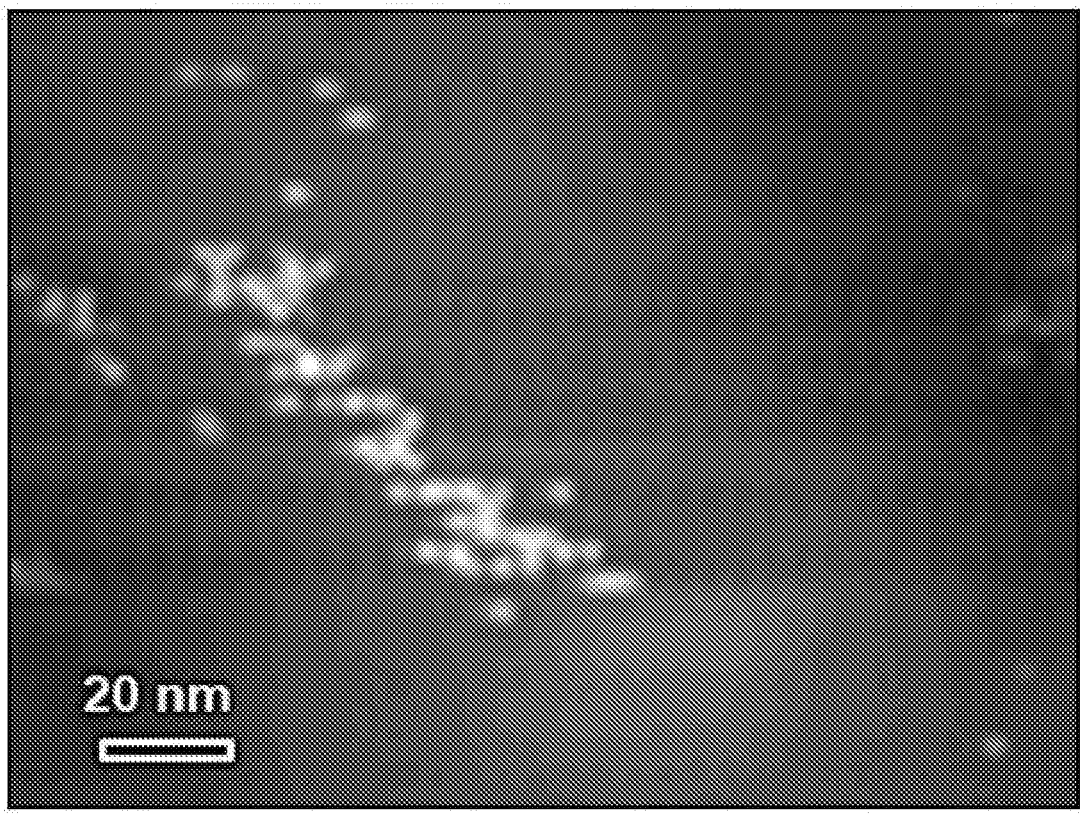
FIG. 8. AFM image of the molecular cage $Pd_{24}L_{48}$-$C_{12}$ MOP on silicon substrate.
Figure 9:
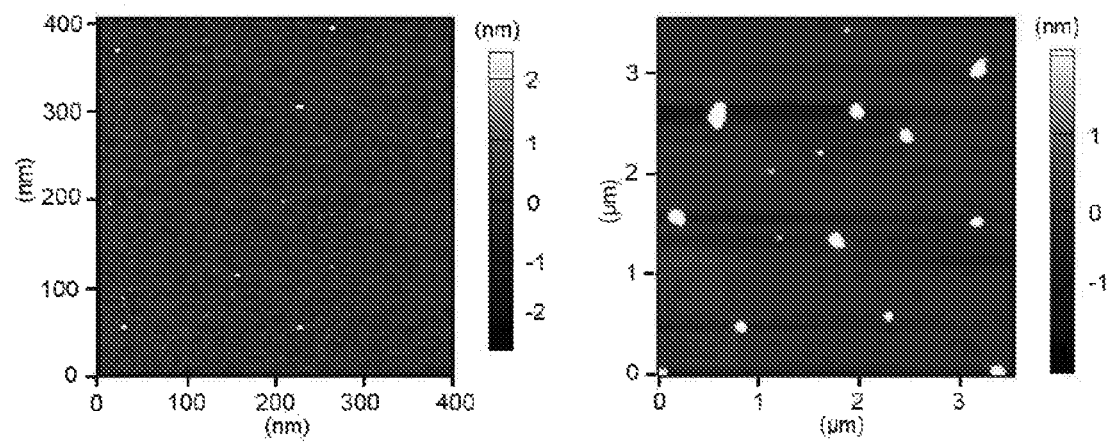
FIG. 9. AFM images of $MOP_{sa}$@micelles with different sizes.

A giant Pd$_{24}$L$_{48}$ Fujita-type spherical framework (≈7.2 nm) composed of up to 48 decorations of dodecyl chains (denoted as Pd$_{24}$L$_{48}$-C$_{12}$) was first prepared for proof of concept (FIG. 1a) (Sun et al., 2016). Dipyridyl-3-dodecylthiophene was first synthesized as an organic linker (ligand 1) using the Suzuki-Miyaura reaction. To prepare the coordination sphere, ligand 1 (0.1 mmol) and Pd(BF$_4$)$_2$ (50 µmol) were heated in a mixture of acetonitrile and chloroform at 70° C. for 24 hours. Then, an excess amount of a mixed solution of ethyl acetate and diethyl ether (1:1 v/v) was added to promote the precipitation. The structure of Pd$_{24}$L$_{48}$-C$_{12}$ MOP was first determined by Fourier-transform infrared spectroscopy. As shown in FIG. 6, the characteristic peak at 1589 cm$^{-1}$ assigned to the vibration of C=N in the pyridine ring was shifted to 1610 cm$^{-1}$, indicating the coordination of Pd$^{2+}$ metal ions. Based on chemical analysis, the ratio of organic ligand to Pd$^{2+}$ was calculated to be ≈1.8, which is close to the exact ratio of 2. Moreover, in nuclear magnetic resonance (NMR) spectra (FIG. 1B), the b and c protons of the pyridyl or thiophene groups (H$_b$ and H$_c$) were shifted downfield by 0.20 and 0.22 ppm, respectively, upon coordination to Pd$^{2+}$. Compared with the $^1$H signal of free ligand 1, the $^1$H signal of Pd$_{24}$L$_{48}$-C$_{12}$ MOP was much broader. Diffusion-ordered NMR measurements also demonstrated a single product given the diffusion coefficient of 5.7×10$^{-10}$ m$^2$ s$^{-1}$, which was indicative of the formation of larger chemical species. Furthermore, electrospray ionization and matrix-assisted laser desorption ionization time of flight mass spectrometry techniques were used to confirm the coordination structure. Although the molecular weight of the Pd$_{24}$L$_{48}$ cage was determined by a series of prominent peaks in [Pd$_{24}$L$_{48}$-(BF$_4^-$)$_m$]$^{m+}$ (m/z=17, 24, 27, and 33; FIG. 7), the molecular weight of the Pd$_{24}$L$_{48}$-C$_{12}$ cage could not be quantified by the same technique, presumably due to presence of the multiple dodecyl chains. Nevertheless, high-resolution transmission electron microscopy (HR-TEM) displayed a dense packing of Pd$_{24}$L$_{48}$-C$_{12}$ MOPs with a distance of 4.8 nm between closest neighbors (FIG. 1C). Atomic force microscopy (AFM) imaging also showed single cages with sizes of ≈5.0 nm (FIG. 8). All this structural information confirmed the successful formation of giant coordination spheres. Based on molecular mechanics (MM) calculations, the optimized structure of Pd$_{24}$L$_{48}$-C$_{12}$ was obtained. As shown in FIG. 1D, the rhombicuboctahedral structure of Pd$_{24}$L$_{48}$-C$_{12}$ is highly spherical with an inscribed sphere with a diameter of 3.6 nm and a circumscribed sphere, with alkane chains, of 7.2 nm in diameter. The distance between antipodal palladium atoms was measured to be 4.0 nm.

Figure 2:
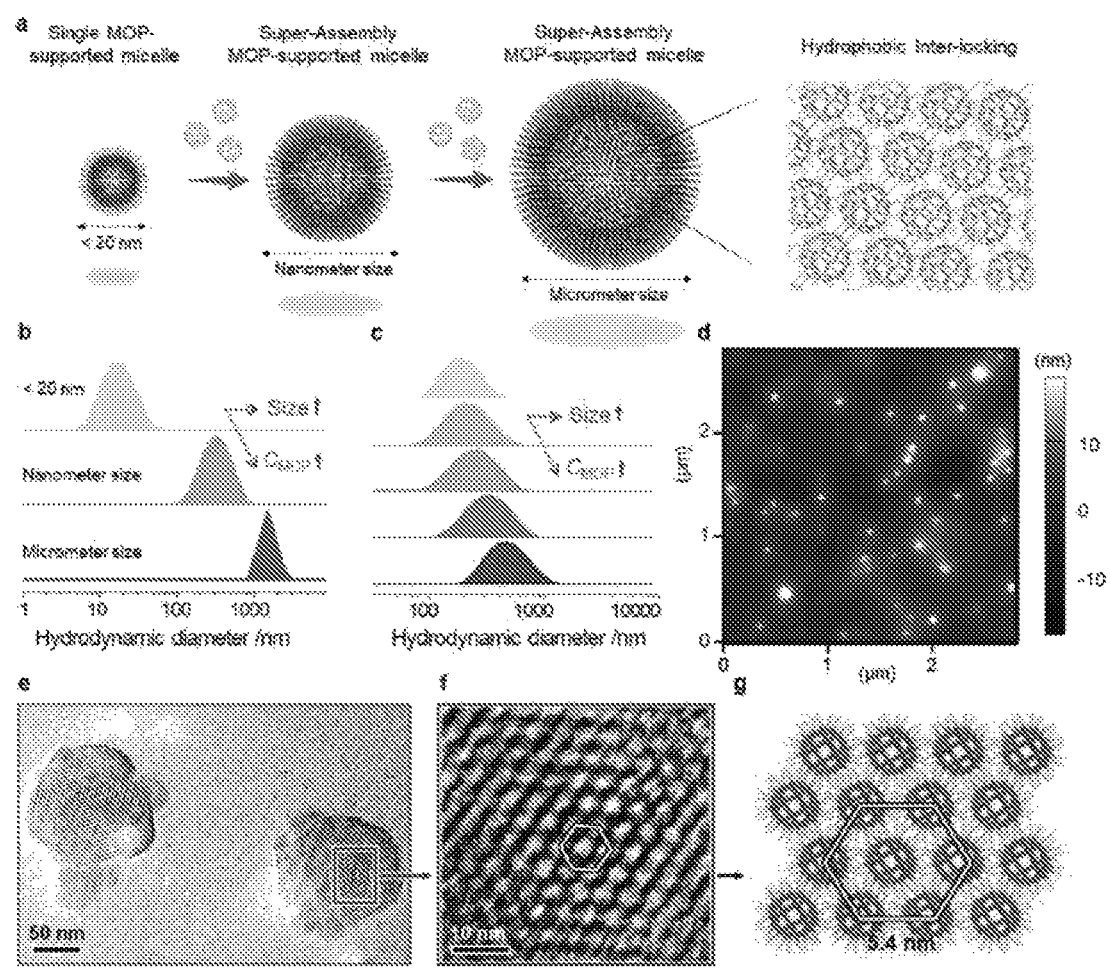
FIGS. 2A-2G. A) Schematic illustration of the construction of single MOP@micelle and $MOP_{sa}$@micelles with different size scales. B) DLS data of $Pd_{24}L_{48}$-$C_{12}$ MOP-supported micelles with ultrasmall, nanometer, and micrometer sizes. C) DLS data showing size control of MOPsa@micelles. D) AFM images of $MOP_{sa}$@micelles with nanometer size. E,F) HR-TEM images and G) simulated structure of the dense packing of $Pd_{24}L_{48}$-$C_{12}$ MOP in the superassembly.
Figure 10:
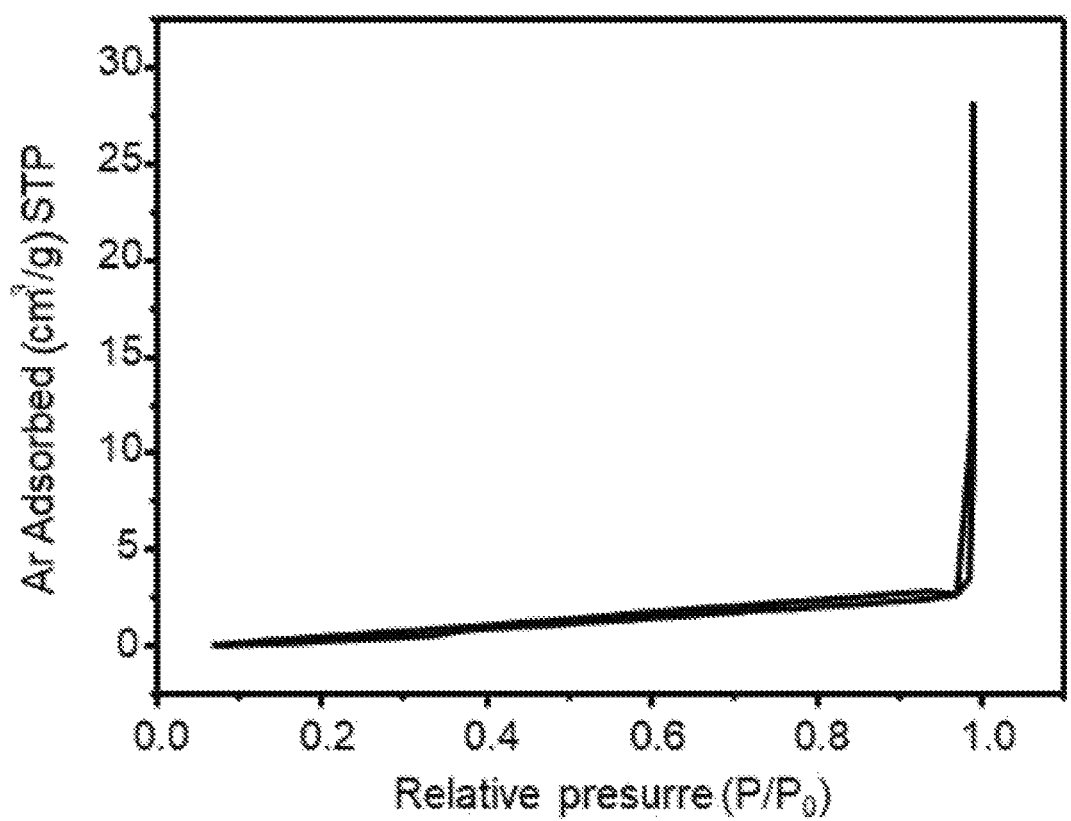
FIG. 10. Ar sorption isotherm of the $MOP_{sa}$@micelle.

Subsequently, the preparation of single MOP@micelle NPs followed by MOP superassembly was performed using the Pd$_{24}$L$_{48}$-C$_{12}$ MOP nanobuilding blocks. First, to promote the superassembly of the hydrophobic Pd$_{24}$L$_{48}$-C$_{12}$ MOP cages in an aqueous solution, a micellar solution assembled by polyoxyethylene (6) lauryl ether (P$_6$LEL) was added (FIGS. 1A,E,F). A small drop (1 µL) of an MOP solution (0.17×10$^{-3}$ m in dimethyl sulfoxide (DMSO)) was added to the micellar solution, and the resulting mixture was sonicated to promote the formation of single MOP-supported micelle NPs (FIG. 2A). High-magnification darkfield scanning transmission electron microscopy (STEM) of the superassembly showed uniform sizes of 4.2±0.7 nm (FIG. 1E), well correlated with the molecular shell of Pd$_{24}$L$_{48}$-C$_{12}$ MOP defined by the coordinated palladium ions. The hydrodynamic diameters of the micelle and MOP-micelle conjugate were determined by dynamic light scattering (DLS) to be 13.6 and 18.8 nm (FIG. 1F), respectively. These data confirm the successful formation of single MOP-supported micelles. Moreover, with the increase of MOP concentration, larger MOP superassemblies with nanometer or micrometer sizes were generated (FIGS. 2A,B). Notably, the size could easily be tuned in a broad range by gradually increasing the MOP concentration (FIG. 2C). The monodisperse particle size distributions of the single MOP-supported micelle (6.8±0.6 nm) and MOP superassemblies (65.8±4.8 and 100.4±14.6 nm) were further confirmed by AFM images (FIG. 2D; FIG. 8). TEM imaging of the air-dried samples revealed a hexagonal packing of MOPs inside the superassemblies with a long-range order on a scale of 100 nm×100 nm (FIG. 2E). The enlarged image shown in FIG. 2F reveals the overlaying hexagons with a 5.4 nm dimension. The hydrophobic interactions from the long alkane chains of closest MOPs are presumably the main driving force for the superassembly of MOP and may as a result lead to high stability during in vivo circulation. The surface area and pore volume of the MOP$_{sa}$@micelle NPs were found to be inaccessible using standard argon adsorption-desorption measurements due to the kinetically closed pore of the cages and shell blocking effect as a result of dense packing of the long PEG chains (FIG. 10) (Park et al., 2014).

Figure 11:
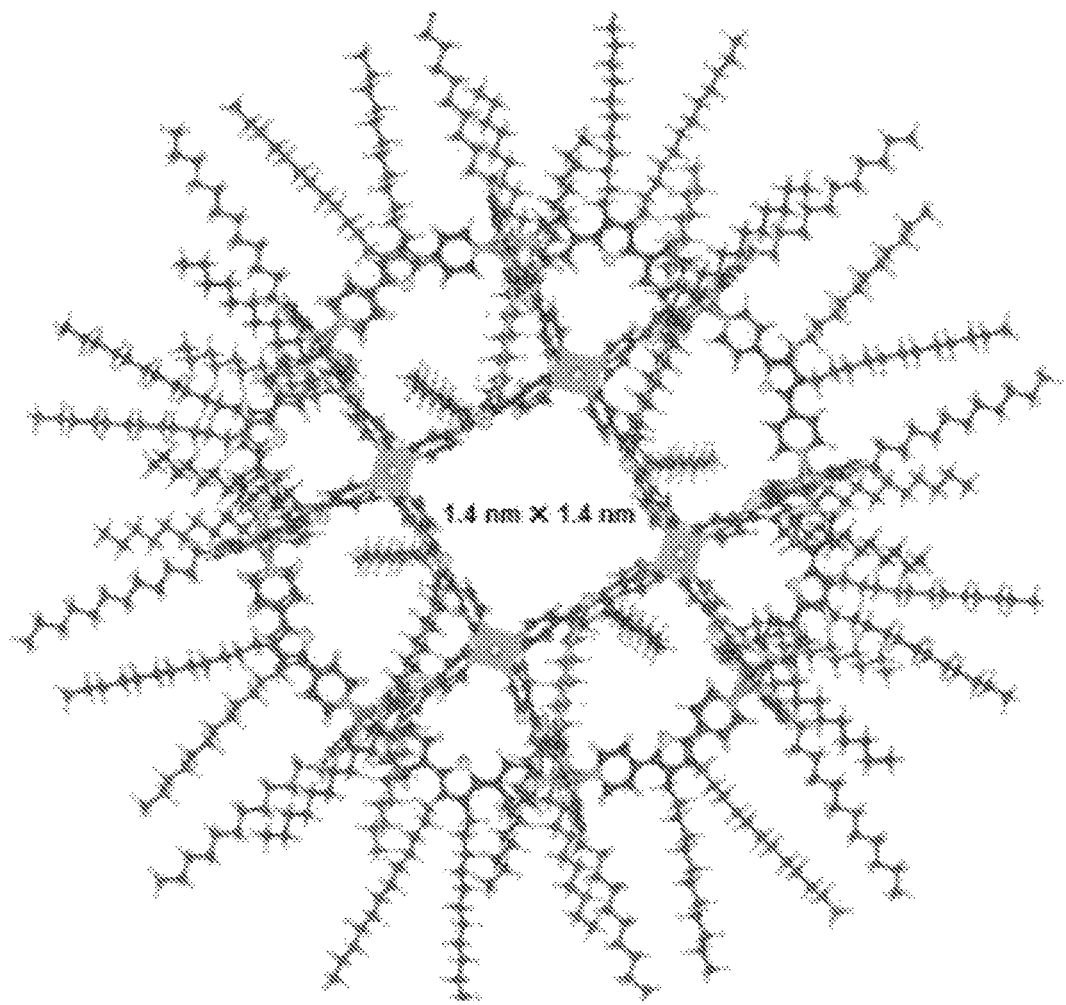
FIG. 11. Optimized structure of $Pd_{24}L_{48}$-$C_{12}$ MOP based on molecular mechanics calculation with a relative large pore window of 1.4 nm×1.4 nm.
Figure 13:
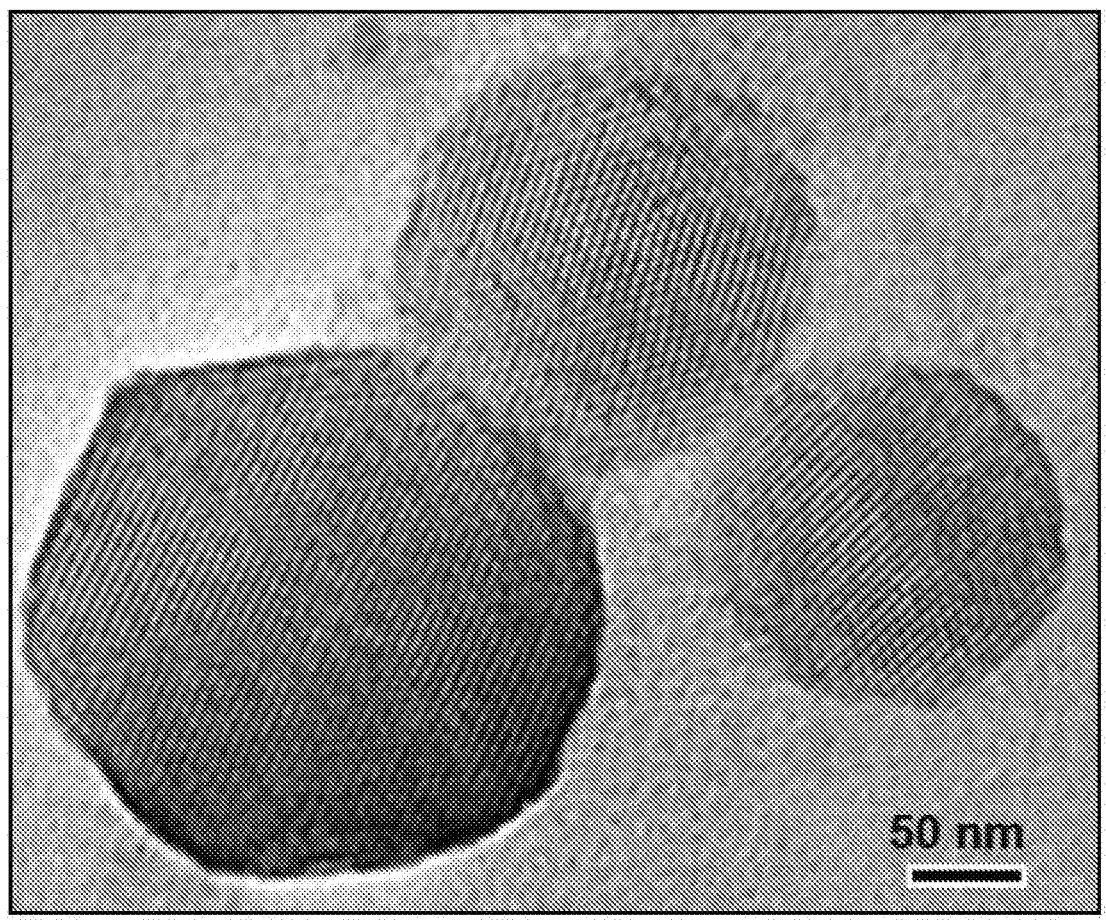
FIG. 13. TEM image of DOX-loaded $MOP_{sa}$@micelle.

The cargo loading capabilities of the MOP$_{sa}$@micelle nanomaterials were then investigated. The high inherent porosity of Pd$_{24}$L$_{48}$-C$_{12}$ as well as the relatively large pore windows (1.4 nm×1.4 nm) of the cages (FIG. 11) suggested that various guest molecules could be loaded into the MOP nanocavity in a controlled manner. To evaluate the cargo loading capacities of our nanocarriers, three types of molecules were separately loaded, including doxorubicin hydrochloride (DOX.HCl) as a hydrophilic drug for chemotherapy, sulforhodamine B as a fluorescent dye for labeling, and Mn(III)tetra (4-sulfonatophenyl) porphyrin (MnTPPS$_4$) as a contrast agent for magnetic resonance imaging. The successful loading of the guest molecules was confirmed in the particles after cargo loading by the characteristic absorption bands of the guest molecules displayed in the UV-vis spectra (see 503, 561, and 467 nm in FIG. 3A and FIG. 12). Based on calculations from the UV-vis spectra, one Pd$_{24}$L$_{48}$-C$_{12}$ MOP entity was estimated to be loaded with 22 DOX.HCl, 38 sulforhodamine B, and 13 MnTPPS4, confirming the high loading efficacy. Note that the structure of the cargo-loaded MOP$_{sa}$@micelle nanocarriers remained unaffected by the cargo loading (see TEM image in FIG. 13). In addition, multiple guest molecules were loaded within individual MOP, which were then superassembled simultaneously with a highly controlled molar ratio. For instance, three fluorescent molecules (6-aminocoumarin, fluorescein isothiocyanate, and sulforhodamine B) were individually loaded into different Pd$_{24}$L$_{48}$-C$_{12}$ MOP samples and then integrated into MOP superassemblies with tunable sample ratios for potential multifluorescence imaging, as confirmed by UV-vis spectroscopy (FIG. 3B). This controllable superassembly scheme provides a powerful approach to prepare multidrug delivery nanosystems with precise control of the ratio for each drug by simply tuning the MOP sample ratios.

Figure 14:
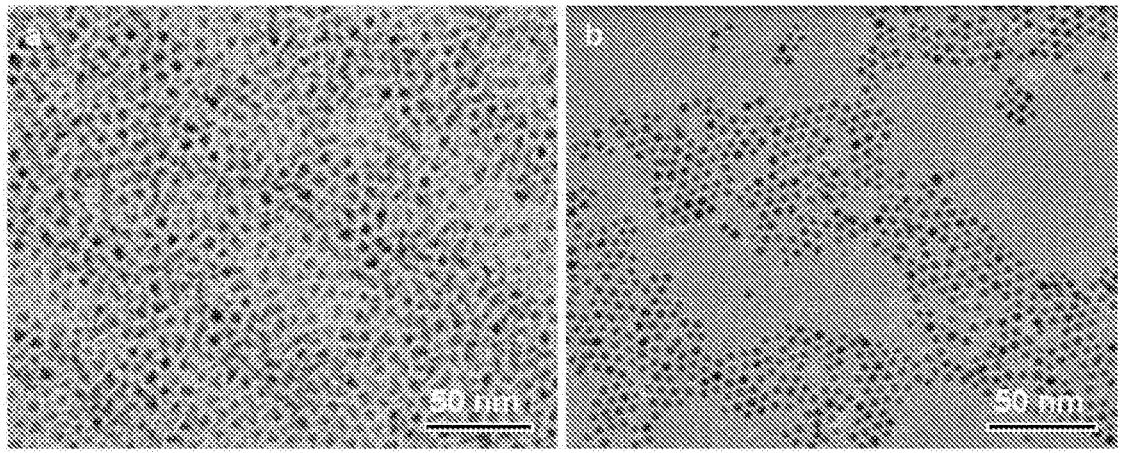
FIGS. 14A-14B. TEM image of the commercial CdSe/ZnS quantum dots (A) and the synthesized Au NPs (B).
Figure 15:
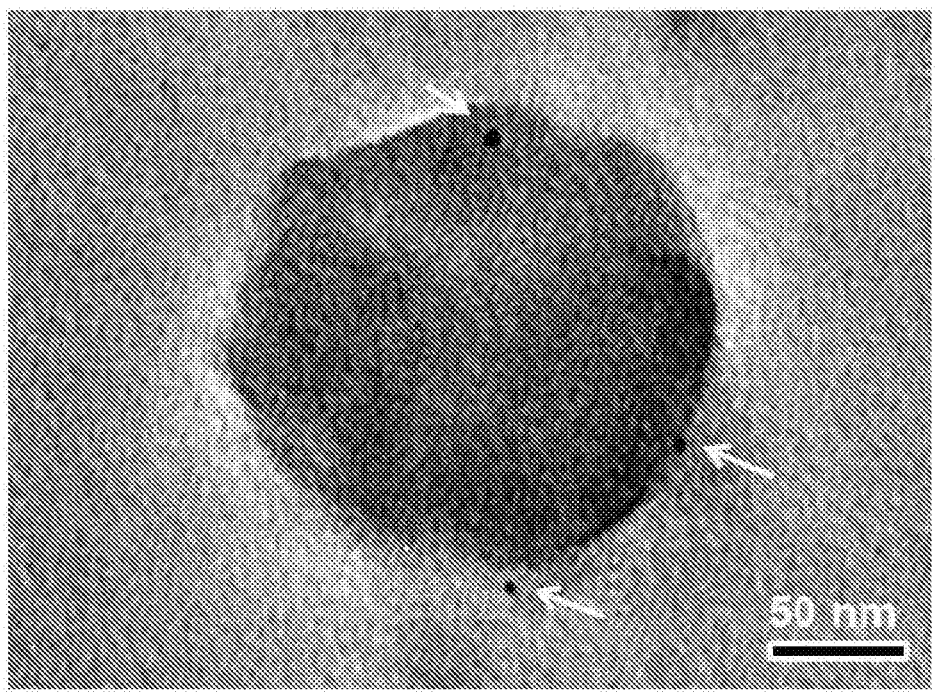
FIG. 15. TEM image of the Au NPs@$MOP_{sa}$@micelle. The Au NPs were pointed out by arrows.
Figure 16:
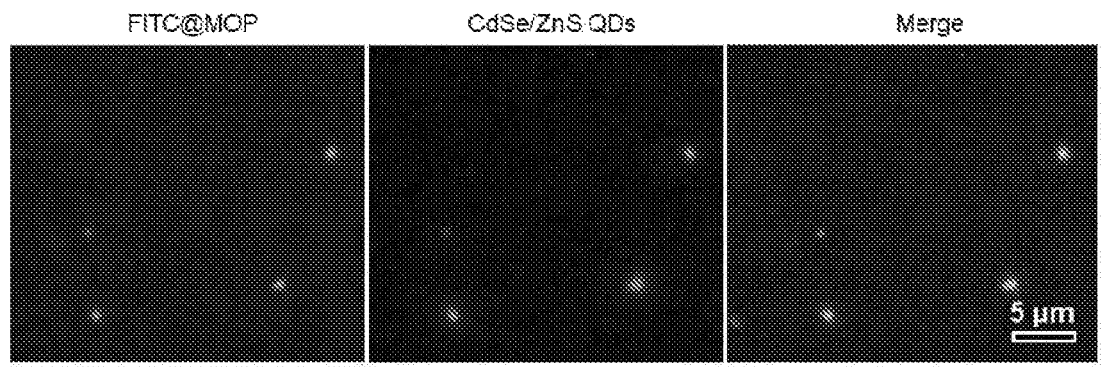
FIG. 16. Fluorescent image of the CdSe/ZnS quantum dot@$MOP_{sa}$@ micelles with fluorescein isothiocyanate dye previously loaded in MOP nanocavities. The overlapping of the fluorescent points from different channels confirms the successful doping of quantum dots in $MOP_{sa}$@micelles.
Figure 17:
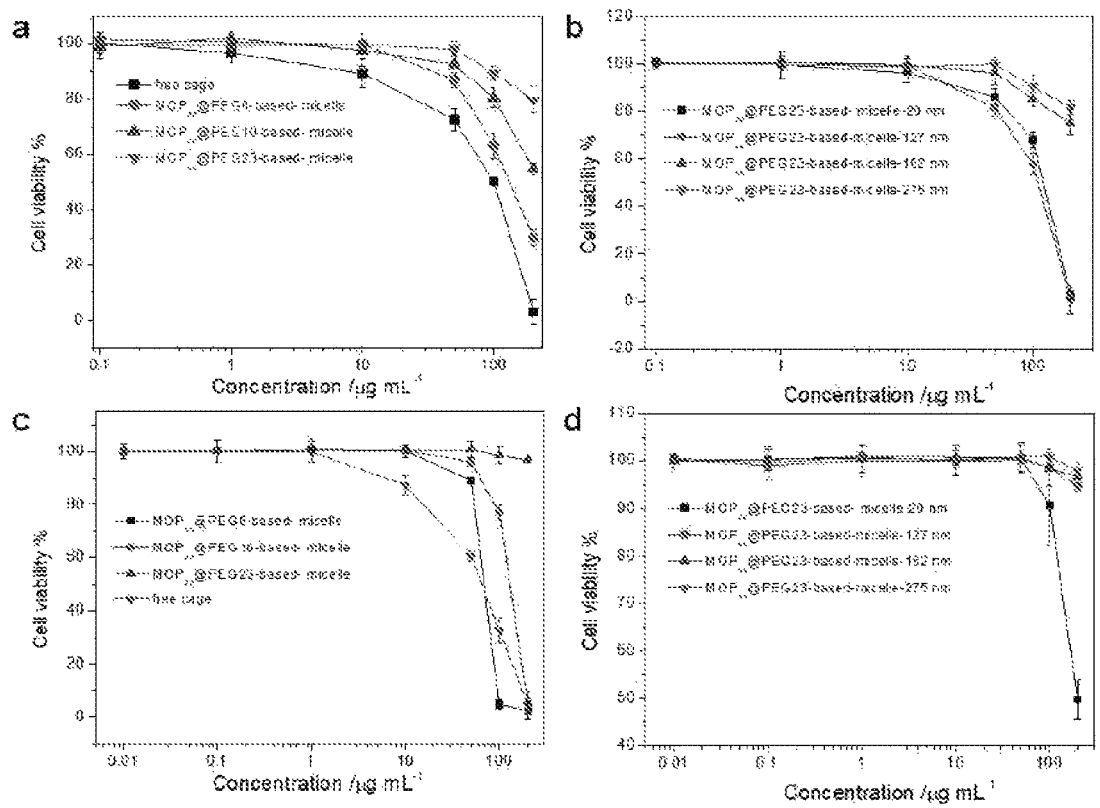
FIGS. 17A-17D. Cytotoxicity profiles of single MOP-supported micelle and MOP super-assembly-supported micelles with different PEG chain lengths and sizes against (A,B) A549 and (C,D) HeLa cells.

The superassembled MOP-micelle particles were then incorporated with functional materials and nanomaterials for a range of proof-of-concept studies. First, several functional nanomaterials, such as fluorescent QDs and gold nanomaterials (FIG. 14), were incorporated into the MOP$_{sa}$@micelle carriers via one-pot during the superassembly of MOP—micelle nanocarriers. As depicted in FIG. 3C, the fluorescent peak at 627 nm for CdSe/ZnS quantum dot@ MOP$_{sa}$@micelle and the typical plasmon resonance peak at 529 nm for Au NPs@ MOP$_{sa}$@micelle confirmed the successful doping of the MOP$_{sa}$@micelle particles (FIGS. 16-17). Such incorporation of functional nanomaterials into the MOP$_{sa}$@micelle nanocarriers can diversify the utility and potential of the platform. Additionally, it was found that the MOP superassemblies could be deposited onto polypropylene membranes as prototypes for separation applications (FIG. 3D). The fabrication of the mixed membrane was realized with a controlled thickness of ≈2 μm, as shown by SEM (FIG. 3E). After five deposition cycles (FIG. 3D), a film consisting of a dense packing of MOP superassemblies was obtained and was then applied to separate mixtures. Owing to the porosity and the reversible host-guest interactions of MOPs, the resultant membrane showed promising separation properties for sulforhodamine B-containing solutions, even after a few cycles of separation (FIG. 3F). All of these results point to multifunctional MOP$_{sa}$@micelle nanocarriers and novel mixed membranes based on MOP nanocages for biomedical and separation applications.

Figure 4:
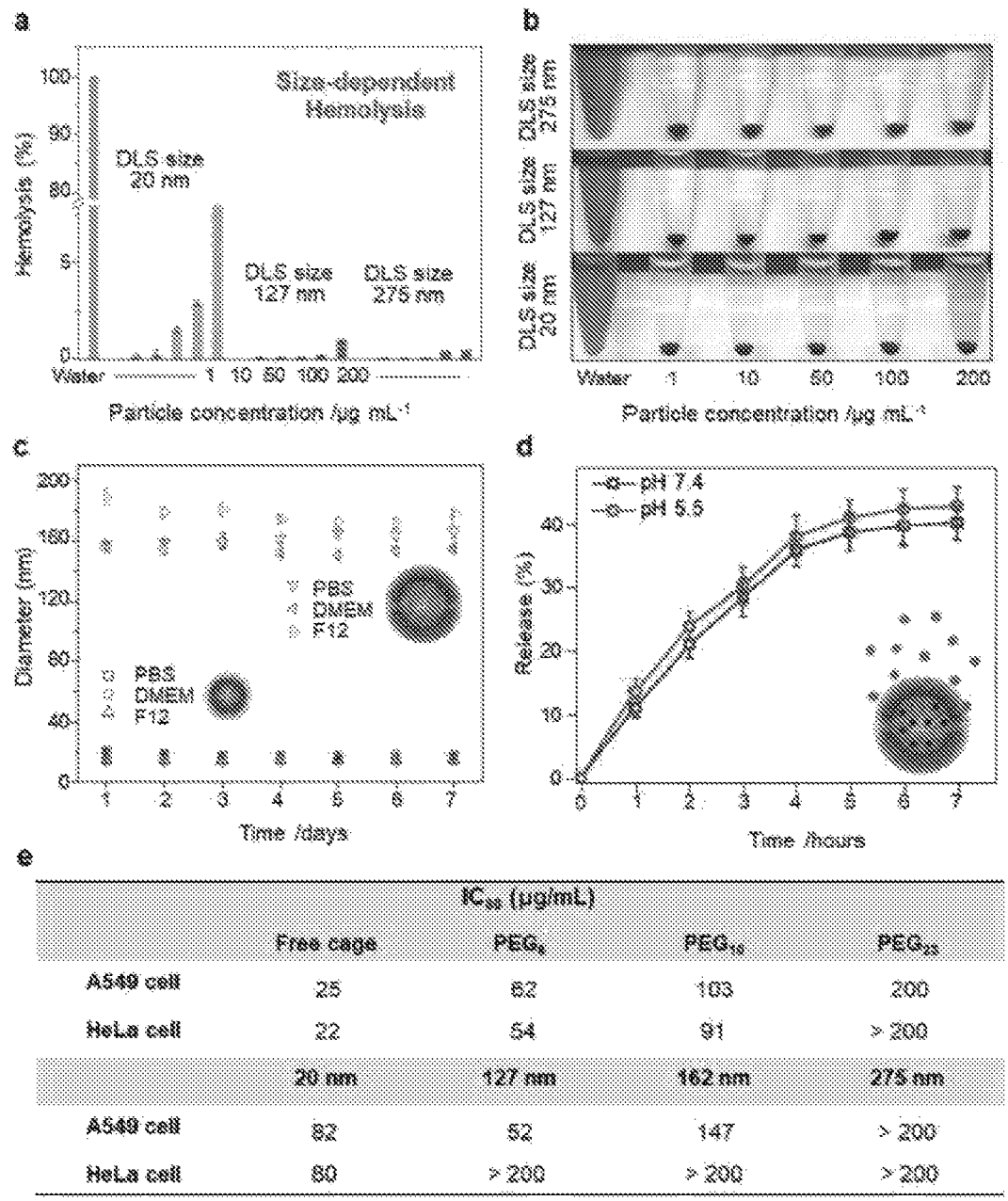
FIGS. 4A-4E. A) Percent hemolysis and B) photographs of human RBCs incubated with single MOP-supported micelle and MOP superassembly-supported micelles with different size scales. C) Long-term colloidal stability of various MOP superassembly-supported micelles in different media: PBS, DMEM, and F-12K at 25° C. D) Time-dependent drug (DOX) release behavior of MOP superassembly-supported micelles in PBS solution at different pH values. E) Cytotoxicity profiles of single MOP-supported micelle and MOP superassembly-supported micelles with different PEG chain lengths (size: ≈162 nm) and sizes ($PEG_{23}$-based) against A549 and HeLa cells.
Figure 18:
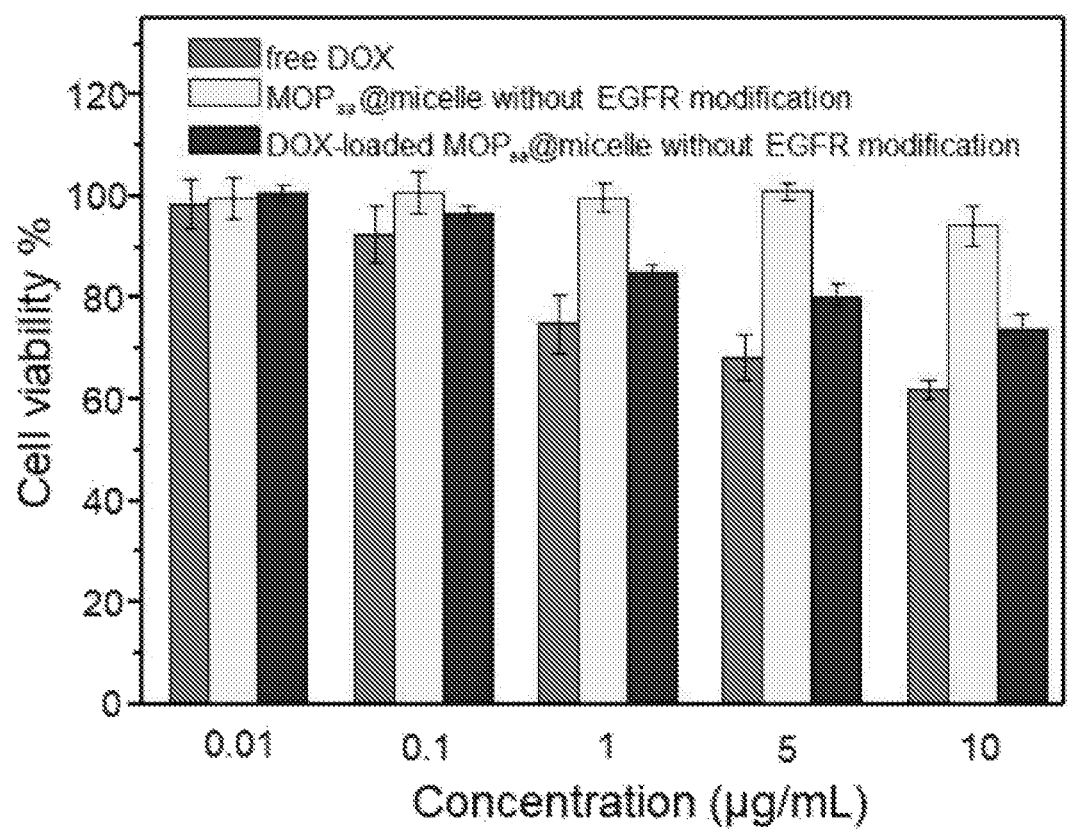
FIG. 18. Sustained viability of A549 cells after incubation of free DOX, MOP$_{sa}$@micelle without EGFR modification, and DOX-loaded MOP$_{sa}$@micelle without EGFR modification for 2 hours.

The biocompatibility and colloidal stability of the MOP$_{sa}$@ micelles were then studied in view of future biomedical applications. To evaluate the concentration-dependent lysis of red blood cells (RBCs), the nanomaterials were incubated with RBCs at concentrations varying from 1 to 200 μg mL$^{-1}$ in 1× phosphate-buffered saline (PBS) solution for 3 hours. As shown in FIGS. 4A-B, the hemolysis percentage of RBCs for all samples increased in a dose-dependent manner. The smaller single MOP@micelle carriers caused a higher release of hemoglobin than the larger carriers. The same trend was observed with mesoporous silica nanoparticles (Lin et al., 2010). Nevertheless, all of the nanocarriers showed negligible hemolytic activities, thus meeting the essential prerequisites of biomedical applications. The colloidal stabilities of the MOP$_{sa}$@ micelles were then tested in various media (PBS solution, Dulbecco's modified Eagle medium (DMEM), and F-12K). DLS data of the MOP$_{sa}$@micelle samples with different sizes showed narrow hydrodynamic size distributions with low PDI values of less than 0.2 (FIG. 4C). Notably, long-term exposure in various media (7 days) caused insignificant size changes, indicating long-term colloidal stability. It can be surmised that the polymeric PEG chains act as protective layers to prevent particle aggregation. The cytotoxicity profiles of the single MOP@micelle or MOP$_{sa}$@micelle-based nanocarriers with different PEG chain lengths and sizes were also evaluated against two human cancer cell lines: A549 cell (lung cancer cell) and HeLa cell (cervical cancer cell). The corresponding IC$_{80}$ values (concentration required to reduce cell viability to 80%) are summarized in FIG. 4e. As shown in FIG. 4E and FIG. 17, free nanometric MOP exhibited higher cytotoxicity (IC$_{80}$=25 μg mL$^{-1}$) on A549 cells than MOP superassemblies with different PEG chain lengths (6, 10, and 23) (IC$_{80}$=62, 103, and 200 μg mL$^{-1}$, respectively), thus confirming the low inherent toxicity of PEGylation. In addition, higher PEG repetitive unit numbers ranging from 6 to 23 led to considerably reduced cytotoxicity for the MOP superassemblies, which correlates with the reported molecular weight-dependent cytotoxicity of PEG samples (Pozzi et al., 2014). Additionally, size-dependent cytotoxicity effects were observed (FIG. 18). For ultrasmall single MOP@micelle particles, the IC$_{80}$ value (82 μg mL$^{-1}$) was much higher than that for MOP$_{sa}$@ micelles with larger sizes. In summary, increasing the particle size leads to reduced toxicity, and the high cell viabilities of all MOP@micelle-based nanocarriers (even at high concentrations) suggest the good biocompatibility of the hybrid nanocarriers developed herein for biomedical applications.

The potential of the biocompatible MOP—micelle carriers for cargo release was then tested in aqueous solution. The DOX drug was selected as it is a widely used anticancer drug. Drug release experiments were carried at room temperature in fresh PBS buffer solution at pH 7.4 and 5.5. The absorbances of the supernatant collected at fixed time intervals were measured to determine the amount of DOX released under these conditions. As displayed in the release profiles of FIG. 4D, nearly 36% of the total drug release at pH 7.4 and 5.5 occurred within the first 4 hours, and 5% more of the total drug was released after 7 hours. In this configuration of MOP and cargo, the pH had negligible influence on the release kinetics. Note that DOX may have quite strong host-guest interactions with Pd$_{24}$L$_{48}$-C$_{12}$ MOP due to collective, weak, noncovalent interactions. When the concentration of DOX inside the MOP cavity was high, the interactions between DOX and MOP may be weakened to a certain extent due to both DOX/DOX and DOX/MOP interactions. Following the release of DOX from the MOP cavity, there may be a balance between releasing and rebinding, which leads to only a partial release of loaded drugs. Nevertheless, given the versatility of MOP and drug structure, controllable release via stimuli-responsive MOPs (e.g., light) could be envisioned to promote the construction of smart drug delivery systems with higher extents of release (Han et al., 2013).

Figure 5:
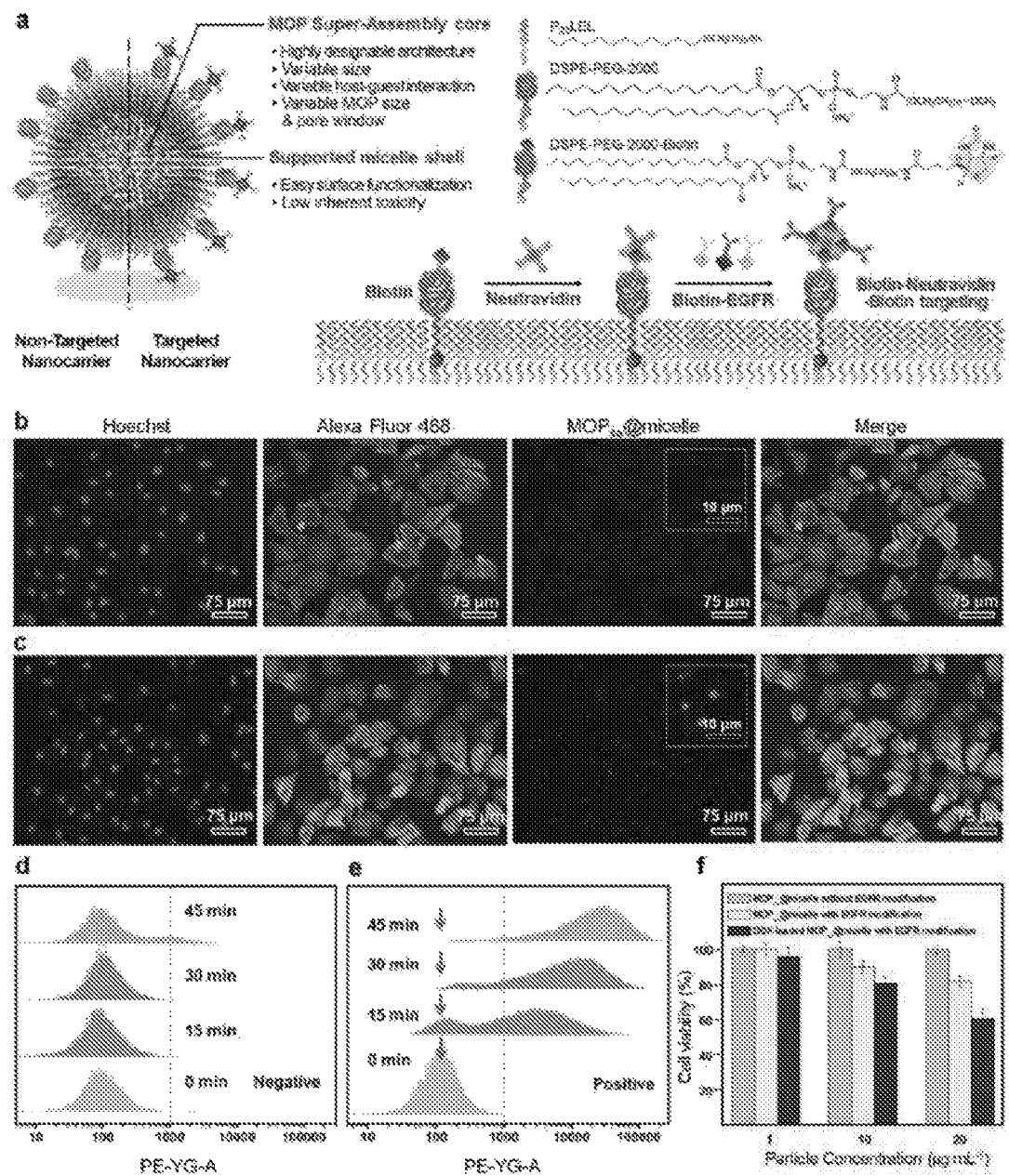
FIGS. 5A-5F. A) Schematic illustration of the construction of EGFR-modified $MOP_{sa}$@micelle for targeted drug delivery. Fluorescence microscopy images of A549 cells treated with $MOP_{sa}$@micelles B) without and C) with EGFR modification after incubation for 45 minutes at 37° C. Flow cytometry analysis of A549 cancer cells incubated with red fluorescent dye-loaded $MOP_{sa}$@micelles D) without or E) with EGFR modification at multiple time points. F) Sustained viability of A549 cells after incubation of $MOP_{sa}$@micelle with or without EGFR modification or DOX loading for 1 hour.
Figure 19:
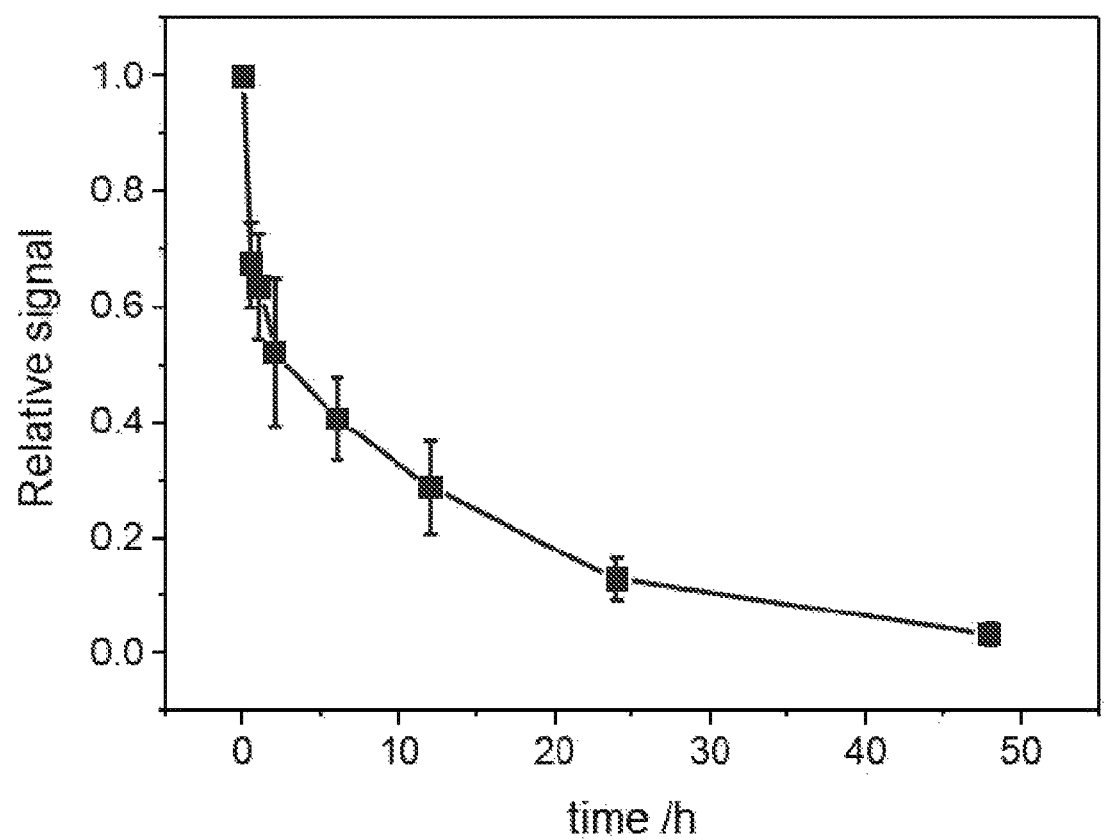
FIG. 19. The circulation of the created MOP$_{sa}$@ micelle NPs in mice.
Figure 20:
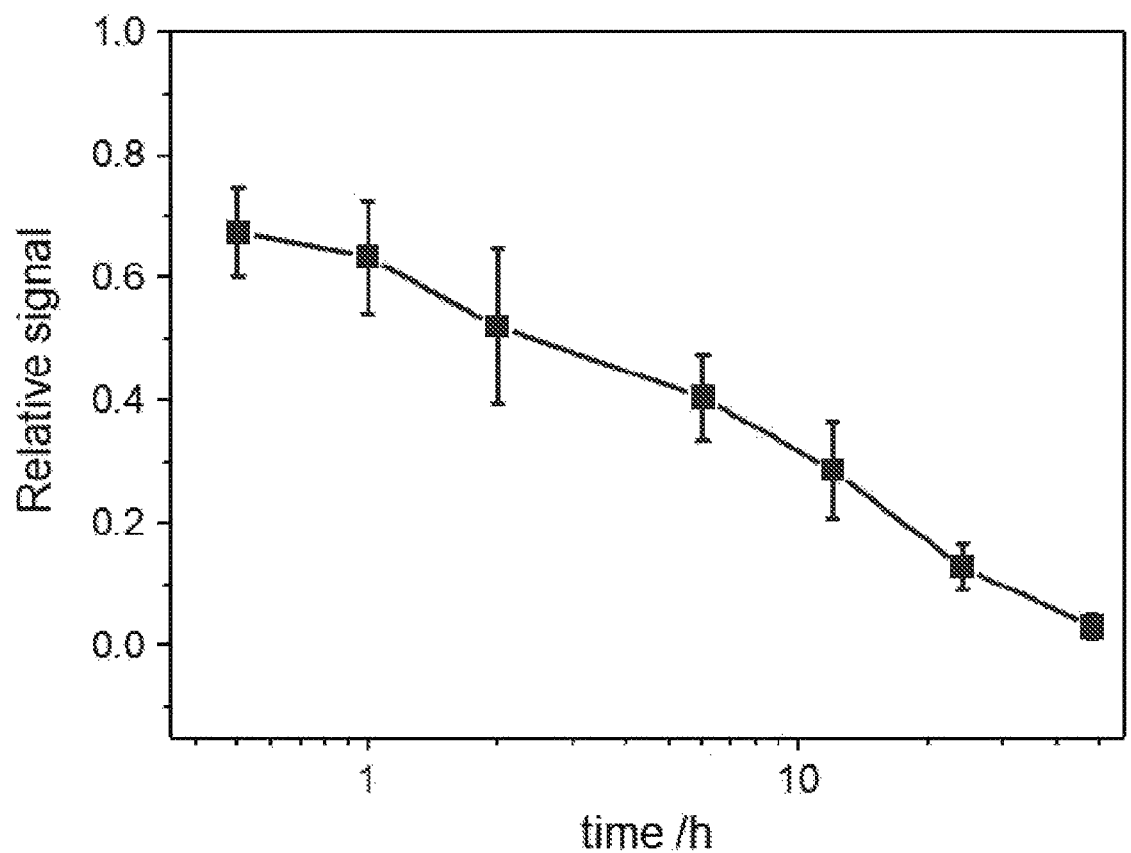
FIG. 20. Semilog plot of the circulation of the created MOP$_{sa}$@ micelle NPs in mice.

The potential of the MOP$_{sa}$@micelle carriers for targeted drug delivery was eventually assessed on cancer cells. The A549 cancer cell line was selected owing to the high expression of the epidermal growth factor receptor (EGFR). Targeting was accomplished through the conjugation of biotin—NeutrAvidin—biotin moieties onto MOP$_{sa}$@micelle with anti-EGFR monoclonal antibodies as depicted in FIG. 5A. The preparation involved polyoxyethylene (23) lauryl ether (P$_{23}$LEL):1,2-distearoyl-sn-glycero-3-phosphoethanolamine-N-[biotinyl(polyethylene glycol)-2000] (ammonium salt)) (DSPE-PEG-2000-biotin):1,2-distearoyl-sn-glycero-3-phosphoeth-anolamine-N-[methoxy (polyethyleneglycol)-2000] (ammonium salt) (DSPE-PEG2000) with molar ratios of 92:4:4. To examine the targeting specificity, MOP$_{sa}$@micelles with or without EGFR modification were incubated with A549 cells. The confocal laser scanning microscopy images of A549 cells cultured with both red fluorescent dye sulforhodamine B-labeled MOP$_{sa}$@micelles (50 μg mL$^{-1}$) at 37° C. for 45 minutes are shown in FIGS. 5B-C. The cellular filamentous actin network and nuclei were stained with fluorescent probes Alexa Fluor 488 phalloidin and Hoechst 33 342, respectively. Significant selective binding and internalization of the EGFR-modified MOP$_{sa}$@micelles to A549 cells were observed. Binding or internalization of particles without EGFR functionalization was not observed. It was thus concluded that the MOP$_{sa}$@micelles were mostly internalized into the cells via receptor-mediated endocytosis. To elucidate the receptor-ligand binding kinetics, both dye-labeled MOP$_{sa}$@ micelles were incubated with A549 cells for different times. After incubation for 15 minutes, a small binding shift occurred for the control samples, even after extending the incubation time to 45 minutes (FIGS. 5D,E). Regarding the EGFR-modified samples, however, an obvious binding shift was observed within 15 minutes, and a maximal binding shift was observed after 45 minutes. The targeted cell killing efficacy of MOP$_{sa}$@micelles nanocarriers against A549 cells was also measured. The viabilities of the A549 cells after being incubated for 2 hours with a series of concentrations of free DOX and MOP$_{sa}$@micelles with or without DOX loading were quantified. As shown in FIG. 19, free DOX exhibited dose-dependent toxicity to A549 cells. In contrast, MOP$_{sa}$@micelles with the same DOX loading displayed a lower toxicity, indicating that DOX had been trapped in the MOP$_{sa}$@micelle nanocarrier and thus reduced the killing efficacy of DOX to the cells. To evaluate the target-specific drug delivery, A549 cells were incubated with increasing concentrations of MOP$_{sa}$@micelles with or without EGFR modification or DOX loading in complete media under standard culturing conditions. In FIG. 5F, compared to the MOP$_{sa}$@micelles with (18.0%) or without EGFR modification (0.1%), the DOX-loaded targeted MOP$_{sa}$@micelle causes much higher cell death of ≈42.0%, indicating an enhanced killing efficacy that was attributed to the successful release of DOX inside A549 cells.

Figure 21:
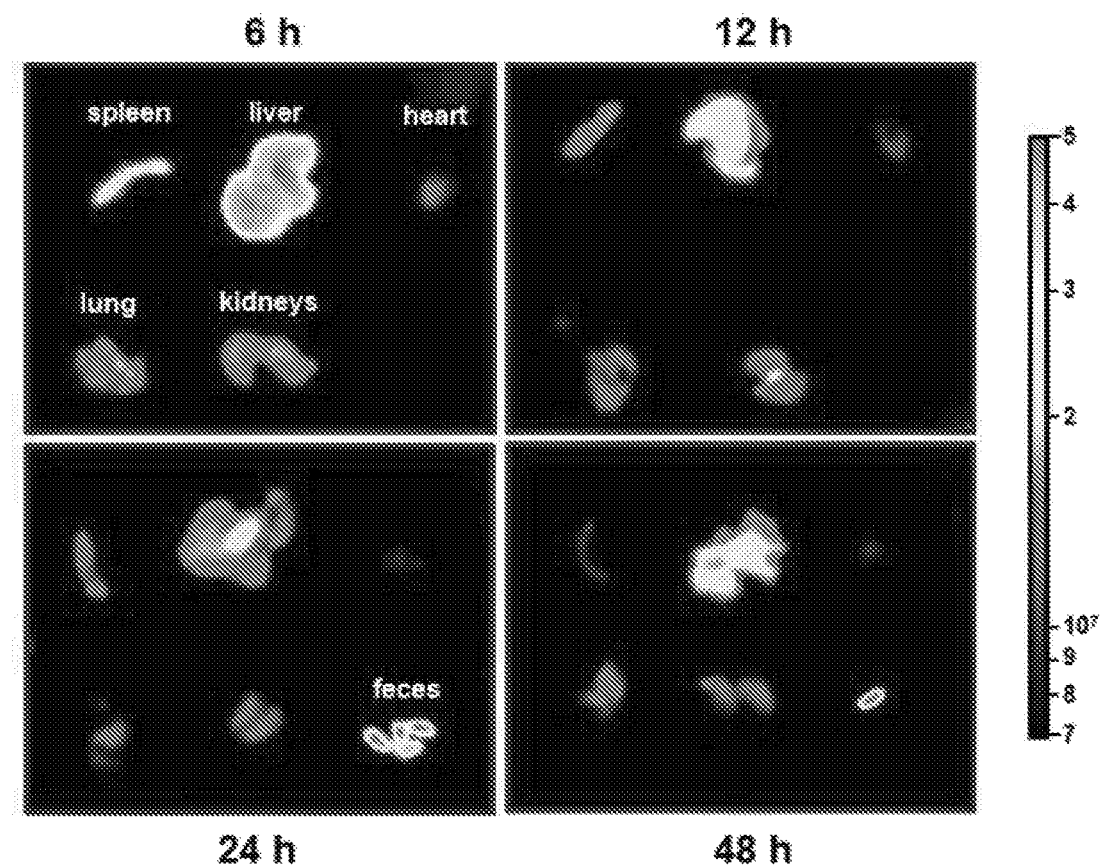
FIG. 21. Fluorescence images of different organs at 6, 12, 24, and 48 hours after intravenous administration of the MOP$_{sa}$@ micelle NPs.
Figure 22:
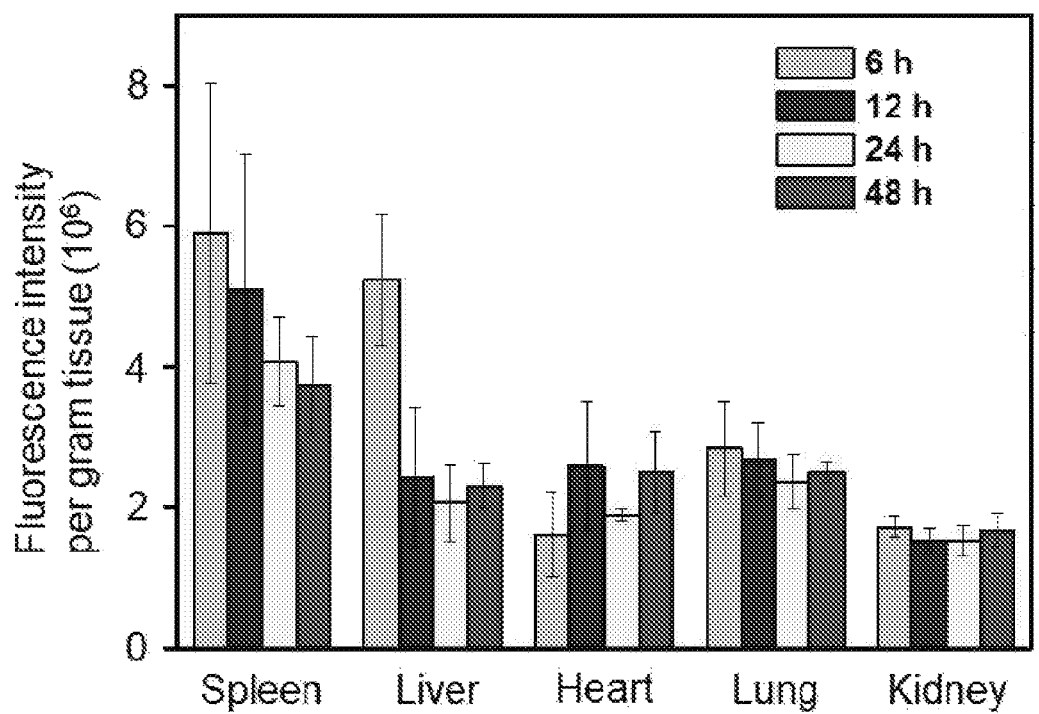
FIG. 22. Fluorescence intensity per gram of tissue at 6, 12, 24, and 48 hours after intravenous administration of the MOPsa@ micelle NPs.

Furthermore, to evaluate the potential in vivo application of the MOP$_{sa}$@ micelles, the related circulation and biodistribution were assessed using a mouse model. Mice were injected with CdSe/ZnS QD (627 nm) labeled MOP$_{sa}$@ micelles by retro-orbital injection at a dose of 150 μg NPs/mouse. To study the circulation half-life, at various time points following the injection, blood was collected from the eye socket of the mice to evaluate the NPs remaining in circulation. At 24 and 48 hours postinjection, the MOP$_{sa}$@ micelles exhibited 12% and 3% overall retention in mice blood (FIG. 19), respectively, similar to the 11% and 2% exhibited by PEG-coated NPs (Hu et al., 2011). The semilog plot of retention-circulation time (FIG. 21) illustrates an exponential decrease in particle concentration over time, indicating that the MOP$_{sa}$@micelle NP circulation followed a one-way nonlinear clearance model. Based on this pharmacokinetic model, the half-life (i.e., time at which 50% of the particles are cleared) of MOP$_{sa}$@micelle NP was calculated to be 5.6 hours. Moreover, to analyze the related biodistribution, at 6, 12, 24, and 48 hours postinjection, mice were euthanized and their liver, spleen, kidneys, heart, lungs, and blood were harvested for fluorescence analysis (Figure S16, Supporting Information). The majority of fluorescence signal was found in the two primary filtering organs (FIG. 21), the liver and spleen at 6 hours postinjection, supporting removal by the reticuloendothelial system (RES) (Zhang et al., 2009; Cui et al., 2015). This behavior is consistent with the behavior of nanocarriers employed currently for in vivo delivery (Lipka et al., 2010). After 24 hours a visible signal was found in the feces (FIG. 22), indicating the MOP$_{sa}$@micelle NPs can be cleared from the body. These results demonstrate that our developed MOP$_{sa}$@micelle NP has good in vivo residence time and clearance behavior needed for targeted cancer therapies.

In summary, the superassembly of nanosized metal-organic polyhedra and their biomimetic coatings of lipid bilayers are described herein, which synergistically combine the advantages of micelles and supramolecular coordination cages for biomedical applications. The hydrophobic self-assembly of the MOP nanocages was facilitated via their surface modification using dodecyl groups, and remarkable long-range hexagonal order was visualized via high-resolution electron micrographs. Homogeneous and tunable size distributions of MOP$_{sa}$@ micelle particles were obtained by simply adjusting the MOP concentration. PEGylated nanomaterials showed good biocompatibility and were stable in biorelevant media, as demonstrated by systematic in vitro studies. The MOP superassembly could be loaded with various dyes and drugs, QDs and gold nanoparticles, and could function as multidrug delivery systems with specific cargo loading amounts through the precise mixing of multiple cargo-loaded MOP samples. Through the surface modification with targeting moieties, the MOP$_{sa}$@ micelles were successfully synthesized and applied to cancer cells where we observed selective cytotoxicity. Finally, in vivo experiments in a mouse model demonstrated good in vivo circulation of MOP$_{sa}$@micelles. The metal-organic polyhedral supra-assembly within micelles concept has thus been validated and expected to be applicable to a range of biomedical applications as well as for separation, sensing, and catalytic processes.

REFERENCES

Ahmad et al., Chem. Soc. Rev., 44:9 (2015);
Blanco et al., Nat. Biotechnol., 33:941(2015).
Cook et al., Acc. Chem. Res., 46:2464 (2013).
Croissant et al., Adv. Healthcare Mater., 7:1700831 (2018).
Croissant et al., Adv. Mater., 29:1604634 (2017).
Cui et al., ACS Nano, 9:1571 (2015).
Elsabahy et al., Chem. Rev., 115:10967 (2015).
Fujita et al., Chem 1:91 (2016).
Grim et al., Chem. Soc. Rev., 45:6520 (2016).
Grishagin et al., Proc. Natl. Acad. Sci. USA, 111:18448 (2014).
Han et al., Angew. Chem. 125, 1358 (2013).
Han et al., Angew. Chem., Int. Ed. Engl., 52:1319 (2013);
Harris et al., Chem. Commun., 49:6703 (2013).
Hu et al., Proc. Natl. Acad. Sci. USA, 108:10980 (2011).
Lin et al., J. Am. Chem. Soc., 132:4834 (2010).
Lin et al., J. Am. Chem. Soc., 132:4834 (2010).
Lipka, Biomaterials, 31:6574 (2010).
Mitragotri et al., Nat. Rev. Drug Discovery, 13:655(2014).
Park et al., Angew. Chem., 126:5952 (2014).
Park et al., Angew. Chem., Int. Ed. Engl., 53:5842 (2014).
Pozzi et al., Nanoscale, 6:2782 (2014).
Richardson et al., Chem. Rev., 116:14828 (2016).
Rodriguez et al., J. Am. Chem. Soc., 139:55 (2017).
Samanta et al., J. Am. Chem. Soc., 138:14488 (2016).
Samanta et al., J. Am. Chem. Soc., 139:9066 (2017).
Schmitt et al., J. Am. Chem. Soc., 134:754 (2012).
Sun et al., Science, 328:1144 (2010).
Therrien et al., Angew. Chem., 120:3833 (2008).
Therrien et al., Angew. Chem., Int. Ed. Engl., 47:3773 (2008).
Vardhan et al., Coord. Chem. Rev., 306:171 (2016).
Xiong et al., Nano Lett., 13:1041 (2013).
Xu et al., Chem.—Eur. J., 23:3542 (2017).
Yu et al., Proc. Natl. Acad. Sci. USA, 113:13720 (2016).
Zhang et al., Biomaterials, 30:1928 (2009).
Zhao et al., Adv. Mater., 23:90 (2011).
Zheng et al., Chem. Sci., 6:1189 (2015).
Zhu et al., Adv. Funct. Mater., 28:1705274 (2018).

All publications, patents and patent applications are incorporated herein by reference. While in the foregoing specification this invention has been described in relation to certain preferred embodiments thereof, and many details have been set forth for purposes of illustration, it will be apparent to those skilled in the art that the invention is susceptible to additional embodiments and that certain of the details described herein may be varied considerably without departing from the basic principles of the invention.

What is claimed is:

1. A method to prepare a population of metal-organic polyhedra (MOP) supported micelle nanoparticles (NPs), comprising:
   combining an amount of metal and an amount of an organic ligand comprising one or more hydrophobic chains under conditions to form a population of metal-organic polyhedra units; and
   combining an amount of the population of metal-organic polyhedra units and an amount of a micellar solution under conditions to form single MOP-supported micelle nanoparticles (NPs).

2. The method of claim 1 wherein the metal is palladium, copper, zinc, platinum, manganese or beryllium.

3. The method of claim 1 wherein the hydrophobic chain is a C1-C20 alkyl chain.

4. The method of claim 1 wherein the ligand comprises a carboxylate, such as 1,4-benzenedicarboxylic, heterocyclic azolate, pyridine, thiophene, furan, pyrrole, or cyanide.

5. The method of claim 1 wherein the conditions to form single MOP-supported micelle nanoparticles comprise sonication.

6. The method of claim 1 wherein the conditions to form metal-organic polyhedra units yield a precipitate.

7. The method of claim 1 wherein the conditions to form metal-organic polyhedra units comprise applying heat.

8. The method of claim 1 wherein the diameter of the metal-organic polyhedra unit is from about 1 nm to about 15 nm, about 10 nm to about 25 nm or about 3 nm to about 10 nm.

9. The method of claim 1 wherein the diameter of the micelle is from about 10 nm to about 25 nm, 10 nm to about 20 nm about 15 nm to about 25 nm, about 100 nm to about 800 nm, about 200 nm to about 500 nm, about 500 nm to about 900 nm, about 1000 nm to about 3000 nm or about 1500 nm to about 2500 nm.

10. The method of claim 1 wherein the micelle solution comprises PEG, DSPE, or combination thereof.

11. The method of claim 10 wherein the PEG has 4, 5, 6, 7, 8, 9, 10, 11, 12, 13, 14, 15, 16, 17, 18, 19, 20, 21, 22, 23, 24, or 25 PEO units.

12. The method of claim 1 further comprising forming superassemblies of the micelle.

13. The method of claim 1 wherein the MOP-supported micelle nanoparticles further comprise one or more cargo or targeting molecules.

14. The method of claim 13 wherein the one or more cargo molecules comprise a drug, a dye a contrast agent, an antibody or a fragment thereof, a protein ligand, a quantum dot or a gold nanoparticle.

15. A population of single MOP-supported micelle nanoparticles prepared by the method of claim 1.

16. A population of superassemblies of metal-organic polyhedral prepared by the method of claim 12.

17. A method to prevent, inhibit or treat cancer, to deliver a drug or for imaging in a mammal, comprising: administering to the mammal an effective amount of a composition comprising the population of claim 15 which comprises drugs or an imaging agent.

18. A support comprising the population of claim 15.

19. The support of claim 18 which is a membrane.

20. A micelle comprising a plurality of metal-organic polyhedral units having metal nodes and an organic ligand comprising one or more hydrophobic chains.

* * * * *